(12) United States Patent
Li et al.

(10) Patent No.: US 12,030,880 B2
(45) Date of Patent: Jul. 9, 2024

(54) IMINOSULFANONE COMPOUND AS BROMODOMAIN PROTEIN INHIBITOR AND PHARMACEUTICAL COMPOSITION AND MEDICAL USE THEREOF

(71) Applicants: CHIA TAI TIANQING PHARMACEUTICAL GROUP CO., LTD., Lianyungang (CN); SHOUYAO HOLDINGS (BEIJING) CO., LTD., Beijing (CN); LIANYUNGANG RUNZHONG PHARMACEUTICAL CO., LTD., Lianyungang (CN)

(72) Inventors: Jijun Li, Beijing (CN); Yan Zhu, Beijing (CN); Yeliu Wang, Beijing (CN); Xianxing Shang, Beijing (CN); Huting Wang, Beijing (CN); Weinan He, Beijing (CN); Qin Yan, Beijing (CN); Yinghui Sun, Beijing (CN); Kai Zhang, Beijing (CN); Chang Lu, Beijing (CN); Hongjiang Xu, Lianyungang (CN); Xin Tian, Lianyungang (CN); Ling Yang, Lianyungang (CN)

(73) Assignees: Chia Tai Tianqing Pharmaceutical Group Co., Ltd., Lianyungang (CN); Shouyao Holdings (Beijing) Co., Ltd., Beijing (CN); Lianyungang Runzhong Pharmaceutical Co., Ltd., Lianyungang (CN)

( * ) Notice: Subject to any disclaimer, the term of this patent is extended or adjusted under 35 U.S.C. 154(b) by 612 days.

(21) Appl. No.: 17/262,053

(22) PCT Filed: Jul. 25, 2019

(86) PCT No.: PCT/CN2019/097692
§ 371 (c)(1),
(2) Date: Jan. 21, 2021

(87) PCT Pub. No.: WO2020/020288
PCT Pub. Date: Jan. 30, 2020

(65) Prior Publication Data
US 2021/0300923 A1 Sep. 30, 2021

(30) Foreign Application Priority Data

Jul. 25, 2018 (CN) .......... 201810825047.X
May 17, 2019 (CN) .......... 201910410273.6

(51) Int. Cl.
C07D 471/04 (2006.01)
A61P 35/02 (2006.01)

(52) U.S. Cl.
CPC .......... *C07D 471/04* (2013.01); *A61P 35/02* (2018.01)

(58) Field of Classification Search
CPC ............................................ C07D 471/04
See application file for complete search history.

(56) References Cited

U.S. PATENT DOCUMENTS

| 9,296,741 B2 * | 3/2016 | Wang ............... A61K 31/541 |
| 11,584,756 B2 * | 2/2023 | Pham ............... C07D 495/04 |
| 2016/0143916 A1 | 5/2016 | Wang |

FOREIGN PATENT DOCUMENTS

| CN | 104136435 A | 11/2014 |
| CN | 108069958 A | 5/2018 |
| WO | WO 2014/206345 A1 | 12/2014 |
| WO | WO 2017/063959 A1 | 4/2017 |
| WO | WO 2017/177955 A1 | 10/2017 |
| WO | WO 2018/130174 A1 | 7/2018 |

OTHER PUBLICATIONS

Su et al (2018) : STN International, CAPLUS database, Accession No. 2018 : 1332530.*
International Search Report in International Patent Application No. PCT/CN2019/097692, mailed Oct. 17, 2019 (6 pages).
McDaniel, K. F. et al., "Discovery of N-(4-(2, 4-Difluorophenoxy)-3-(6-methyl-7-oxo-6, 7-dihydro-1 H-pyrrolo[2,3-c] pyridin-4-yl)phenyl) ethanesulfonamide (ABBV-075/Mivebresib), a Potent and Orally Available Bromodomain and Extraterminal Domain (BET) Family Bromodomain Inhibitor," Journal of Medicinal Chemistry, 60(20): 8369-8384 (2017).
Extended European Search Report in European Patent Application No. EP 19842279.2, mailed Feb. 8, 2022 (10 pages).

* cited by examiner

*Primary Examiner* — Golam M Shameem
(74) *Attorney, Agent, or Firm* — NIXON PEABODY LLP

(57) ABSTRACT

The present invention relates to a iminosulfanone compound represented by formula (I) as a bromodomain protein inhibitor and a pharmaceutically acceptable salt thereof and to a preparation method, pharmaceutical composition, and medical use thereof.

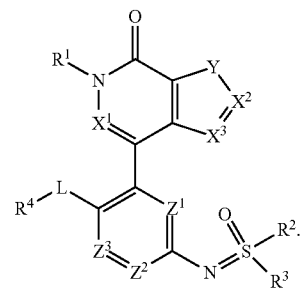

18 Claims, No Drawings

IMINOSULFANONE COMPOUND AS BROMODOMAIN PROTEIN INHIBITOR AND PHARMACEUTICAL COMPOSITION AND MEDICAL USE THEREOF

REFERENCES TO RELATED APPLICATIONS

The present application is a U.S. national stage of PCT/CN2019/097692, filed on Jul. 25, 2019, which claims the benefit and priority to Chinese Patent No. 201910410273.6 filed with the National Intellectual Property Administration, PRC on May 17, 2019, and Chinese Patent No. 201810825047.X filed with the National Intellectual Property Administration, PRC on Jul. 25, 2018, which are incorporated herein by reference in their entireties.

TECHNICAL FIELD

The present application relates to an iminosulfone compound as a bromodomain protein inhibitor and a pharmaceutically acceptable salt thereof. The present application also relates to a method for preparation, a pharmaceutical composition and medical use thereof.

BACKGROUND

The epigenetic regulation of transcriptional genes plays an important role in the development of diseases such as tumors, inflammations, and metabolism. The acetylation of N-terminal residues of nucleosomal histone lysine is especially important for the regulation of epigenetic genes. However, histone acetylation is usually most commonly associated with the activation of gene transcription, and the recognition of histone-lysine acetylation is a key step for the involvement of the histone acetylation in epigenetic regulation. Bromodomains (BRDs) are a class of conserved protein domains capable of specifically recognizing acetylated lysine (KAc) in histones, and enable chromatin-remodeling factors, transcription factors and other related proteins to enrich at specific gene transcription sites through combination with acetylated lysine, to change the activity of RNA II polymerase, thereby synergistically completing gene expression regulation (Filippakopoulos P, Picaud S, Mangos M et al, Cell, 2012, 149 (1): 214-231).

BET (Bromodomain and Extra Terminal) proteins comprise two mutually-related bromodomain centers and an extra-terminal domain, and are divided into four kinds of proteins: Brd2, Brd3, Brd4 and BrdT, according to different amino acid sequences, in which Brd2-Brd4 are widely distributed in various organs of a human body. BET is a class of transcriptional regulatory proteins that play a very important role in the regulation of gene expression through the interaction with chromatins. BET proteins have a bidirectional regulatory functions of co-activation or co-suppression of the intracellular reticular signal transduction pathways, such as transcription of insulin, adipogenesis in lipid tissue, differentiation of the hematopoietic system, etc. (Belkina A C, Denis G V, Nature reviews Cancer, 2012, 12 (7): 465-477). Recent studies have demonstrated that medicaments targeting BET proteins can be used to treat cancers (Zuber J, Shi J, Wang E et al, Nature, 2011, 478 (7370): 524-528), inflammations (Huang B, Yang X D, Zhou M M et al, Molecular and cellular biology, 2009, 29 (5): 1375-1387), kidney diseases (Zhang G, Liu R, Zhong Y et al, Journal of Biological Chemistry, 2012, 287 (34): 28840-28851), autoimmune diseases (Denis G V. Discovery Medicine, 2010, 10 (55): 489), and male antifertility (Matzuk M M, McKeown M R, Filippakopoulos P et al, Cell, 2012, 150 (4): 673-684), and the like. Therefore, BET proteins have increasingly become one of the important targets in the field of epigenetics, and have attracted great attention from various pharmaceutical companies and scientific research institutes.

To date, a number of small molecule inhibitors that selectively target the bromodomain of BET proteins have been reported (WO2009084693, WO2009158404, WO2011143669, WO2011161031, WO2012075383, WO2013097601, US2015246923, WO2017177955, etc.), with some medicament candidates (ABBV-075, CPI-0610, OTX015, GSK525762, TEN-010, etc.) in the clinical trial phase. The present application takes BET proteins as a target, and has developed a novel iminosulfone small molecular compound for treating tumors, inflammations, metabolic diseases and the like.

SUMMARY OF THE INVENTION

The present application provides a compound of formula I or a pharmaceutically acceptable salt thereof,

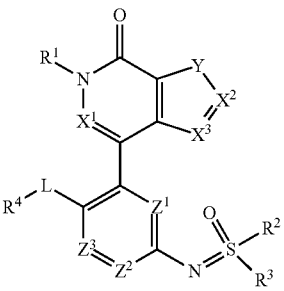

wherein,
$R^1$ is selected from the group consisting of H, $C_1$-$C_3$ alkyl, and $C_1$-$C_3$ acyl, the $C_1$-$C_3$ alkyl or $C_1$-$C_3$ acyl is optionally substituted with one or more halogens; Y is selected from the group consisting of O, S, and $NR^Y$, the $R^Y$ is selected from the group consisting of H, $C_1$-$C_3$ alkyl, and $C_1$-$C_3$ acyl, the $C_1$-$C_3$ alkyl or $C_1$-$C_3$ acyl is optionally substituted with one or more halogens;
$X^1$ is selected from the group consisting of N and $CR^{X1}$, the $R^{X1}$ is selected from the group consisting of H, $C_1$-$C_6$ alkyl, halogen, and $C_1$-$C_6$ haloalkyl;
$X^2$ is selected from the group consisting of N and $CR^{X2}$, and $X^3$ is selected from the group consisting of N and $CR^{X3}$, the $R^{X2}$ and $R^{X3}$ are each independently selected from the group consisting of H, halogen, $C_1$-$C_6$ alkyl, $C_2$-$C_6$ alkenyl, $C_2$-$C_6$ alkynyl, —C(O)$OR^a$, —C(O)$NR^bR^c$, —C(O)$R^d$, —S(O)$_2R^e$, and —S(O)$_2NR^bR^c$, the $C_1$-$C_6$ alkyl, $C_2$-$C_6$ alkenyl, or $C_2$-$C_6$ alkynyl is optionally substituted with one or more halogens, hydroxyl, amino, nitro, or cyano;
$Z^1$ is selected from the group consisting of N and $CR^{Z1}$, $Z^2$ is selected from the group consisting of N and $CR^{Z2}$, and $Z^3$ is selected from the group consisting of N and $CR^{Z3}$, the $R^{Z1}$, $R^{Z2}$, and $R^{Z3}$ are each independently selected from the group consisting of H, $C_1$-$C_6$ alkyl, $C_2$-$C_6$ alkenyl, $C_2$-$C_6$ alkynyl, halogen, cyano, and nitro, the $C_1$-$C_6$ alkyl, $C_2$-$C_6$ alkenyl, or $C_2$-$C_6$ alkynyl is optionally substituted with one or more halogens, hydroxyl, amino, nitro, or cyano;

$R^2$ and $R^3$ are each independently selected from the group consisting of halogen, hydroxyl, $C_1$-$C_6$ alkyl, $C_2$-$C_6$ alkenyl, $C_2$-$C_6$ alkynyl, $C_1$-$C_6$ alkoxy, $C_1$-$C_6$ alkylamino, and $(C_1$-$C_6$ alkyl$)_2$ amino, the $C_1$-$C_6$ alkyl, $C_2$-$C_6$ alkenyl, $C_2$-$C_6$ alkynyl, $C_1$-$C_6$ alkoxy, $C_1$-$C_6$ alkylamino, or $(C_1$-$C_6$ alkyl$)_2$ amino is optionally substituted with one or more halogens, hydroxyl, amino, nitro, or cyano; or $R^2$ and $R^3$ are connected and form a 3-8 membered heterocycloalkyl together with an adjacent S atom, the 3-8 membered heterocycloalkyl optionally contains 1-3 heteroatoms selected from the group consisting of N, O, and S, in addition to the S atom to which $R^2$ and $R^3$ are both connected; and the ring carbon atoms of the 3-8 membered heterocycloalkyl are optionally substituted with one or more halogens, hydroxyl, amino, nitro, cyano, $C_1$-$C_6$ alkyl, $C_1$-$C_6$ haloalkyl, $C_1$-$C_6$ alkoxy, $C_1$-$C_6$ alkylamino, or $(C_1$-$C_6$ alkyl$)_2$ amino, or substituted with one or more oxo;

L is selected from the group consisting of a single bond, —O—, —NH—, —($C_1$-$C_3$ alkyl)-O—, —($C_1$-$C_3$ alkyl)-NH—, and —$C_1$-$C_3$ alkyl-; and $R^4$ is selected from the group consisting of $C_6$-$C_{10}$ aryl, $C_3$-$C_{10}$ cycloalkenyl, $C_3$-$C_{10}$ cycloalkyl, 3-10 membered heteroaryl, 3-10 membered heterocycloalkenyl, and 3-10 membered heterocycloalkyl, the 3-10 membered heteroaryl, 3-10 membered heterocycloalkenyl, or 3-10 membered heterocycloalkyl each independently contains 1-3 heteroatoms selected from the group consisting of N, O, and S; and $R^4$ is optionally substituted with one or more halogens, hydroxyl, amino, nitro, cyano, $C_1$-$C_6$ alkyl, $C_1$-$C_6$ haloalkyl, $C_1$-$C_6$ alkoxy, $C_1$-$C_6$ alkylamino, $(C_1$-$C_6$ alkyl$)_2$ amino, —C(O)OR$^a$, —C(O)NR$^b$R$^c$, —C(O)R$^d$, —S(O)$_2$R$^e$, —NHS(O)$_2$R$^e$, or —S(O)$_2$NR$^b$R$^c$, or substituted with one or more oxo;

the R$^a$, R$^b$, R$^c$, R$^d$, and R$^e$ are each independently selected from the group consisting of H, $C_1$-$C_6$ alkyl, and $C_1$-$C_6$ haloalkyl.

In some embodiments of the present application, the $R^1$ is selected from the group consisting of H and $C_1$-$C_3$ alkyl, the $C_1$-$C_3$ alkyl is optionally substituted with one or more F, Cl, or Br.

In some embodiments of the present application, the $R^1$ is selected from the group consisting of H, methyl, ethyl, propyl, and trifluoromethyl.

In some embodiments of the present application, the Y is selected from the group consisting of NR$^Y$, the R$^Y$ is selected from the group consisting of H and $C_1$-$C_3$ alkyl, the $C_1$-$C_3$ alkyl is optionally substituted with one or more F, Cl, or Br.

In some embodiments of the present application, the Y is selected from the group consisting of NH and N(CH$_3$).

In some embodiments of the present application, the $X^1$ is selected from CR$^{X1}$, the R$^{X1}$ is selected from the group consisting of H, $C_1$-$C_4$ alkyl, F, Cl, Br, and $C_1$-$C_4$ alkyl substituted with F, Cl, or Br.

In some embodiments of the present application, the $X^1$ is selected from CH.

In some embodiments of the present application, the $X^2$ is selected from CR$^{X2}$, the R$^{X2}$ is selected from the group consisting of H, —C(O)OR$^a$, and —C(O)NR$^b$R$^c$.

In some embodiments of the present application, the $X^2$ is selected from CR$^{X2}$, the R$^{X2}$ is selected from the group consisting of H, —C(O)OH, —C(O)OCH$_3$, —C(O)OC$_2$H$_5$, —C(O)NH$_2$, —C(O)NHCH$_3$, —C(O)NHC$_2$H$_5$, —C(O)N(CH$_3$)$_2$, —C(O)N(C$_2$H$_5$)$_2$, and —C(O)NHCH$_2$CF$_3$.

In some embodiments of the present application, the $X^3$ is selected from CR$^{X3}$, the R$^{X3}$ is selected from the group consisting of H and $C_1$-$C_4$ alkyl, the $C_1$-$C_4$ alkyl is optionally substituted with one or more F, Cl, Br, hydroxyl, amino, nitro, or cyano.

In some embodiments of the present application, the $X^3$ is selected from CH.

In some embodiments of the present application, the $Z^1$ is selected from the group consisting of N and CR$^{Z1}$, the R$^{Z1}$ is selected from the group consisting of H, $C_1$-$C_4$ alkyl, $C_2$-$C_4$ alkenyl, $C_2$-$C_4$ alkynyl, halogen, cyano, and nitro, the $C_1$-$C_4$ alkyl, $C_2$-$C_4$ alkenyl, or $C_2$-$C_4$ alkynyl is optionally substituted with one or more halogens, hydroxyl, amino, nitro, or cyano.

In some embodiments of the present application, the $Z^1$ is selected from the group consisting of N and CH.

In some embodiments of the present application, the $Z^1$ is selected from N.

In some embodiments of the present application, the $Z^2$ is selected from CR$^{Z2}$, the R$^{Z2}$ is selected from the group consisting of H, $C_1$-$C_4$ alkyl, $C_2$-$C_4$ alkenyl, $C_2$-$C_4$ alkynyl, halogen, cyano, and nitro, the $C_1$-$C_4$ alkyl, $C_2$-$C_4$ alkenyl, or $C_2$-$C_4$ alkynyl is optionally substituted with one or more F, Cl, Br, hydroxyl, amino, nitro, or cyano.

In some embodiments of the present application, the $Z^2$ is selected from CH.

In some embodiments of the present application, the $Z^3$ is selected from the group consisting of N and CR$^{Z3}$, the R$^{Z3}$ is selected from the group consisting of H, $C_1$-$C_4$ alkyl, $C_2$-$C_4$ alkenyl, $C_2$-$C_4$ alkynyl, halogen, cyano, and nitro, the $C_1$-$C_4$ alkyl, $C_2$-$C_4$ alkenyl, or $C_2$-$C_4$ alkynyl is optionally substituted with one or more F, Cl, Br, hydroxyl, amino, nitro, or cyano.

In some embodiments of the present application, the $Z^3$ is selected from the group consisting of N and CH.

In some embodiments of the present application, the $Z^3$ is selected from N.

In some embodiments of the present application, the $R^2$ and $R^3$ are each independently selected from the group consisting of $C_1$-$C_4$ alkyl, $C_2$-$C_4$ alkenyl, $C_2$-$C_4$ alkynyl, $C_1$-$C_4$ alkoxy, $C_1$-$C_4$ alkylamino, and $(C_1$-$C_4$ alkyl$)_2$ amino, the $C_1$-$C_4$ alkyl, $C_2$-$C_4$ alkenyl, $C_2$-$C_4$ alkynyl, $C_1$-$C_4$ alkoxy, $C_1$-$C_4$ alkylamino, or $(C_1$-$C_4$ alkyl$)_2$ amino is optionally substituted with one or more F, Cl, Br, hydroxyl, amino, nitro, or cyano; or $R^2$ and $R^3$ are connected and form a 4-6 membered heterocycloalkyl together with an adjacent S atom, the 4-6 membered heterocycloalkyl optionally contains 1-3 heteroatoms selected from the group consisting of N, O and S in addition to the S atom to which $R^2$ and $R^3$ are both connected; and the ring carbon atoms of the 4-6 membered heterocycloalkyl are optionally substituted with one or more F, Cl, Br, hydroxyl, amino, nitro, cyano, $C_1$-$C_4$ alkyl, $C_1$-$C_4$ haloalkyl, $C_1$-$C_4$ alkoxy, $C_1$-$C_4$ alkylamino, or $(C_1$-$C_4$ alkyl$)_2$ amino, or substituted with one or more oxo.

In some embodiments of the present application, the $R^2$ and $R^3$ are each independently selected from the group consisting of methyl, ethyl, propyl, and trifluoromethyl; or $R^2$ and $R^3$ are connected and form

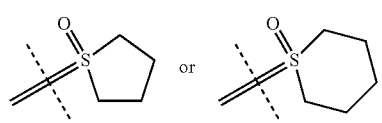

together with an adjacent =S=O.

In some embodiments of the present application, the L is selected from the group consisting of a single bond, —O—, —NH—, and —(C₁-C₃ alkyl)-O—.

In some embodiments of the present application, the R⁴ is selected from the group consisting of phenyl, naphthyl, piperidinyl, pyridinyl, imidazolyl, pyrazolyl, pyrazinyl, piperazinyl, thienyl, furanyl, thiazolyl, isothiazolyl, oxazolyl, isoxazolyl, 1,4-dihydropyridinyl, and tetrahydrofuranyl; the R⁴ is optionally substituted with one or more F, Cl, Br, cyano, methyl, ethyl, propyl, butyl, trifluoromethyl, methoxy, ethoxy, propoxy, methylamino, ethylamino, propylamino, (methyl)₂ amino, (ethyl)₂ amino, (propyl)₂ amino, —C(O)OH, —C(O)OCH₃, —C(O)OC₂H₅, —C(O)NH₂, —C(O)NHCH₃, —C(O)NHC₂H₅, —C(O)N(CH₃)₂, —C(O)N(C₂H₅)₂, acetyl, —S(O)₂CH₃, —S(O)₂C₂H₅, —NHS(O)₂CH₃, —NHS(O)₂C₂H₅, —S(O)₂NH₂, —S(O)₂NHCH₃, —S(O)₂NHC₂H₅, —S(O)₂N(CH₃)₂, or —S(O)₂N(C₂H₅)₂, or substituted with one or more oxo.

In some embodiments of the present application, the R⁴ is selected from the group consisting of

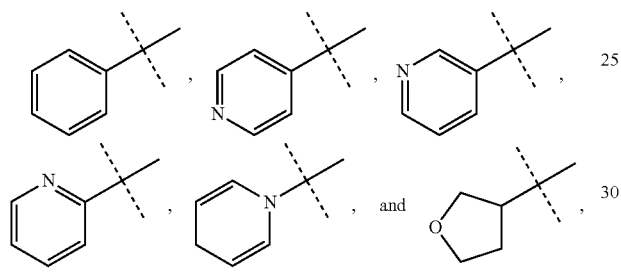

the R⁴ is optionally substituted with one or more F, Cl, Br, cyano, methyl, ethyl, propyl, butyl, trifluoromethyl, methoxy, ethoxy, propoxy, methylamino, ethylamino, propylamino, (methyl)₂ amino, (ethyl)₂ amino, (propyl)₂ amino, —C(O)OH, —C(O)OCH₃, —C(O)OC₂H₅, —C(O)NH₂, —C(O)NHCH₃, —C(O)NHC₂H₅, —C(O)N(CH₃)₂, —C(O)N(C₂H₅)₂, acetyl, —S(O)₂CH₃, —S(O)₂C₂H₅, —NHS(O)₂CH₃, —NHS(O)₂C₂H₅, —S(O)₂NH₂, —S(O)₂NHCH₃, —S(O)₂NHC₂H₅, —S(O)₂N(CH₃)₂, or —S(O)₂N(C₂H₅)₂, or substituted with one or more oxo.

In some embodiments of the present application, the R⁴ is selected from the group consisting of

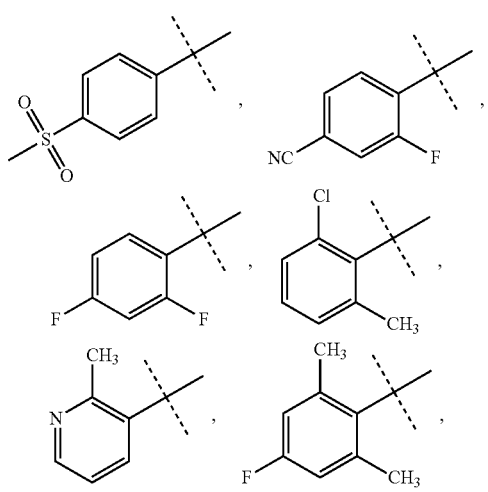

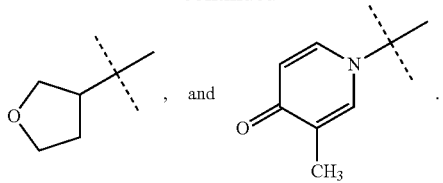

In a preferred embodiment, the compound of formula I or the pharmaceutically acceptable salt thereof is selected from a compound of formula II or a pharmaceutically acceptable salt thereof,

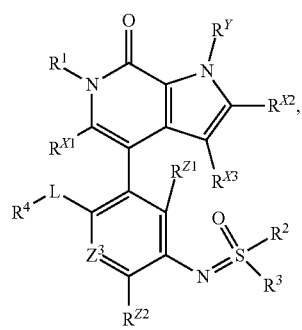

wherein R¹, R^Y, R^{X1}, R^{X2}, R^{X3}, R^{Z1}, R^{Z2}, Z³, R², R³, L and R⁴ are defined above.

The present application provides a compound of formula III or a pharmaceutically acceptable salt thereof,

III wherein, R¹ is selected from the group consisting of H, C₁-C₃ alkyl, and C₁-C₃ acyl, the C₁-C₃ alkyl or C₁-C₃ acyl is optionally substituted with one or more halogens;

R^Y is selected from the group consisting of H, C₁-C₃ alkyl, and C₁-C₃ acyl, the C₁-C₃ alkyl or C₁-C₃ acyl is optionally substituted with one or more halogens;

R^{X1} is selected from the group consisting of H, C₁-C₆ alkyl, halogen, and C₁-C₆ haloalkyl; R^{X2} is selected from the group consisting of H, halogen, C₁-C₆ alkyl, C₂-C₆ alkenyl, C₂-C₆ alkynyl, —C(O)OR^a, —C(O)NR^bR^c, —C(O)R^d, —S(O)₂R^e, and —S(O)₂NR^bR^c, the C₁-C₆ alkyl, C₂-C₆ alkenyl, or C₂-C₆ alkynyl is optionally substituted with one or more halogens, hydroxyl, amino, nitro, or cyano;

R² and R³ are each independently selected from the group consisting of halogen, hydroxyl, C₁-C₆ alkyl, C₂-C₆ alkenyl, C₂-C₆ alkynyl, C₁-C₆ alkoxy, C₁-C₆ alkylamino, and (C$_1$-C$_6$ alkyl)$_2$ amino, the C$_1$-C$_6$ alkyl, C$_2$-C$_6$ alkenyl, C$_2$-C$_6$ alkynyl, C$_1$-C$_6$ alkoxy, C$_1$-C$_6$ alkylamino, or (C$_1$-C$_6$ alkyl)$_2$ amino is optionally substituted with one or more halogens, hydroxyl, amino, nitro, or cyano; or R$^2$ and R$^3$ are connected and form a 3-8 membered heterocycloalkyl together with an adjacent S atom, the 3-8 membered heterocycloalkyl optionally contains 1-3 heteroatoms selected from the group consisting of N, O, and S, in addition to the S atom to which R$^2$ and R$^3$ are both connected; and the ring carbon atoms of the 3-8 membered heterocycloalkyl are optionally substituted with one or more halogens, hydroxyl, amino, nitro, cyano, C$_1$-C$_6$ alkyl, C$_1$-C$_6$ haloalkyl, C$_1$-C$_6$ alkoxy, C$_1$-C$_6$ alkylamino, or (C$_1$-C$_6$ alkyl)$_2$ amino, or substituted with one or more oxo;

L is selected from the group consisting of a single bond, —O—, —NH—, —(C$_1$-C$_3$ alkyl)-O—, —(C$_1$-C$_3$ alkyl)-NH—, and —C$_1$-C$_3$ alkyl-; and R$^4$ is selected from the group consisting of C$_6$-C$_{10}$ aryl, C$_3$-C$_{10}$ cycloalkenyl, C$_3$-C$_{10}$ cycloalkyl, 3-10 membered heteroaryl, 3-10 membered heterocycloalkenyl, and 3-10 membered heterocycloalkyl, the 3-10 membered heteroaryl, 3-10 membered heterocycloalkenyl, or 3-10 membered heterocycloalkyl each independently contains 1-3 heteroatoms selected from the group consisting of N, O, and S; and R$^4$ is optionally substituted with one or more halogens, hydroxyl, amino, nitro, cyano, C$_1$-C$_6$ alkyl, C$_1$-C$_6$ haloalkyl, C$_1$-C$_6$ alkoxy, C$_1$-C$_6$ alkylamino, (C$_1$-C$_6$ alkyl)$_2$ amino, —C(O)OR$^a$, —C(O)NR$^b$R$^c$, —C(O)R$^d$, —S(O)$_2$R$^e$, —NHS(O)$_2$R$^e$, or —S(O)$_2$NR$^b$R$^c$, or substituted with one or more oxo;

the R$^a$, R$^b$, R$^c$, R$^d$, and R$^e$ are each independently selected from the group consisting of H, C$_1$-C$_6$ alkyl, and C$_1$-C$_6$ haloalkyl.

In some embodiments of the compound of formula III or the pharmaceutically acceptable salt thereof disclosed herein, the R$^1$ is selected from the group consisting of H and C$_1$-C$_3$ alkyl, the C$_1$-C$_3$ alkyl is optionally substituted with one or more F, Cl, or Br.

In some embodiments of the compound of formula III or the pharmaceutically acceptable salt thereof disclosed herein, the R$^1$ is selected from the group consisting of H, methyl, ethyl, propyl, and trifluoromethyl.

In some embodiments of the compound of formula III or the pharmaceutically acceptable salt thereof disclosed herein, the R$^Y$ is selected from the group consisting of H and C$_1$-C$_3$ alkyl, the C$_1$-C$_3$ alkyl is optionally substituted with one or more F, Cl, or Br.

In some embodiments of the compound of formula III or the pharmaceutically acceptable salt thereof disclosed herein, the R$^Y$ is selected from H.

In some embodiments of the compound of formula III or the pharmaceutically acceptable salt thereof disclosed herein, the R$^{X1}$ is selected from the group consisting of H, C$_1$-C$_4$ alkyl, F, Cl, Br, and C$_1$-C$_4$ alkyl substituted with F, Cl, or Br.

In some embodiments of the compound of formula III or the pharmaceutically acceptable salt thereof disclosed herein, the R$^{X1}$ is selected from H.

In some embodiments of the compound of formula III or the pharmaceutically acceptable salt thereof disclosed herein, the R$^{X2}$ is selected from the group consisting of H, —C(O)OH, —C(O)OCH$_3$, —C(O)OC$_2$H$_5$, —C(O)NH$_2$, —C(O)NHCH$_3$, —C(O)NHC$_2$H$_5$, —C(O)N(CH$_3$)$_2$, —C(O)N(C$_2$H$_5$)$_2$, and —C(O)NHCH$_2$CF$_3$.

In some embodiments of the compound of formula III or the pharmaceutically acceptable salt thereof disclosed herein, the R$^{X2}$ is selected from H.

In some embodiments of the compound of formula III or the pharmaceutically acceptable salt thereof disclosed herein, the R$^2$ and R$^3$ are each independently selected from the group consisting of C$_1$-C$_4$ alkyl, C$_2$-C$_4$ alkenyl, C$_2$-C$_4$ alkynyl, C$_1$-C$_4$ alkoxy, C$_1$-C$_4$ alkylamino, and (C$_1$-C$_4$ alkyl)$_2$ amino, the C$_1$-C$_4$ alkyl, C$_2$-C$_4$ alkenyl, C$_2$-C$_4$ alkynyl, C$_1$-C$_4$ alkoxy, C$_1$-C$_4$ alkylamino, or (C$_1$-C$_4$ alkyl)$_2$ amino is optionally substituted with one or more F, Cl, Br, hydroxyl, amino, nitro, or cyano; or R$^2$ and R$^3$ are connected and form a 4-6 membered heterocycloalkyl together with an adjacent S atom, the 4-6 membered heterocycloalkyl optionally contains 1-3 heteroatoms selected from the group consisting of N, O and S in addition to the S atom to which R$^2$ and R$^3$ are both connected; and the ring carbon atoms of the 4-6 membered heterocycloalkyl are optionally substituted with one or more F, Cl, Br, hydroxyl, amino, nitro, cyano, C$_1$-C$_4$ alkyl, C$_1$-C$_4$ haloalkyl, C$_1$-C$_4$ alkoxy, C$_1$-C$_4$ alkylamino, or (C$_1$-C$_4$ alkyl)$_2$ amino, or substituted with one or more oxo.

In some embodiments of the compound of formula III or the pharmaceutically acceptable salt thereof disclosed herein, the R$^2$ and R$^3$ are each independently selected from the group consisting of methyl, ethyl, propyl, and trifluoromethyl; or R$^2$ and R$^3$ are connected and form

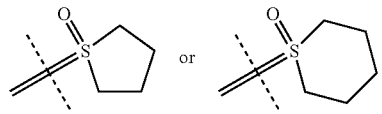

together with an adjacent =S=O.

In some embodiments of the compound of formula III or the pharmaceutically acceptable salt thereof disclosed herein, the L is selected from the group consisting of a single bond, —O—, —NH—, and —(C$_1$-C$_3$ alkyl)-O—.

In some embodiments of the compound of formula III or the pharmaceutically acceptable salt thereof disclosed herein, the L is selected from —O—.

In some embodiments of the compound of formula III or the pharmaceutically acceptable salt thereof disclosed herein, the R$^4$ is selected from the group consisting of phenyl, naphthyl, piperidinyl, pyridinyl, imidazolyl, pyrazolyl, pyrazinyl, piperazinyl, thienyl, furanyl, thiazolyl, isothiazolyl, oxazolyl, isoxazolyl, 1,4-dihydropyridinyl, and tetrahydrofuranyl; and R$^4$ is optionally substituted with one or more F, Cl, Br, cyano, methyl, ethyl, propyl, butyl, trifluoromethyl, methoxy, ethoxy, propoxy, methylamino, ethylamino, propylamino, (methyl)$_2$ amino, (ethyl)$_2$ amino, (propyl)$_2$ amino, —C(O)OH, —C(O)OCH$_3$, —C(O)OC$_2$H$_5$, —C(O)NH$_2$, —C(O)NHCH$_3$, —C(O)NHC$_2$H$_5$, —C(O)N(CH$_3$)$_2$, —C(O)N(C$_2$H$_5$)$_2$, acetyl, —S(O)$_2$CH$_3$, —S(O)$_2$C$_2$H$_5$, —NHS(O)$_2$CH$_3$, —NHS(O)$_2$C$_2$H$_5$, —S(O)$_2$NH$_2$, —S(O)$_2$NHCH$_3$, —S(O)$_2$NHC$_2$H$_5$, —S(O)$_2$N(CH$_3$)$_2$, or —S(O)$_2$N(C$_2$H$_5$)$_2$, or substituted with one or more oxo.

In some embodiments of the compound of formula III or the pharmaceutically acceptable salt thereof disclosed herein, the R$^4$ is selected from the group consisting of

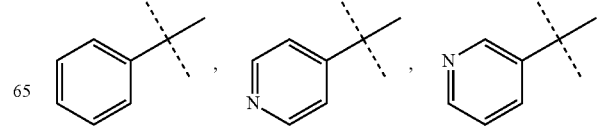

-continued

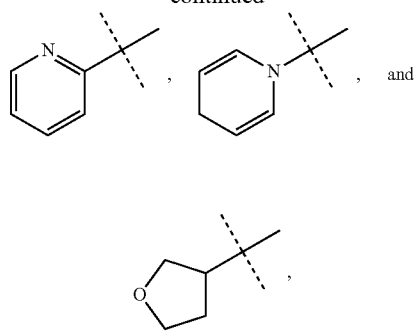

and R[4] is optionally substituted with one or more F, Cl, Br, cyano, methyl, ethyl, propyl, butyl, trifluoromethyl, methoxy, ethoxy, propoxy, methylamino, ethylamino, propylamino, (methyl)₂ amino, (ethyl)₂ amino, (propyl)₂ amino, —C(O)OH, —C(O)OCH₃, —C(O)OC₂H₅, —C(O)NH₂, —C(O)NHCH₃, —C(O)NHC₂H₅, —C(O)N(CH₃)₂, —C(O)N(C₂H₅)₂, acetyl, —S(O)₂CH₃, —S(O)₂C₂H₅, —NHS(O)₂CH₃, —NHS(O)₂C₂H₅, —S(O)₂NH₂, —S(O)₂NHCH₃, —S(O)₂NHC₂H₅, —S(O)₂N(CH₃)₂, or —S(O)₂N(C₂H₅)₂, or substituted with one or more oxo.

In some embodiments of the compound of formula III or the pharmaceutically acceptable salt thereof disclosed herein, the R⁴ is selected from the group consisting of

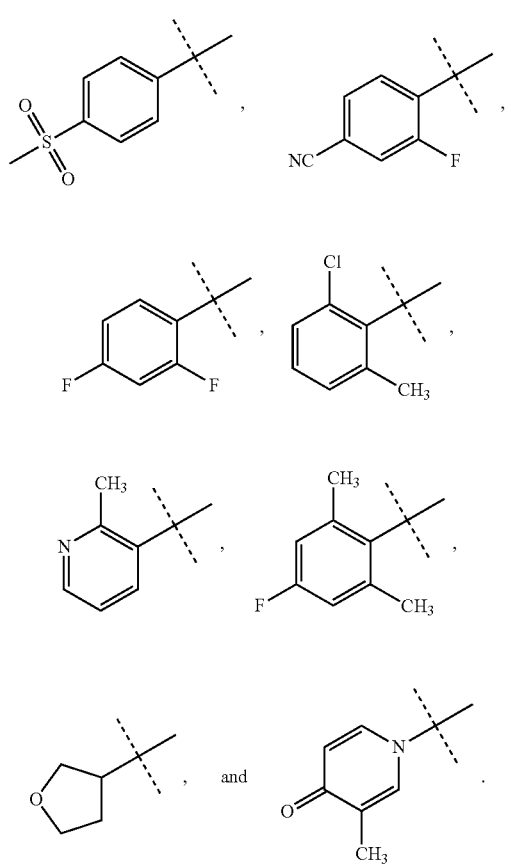

The present application provides a compound of formula IV or a pharmaceutically acceptable salt thereof,

IV

Wherein, R¹ is selected from the group consisting of H, C₁-C₃ alkyl, and C₁-C₃ acyl, the C₁-C₃ alkyl or C₁-C₃ acyl is optionally substituted with one or more halogens;

R$^Y$ is selected from the group consisting of H, C₁-C₃ alkyl, and C₁-C₃ acyl, the C₁-C₃ alkyl or C₁-C₃ acyl is optionally substituted with one or more halogens;

R$^{X1}$ is selected from the group consisting of H, C₁-C₆ alkyl, halogen, and C₁-C₆ haloalkyl; R$^{X2}$ is selected from the group consisting of H, halogen, C₁-C₆ alkyl, C₂-C₆ alkenyl, C₂-C₆ alkynyl, —C(O)OR$^a$, —C(O)NR$^b$R$^c$, —C(O)R$^d$, —S(O)₂R$^e$, and —S(O)₂NR$^b$R$^c$, the C₁-C₆ alkyl, C₂-C₆ alkenyl, or C₂-C₆ alkynyl is optionally substituted with one or more halogens, hydroxyl, amino, nitro, or cyano;

R² and R³ are each independently selected from the group consisting of halogen, hydroxyl, C₁-C₆ alkyl, C₂-C₆ alkenyl, C₂-C₆ alkynyl, C₁-C₆ alkoxy, C₁-C₆ alkylamino, and (C₁-C₆ alkyl)₂ amino, the C₁-C₆ alkyl, C₂-C₆ alkenyl, C₂-C₆ alkynyl, C₁-C₆ alkoxy, C₁-C₆ alkylamino, or (C₁-C₆ alkyl)₂ amino is optionally substituted with one or more halogens, hydroxyl, amino, nitro, or cyano; or R² and R³ are connected and form a 3-8 membered heterocycloalkyl together with an adjacent S atom, the 3-8 membered heterocycloalkyl optionally contains 1-3 heteroatoms selected from the group consisting of N, O, and S, in addition to the S atom to which R² and R³ are both connected; and the ring carbon atoms of the 3-8 membered heterocycloalkyl are optionally substituted with one or more halogens, hydroxyl, amino, nitro, cyano, C₁-C₆ alkyl, C₁-C₆ haloalkyl, C₁-C₆ alkoxy, C₁-C₆ alkylamino, or (C₁-C₆ alkyl)₂ amino, or substituted with one or more oxo;

L is selected from the group consisting of a single bond, —O—, —NH—, —(C₁-C₃ alkyl)-O—, —(C₁-C₃ alkyl)-NH—, and —C₁-C₃ alkyl-; and R⁴ is selected from the group consisting of C₆-C₁₀ aryl, C₃-C₁₀ cycloalkenyl, C₃-C₁₀ cycloalkyl, 3-10 membered heteroaryl, 3-10 membered heterocycloalkenyl, and 3-10 membered heterocycloalkyl, the 3-10 membered heteroaryl, 3-10 membered heterocycloalkenyl, or 3-10 membered heterocycloalkyl each independently contains 1-3 heteroatoms selected from the group consisting of N, O, and S; and R⁴ is optionally substituted with one or more halogens, hydroxyl, amino, nitro, cyano, C₁-C₆ alkyl, C₁-C₆ haloalkyl, C₁-C₆ alkoxy, C₁-C₆ alkylamino, (C₁-C₆ alkyl)₂ amino, —C(O)OR$^a$, —C(O)NR$^b$R$^c$, —C(O)R$^d$, —S(O)₂R$^e$, —NHS(O)₂R$^e$, or —S(O)₂NR$^b$R$^c$, or substituted with one or more oxo;

the R$^a$, R$^b$, R$^c$, R$^d$, and R$^e$ are each independently selected from the group consisting of H, C₁-C₆ alkyl, and C₁-C₆ haloalkyl.

In some embodiments of the compound of formula V or the pharmaceutically acceptable salt thereof disclosed herein, the $R^1$ is selected from the group consisting of H and $C_1$-$C_3$ alkyl, the $C_1$-$C_3$ alkyl is optionally substituted with one or more F, Cl, or Br.

In some embodiments of the compound of formula V or the pharmaceutically acceptable salt thereof disclosed herein, the $R^1$ is selected from the group consisting of H, methyl, ethyl, propyl, and trifluoromethyl.

In some embodiments of the compound of formula IV or the pharmaceutically acceptable salt thereof disclosed herein, the $R^Y$ is selected from the group consisting of H and $C_1$-$C_3$ alkyl, the $C_1$-$C_3$ alkyl is optionally substituted with one or more F, Cl, or Br.

In some embodiments of the compound of formula IV or the pharmaceutically acceptable salt thereof disclosed herein, the $R^Y$ is selected from H.

In some embodiments of the compound of formula V or the pharmaceutically acceptable salt thereof disclosed herein, the $R^{X1}$ is selected from the group consisting of H, $C_1$-$C_4$ alkyl, F, Cl, Br, and $C_1$-$C_4$ alkyl substituted with F, Cl, or Br.

In some embodiments of the compound of formula V or the pharmaceutically acceptable salt thereof disclosed herein, the $R^{X1}$ is selected from H.

In some embodiments of the compound of formula IV or the pharmaceutically acceptable salt thereof disclosed herein, the $R^{X2}$ is selected from the group consisting of H, —C(O)OH, —C(O)OCH$_3$, —C(O)OC$_2$H$_5$, —C(O)NH$_2$, —C(O)NHCH$_3$, —C(O)NHC$_2$H$_5$, —C(O)N(CH$_3$)$_2$, —C(O)N(C$_2$H$_5$)$_2$, and —C(O)NHCH$_2$CF$_3$.

In some embodiments of the compound of formula V or the pharmaceutically acceptable salt thereof disclosed herein, the $R^{X2}$ is selected from H.

In some embodiments of the compound of formula IV or the pharmaceutically acceptable salt thereof disclosed herein, the $R^2$ and $R^3$ are each independently selected from the group consisting of $C_1$-$C_4$ alkyl, $C_2$-$C_4$ alkenyl, $C_2$-$C_4$ alkynyl, $C_1$-$C_4$ alkoxy, $C_1$-$C_4$ alkylamino, and ($C_1$-$C_4$ alkyl)$_2$ amino, the $C_1$-$C_4$ alkyl, $C_2$-$C_4$ alkenyl, $C_2$-$C_4$ alkynyl, $C_1$-$C_4$ alkoxy, $C_1$-$C_4$ alkylamino, or ($C_1$-$C_4$ alkyl)$_2$ amino is optionally substituted with one or more F, Cl, Br, hydroxyl, amino, nitro, or cyano; or $R^2$ and $R^3$ are connected and form a 4-6 membered heterocycloalkyl together with an adjacent S atom, the 4-6 membered heterocycloalkyl optionally contains 1-3 heteroatoms selected from the group consisting of N, O and S, in addition to the S atom to which $R^2$ and $R^3$ are both connected; and the ring carbon atoms of the 4-6 membered heterocycloalkyl are optionally substituted with one or more F, Cl, Br, hydroxyl, amino, nitro, cyano, $C_1$-$C_4$ alkyl, $C_1$-$C_4$ haloalkyl, $C_1$-$C_4$ alkoxy, $C_1$-$C_4$ alkylamino, or ($C_1$-$C_4$ alkyl)$_2$ amino, or substituted with one or more oxo.

In some embodiments of the compound of formula V or the pharmaceutically acceptable salt thereof disclosed herein, the $R^2$ and $R^3$ are each independently selected from the group consisting of methyl, ethyl, propyl, and trifluoromethyl; or $R^2$ and $R^3$ are connected and form

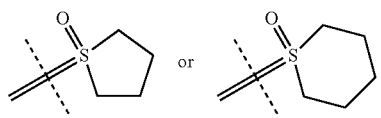

together with an adjacent =S=O.

In some embodiments of the compound of formula V or the pharmaceutically acceptable salt thereof disclosed herein, the L is selected from the group consisting of a single bond, —O—, —NH—, and —($C_1$-$C_3$ alkyl)-O—.

In some embodiments of the compound of formula V or the pharmaceutically acceptable salt thereof disclosed herein, the L is selected from —O—.

In some embodiments of the compound of formula V or the pharmaceutically acceptable salt thereof disclosed herein, the $R^4$ is selected from the group consisting of phenyl, naphthyl, piperidinyl, pyridinyl, imidazolyl, pyrazolyl, pyrazinyl, piperazinyl, thienyl, furanyl, thiazolyl, isothiazolyl, oxazolyl, isoxazolyl, 1,4-dihydropyridinyl, and tetrahydrofuranyl; and $R^4$ is optionally substituted with one or more F, Cl, Br, cyano, methyl, ethyl, propyl, butyl, trifluoromethyl, methoxy, ethoxy, propoxy, methylamino, ethylamino, propylamino, (methyl)$_2$ amino, (ethyl)$_2$ amino, (propyl)$_2$ amino, —C(O)OH, —C(O)OCH$_3$, —C(O)OC$_2$H$_5$, —C(O)NH$_2$, —C(O)NHCH$_3$, —C(O)NHC$_2$H$_5$, —C(O)N(CH$_3$)$_2$, —C(O)N(C$_2$H$_5$)$_2$, acetyl, —S(O)$_2$CH$_3$, —S(O)$_2$C$_2$H$_5$, —NHS(O)$_2$CH$_3$, —NHS(O)$_2$C$_2$H$_5$, —S(O)$_2$NH$_2$, —S(O)$_2$NHCH$_3$, —S(O)$_2$NHC$_2$H$_5$, —S(O)$_2$N(CH$_3$)$_2$, or —S(O)$_2$N(C$_2$H$_5$)$_2$, or substituted with one or more oxo.

In some embodiments of the compound of formula IV or the pharmaceutically acceptable salt thereof disclosed herein the $R^4$ is selected from the group consisting of

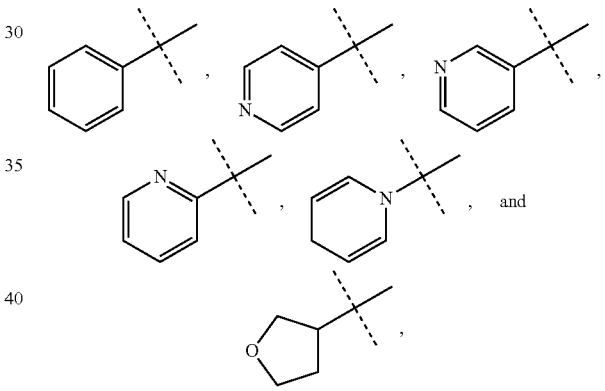

and $R^4$ is optionally substituted with one or more F, Cl, Br, cyano, methyl, ethyl, propyl, butyl, trifluoromethyl, methoxy, ethoxy, propoxy, methylamino, ethylamino, propylamino, (methyl)$_2$ amino, (ethyl)$_2$ amino, (propyl)$_2$ amino, —C(O)OH, —C(O)OCH$_3$, —C(O)OC$_2$H$_5$, —C(O)NH$_2$, —C(O)NHCH$_3$, —C(O)NHC$_2$H$_5$, —C(O)N(CH$_3$)$_2$, —C(O)N(C$_2$H$_5$)$_2$, acetyl, —S(O)$_2$CH$_3$, —S(O)$_2$C$_2$H$_5$, —NHS(O)$_2$CH$_3$, —NHS(O)$_2$C$_2$H$_5$, —S(O)$_2$NH$_2$, —S(O)$_2$NHCH$_3$, —S(O)$_2$NHC$_2$H$_5$, —S(O)$_2$N(CH$_3$)$_2$, or —S(O)$_2$N(C$_2$H$_5$)$_2$, or substituted with one or more oxo.

In some embodiments of the compound of formula V or the pharmaceutically acceptable salt thereof disclosed herein, the $R^4$ is selected from the group consisting of

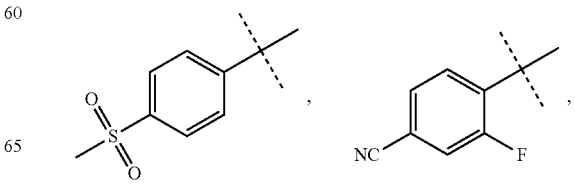

-continued

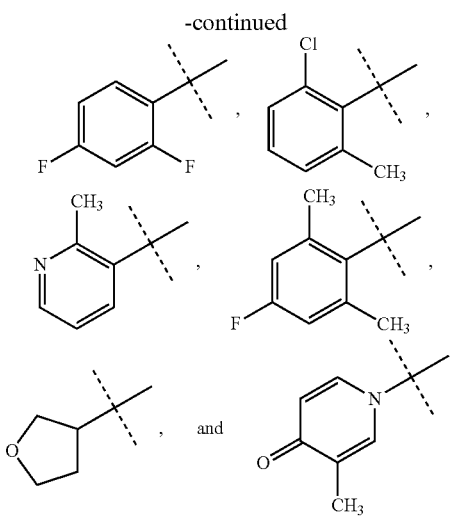

The present application provides a compound of formula V or a pharmaceutically acceptable salt thereof,

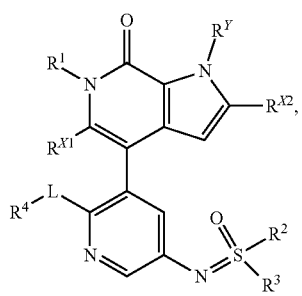

wherein, $R^1$ is selected from the group consisting of H, $C_1$-$C_3$ alkyl, and $C_1$-$C_3$ acyl, the $C_1$-$C_3$ alkyl or $C_1$-$C_3$ acyl is optionally substituted with one or more halogens;

$R^Y$ is selected from the group consisting of H, $C_1$-$C_3$ alkyl, and $C_1$-$C_3$ acyl, the $C_1$-$C_3$ alkyl or $C_1$-$C_3$ acyl is optionally substituted with one or more halogens;

$R^{X1}$ is selected from the group consisting of H, $C_1$-$C_6$ alkyl, halogen, and $C_1$-$C_6$ haloalkyl;

$R^{X2}$ is selected from the group consisting of H, halogen, $C_1$-$C_6$ alkyl, $C_2$-$C_6$ alkenyl, $C_2$-$C_6$ alkynyl, —C(O)OR$^a$, —C(O)NR$^b$R$^c$, —C(O)R$^d$, —S(O)$_2$R$^e$, and —S(O)$_2$NR$^b$R$^c$, the $C_1$-$C_6$ alkyl, $C_2$-$C_6$ alkenyl, or $C_2$-$C_6$ alkynyl is optionally substituted with one or more halogens, hydroxyl, amino, nitro, or cyano;

$R^2$ and $R^3$ are each independently selected from the group consisting of halogen, hydroxyl, $C_1$-$C_6$ alkyl, $C_2$-$C_6$ alkenyl, $C_2$-$C_6$ alkynyl, $C_1$-$C_6$ alkoxy, $C_1$-$C_6$ alkylamino, and ($C_1$-$C_6$ alkyl)$_2$ amino, the $C_1$-$C_6$ alkyl, $C_2$-$C_6$ alkenyl, $C_2$-$C_6$ alkynyl, $C_1$-$C_6$ alkoxy, $C_1$-$C_6$ alkylamino, or ($C_1$-$C_6$ alkyl)$_2$ amino is optionally substituted with one or more halogens, hydroxyl, amino, nitro, or cyano; or $R^2$ and $R^3$ are connected and form a 3-8 membered heterocycloalkyl together with an adjacent S atom, the 3-8 membered heterocycloalkyl optionally contains 1-3 heteroatoms selected from the group consisting of N, O, and S, in addition to the S atom to which $R^2$ and $R^3$ are both connected; and the ring carbon atoms of the 3-8 membered heterocycloalkyl are optionally substituted with one or more halogens, hydroxyl, amino, nitro, cyano, $C_1$-$C_6$ alkyl, $C_1$-$C_6$ haloalkyl, $C_1$-$C_6$ alkoxy, $C_1$-$C_6$ alkylamino, or ($C_1$-$C_6$ alkyl)$_2$ amino, or substituted with one or more oxo;

L is selected from the group consisting of a single bond, —O—, —NH—, —($C_1$-$C_3$ alkyl)-O—, —($C_1$-$C_3$ alkyl)-NH—, and —$C_1$-$C_3$ alkyl-; and $R^4$ is selected from the group consisting of $C_6$-$C_{10}$ aryl, $C_3$-$C_{10}$ cycloalkenyl, $C_3$-$C_{10}$ cycloalkyl, 3-10 membered heteroaryl, 3-10 membered heterocycloalkenyl, and 3-10 membered heterocycloalkyl, the 3-10 membered heteroaryl, 3-10 membered heterocycloalkenyl, or 3-10 membered heterocycloalkyl each independently contains 1-3 heteroatoms selected from the group consisting of N, O, and S; and $R^4$ is optionally substituted with one or more halogens, hydroxyl, amino, nitro, cyano, $C_1$-$C_6$ alkyl, $C_1$-$C_6$ haloalkyl, $C_1$-$C_6$ alkoxy, $C_1$-$C_6$ alkylamino, ($C_1$-$C_6$ alkyl)$_2$ amino, —C(O)OR$^a$, —C(O)NR$^b$R$^c$, —C(O)R$^d$, —S(O)$_2$R$^e$, —NHS(O)$_2$R$^e$, or —S(O)$_2$NR$^b$R$^c$, or substituted with one or more oxo;

the R$^a$, R$^b$, R$^c$, R$^d$, and R$^e$ are each independently selected from the group consisting of H, $C_1$-$C_6$ alkyl, and $C_1$-$C_6$ haloalkyl.

In some embodiments of the compound of formula V or the pharmaceutically acceptable salt thereof disclosed herein, the $R^1$ is selected from the group consisting of H and $C_1$-$C_3$ alkyl, the $C_1$-$C_3$ alkyl is optionally substituted with one or more F, Cl, or Br.

In some embodiments of the compound of formula V or the pharmaceutically acceptable salt thereof disclosed herein, the $R^1$ is selected from the group consisting of H, methyl, ethyl, propyl, and trifluoromethyl.

In some embodiments of the compound of formula V or the pharmaceutically acceptable salt thereof disclosed herein, the $R^Y$ is selected from the group consisting of H and $C_1$-$C_3$ alkyl, the $C_1$-$C_3$ alkyl is optionally substituted with one or more F, Cl, or Br.

In some embodiments of the compound of formula V or the pharmaceutically acceptable salt thereof disclosed herein, the $R^Y$ is selected from H.

In some embodiments of the compound of formula V or the pharmaceutically acceptable salt thereof disclosed herein, the $R^{X1}$ is selected from the group consisting of H, $C_1$-$C_4$ alkyl, F, Cl, Br, and $C_1$-$C_4$ alkyl substituted with F, Cl, or Br.

In some embodiments of the compound of formula V or the pharmaceutically acceptable salt thereof disclosed herein, the $R^{X1}$ is selected from H.

In some embodiments of the compound of formula V or the pharmaceutically acceptable salt thereof disclosed herein, the $R^{X2}$ is selected from the group consisting of H, —C(O)OH, —C(O)OCH$_3$, —C(O)OC$_2$H$_5$, —C(O)NH$_2$, —C(O)NHCH$_3$, —C(O)NHC$_2$H$_5$, —C(O)N(CH$_3$)$_2$, —C(O)N(C$_2$H$_5$)$_2$, and —C(O)NHCH$_2$CF$_3$.

In some embodiments of the compound of formula V or the pharmaceutically acceptable salt thereof disclosed herein, the $R^{X2}$ is selected from the group consisting of H, —C(O)NH$_2$, —C(O)NHCH$_3$, —C(O)NHC$_2$H$_5$, —C(O)N(CH$_3$)$_2$, and —C(O)N(C$_2$H$_5$)$_2$.

In some embodiments of the compound of formula V or the pharmaceutically acceptable salt thereof disclosed herein, the $R^2$ and $R^3$ are each independently selected from the group consisting of $C_1$-$C_4$ alkyl, $C_2$-$C_4$ alkenyl, $C_2$-$C_4$ alkynyl, $C_1$-$C_4$ alkoxy, $C_1$-$C_4$ alkylamino, and ($C_1$-$C_4$ alkyl)$_2$ amino, the $C_1$-$C_4$ alkyl, $C_2$-$C_4$ alkenyl, $C_2$-$C_4$ alkynyl, $C_1$-$C_4$ alkoxy, $C_1$-$C_4$ alkylamino, or ($C_1$-$C_4$ alkyl)$_2$ amino is optionally substituted with one or more F, Cl, Br, hydroxyl, amino, nitro, or cyano; or $R^2$ and $R^3$ are connected and form a 4-6 membered heterocycloalkyl together with an adjacent S atom, the 4-6 membered heterocycloalkyl optionally contains 1-3 heteroatoms selected from the group consisting of N, O and S, in addition to the S atom to which $R^2$ and $R^3$ are both connected; and the ring carbon atoms of the 4-6 membered heterocycloalkyl are optionally substituted with one or more F, Cl, Br, hydroxyl, amino, nitro, cyano, $C_1$-$C_4$ alkyl, $C_1$-$C_4$ haloalkyl, $C_1$-$C_4$ alkoxy, $C_1$-$C_4$ alkylamino, or ($C_1$-$C_4$ alkyl)$_2$ amino, or substituted with one or more oxo.

In some embodiments of the compound of formula V or the pharmaceutically acceptable salt thereof disclosed herein, the $R^2$ and $R^3$ are each independently selected from the group consisting of methyl, ethyl, propyl, and trifluoromethyl; or $R^2$ and $R^3$ are connected and form

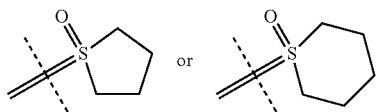

together with an adjacent =S=O.

In some embodiments of the compound of formula V or the pharmaceutically acceptable salt thereof disclosed herein, the L is selected from the group consisting of a single bond, —O—, —NH—, and —($C_1$-$C_3$ alkyl)-O—.

In some embodiments of the compound of formula V or the pharmaceutically acceptable salt thereof disclosed herein, the L is selected from —O—.

In some embodiments of the compound of formula V or the pharmaceutically acceptable salt thereof disclosed herein, $R^4$ is selected from the group consisting of phenyl, naphthyl, piperidinyl, pyridinyl, imidazolyl, pyrazolyl, pyrazinyl, piperazinyl, thienyl, furanyl, thiazolyl, isothiazolyl, oxazolyl, isoxazolyl, 1,4-dihydropyridinyl, and tetrahydrofuranyl; and $R^4$ is optionally substituted with one or more F, Cl, Br, cyano, methyl, ethyl, propyl, butyl, trifluoromethyl, methoxy, ethoxy, propoxy, methylamino, ethylamino, propylamino, (methyl)$_2$ amino, (ethyl)$_2$ amino, (propyl)$_2$ amino, —C(O)OH, —C(O)OCH$_3$, —C(O)OC$_2$H$_5$, —C(O)NH$_2$, —C(O)NHCH$_3$, —C(O)NHC$_2$H$_5$, —C(O)N(CH$_3$)$_2$, —C(O)N(C$_2$H$_5$)$_2$, acetyl, —S(O)$_2$CH$_3$, —S(O)$_2$C$_2$H$_5$, —NHS(O)$_2$CH$_3$, —NHS(O)$_2$C$_2$H$_5$, —S(O)$_2$NH$_2$, —S(O)$_2$NHCH$_3$, —S(O)$_2$NHC$_2$H$_5$, —S(O)$_2$N(CH$_3$)$_2$, or —S(O)$_2$N(C$_2$H$_5$)$_2$, or substituted with one or more oxo.

In some embodiments of the compound of formula V or the pharmaceutically acceptable salt thereof disclosed herein, the $R^4$ is selected from the group consisting of

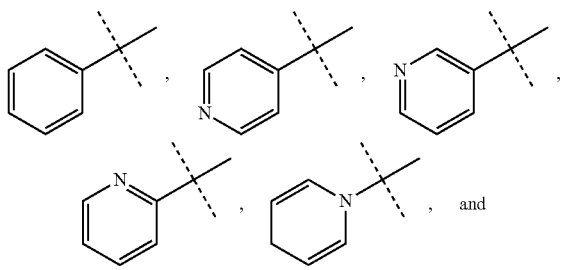

-continued

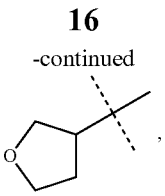

and $R^4$ is optionally substituted with one or more F, Cl, Br, cyano, methyl, ethyl, propyl, butyl, trifluoromethyl, methoxy, ethoxy, propoxy, methylamino, ethylamino, propylamino, (methyl)$_2$ amino, (ethyl)$_2$ amino, (propyl)$_2$ amino, —C(O)OH, —C(O)OCH$_3$, —C(O)OC$_2$H$_5$, —C(O)NH$_2$, —C(O)NHCH$_3$, —C(O)NHC$_2$H$_5$, —C(O)N(CH$_3$)$_2$, —C(O)N(C$_2$H$_5$)$_2$, acetyl, —S(O)$_2$CH$_3$, —S(O)$_2$C$_2$H$_5$, —NHS(O)$_2$CH$_3$, —NHS(O)$_2$C$_2$H$_5$, —S(O)$_2$NH$_2$, —S(O)$_2$NHCH$_3$, —S(O)$_2$NHC$_2$H$_5$, —S(O)$_2$N(CH$_3$)$_2$, or —S(O)$_2$N(C$_2$H$_5$)$_2$, or substituted with one or more oxo.

In some embodiments of the compound of formula V or the pharmaceutically acceptable salt thereof disclosed herein, the $R^4$ is selected from the group consisting of

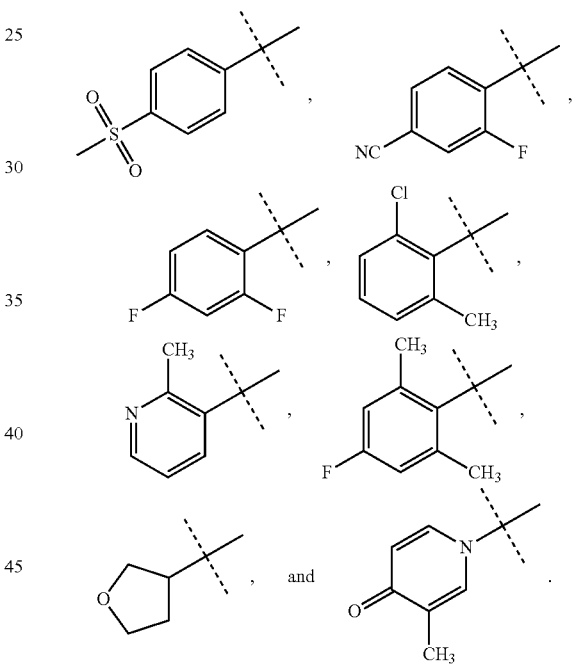

The present application provides the following compounds or the pharmaceutically acceptable salts thereof,

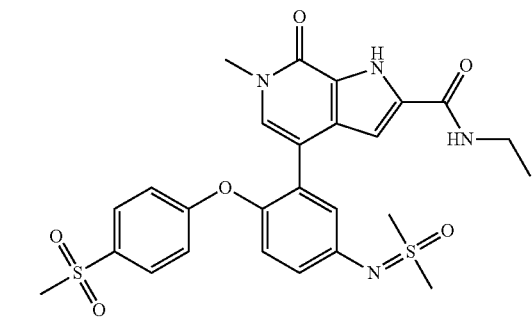 [SMILES: CCNC(=O)c1cc2c(-c3cc(N=S(C)(C)=O)ccc3Oc3ccc(S(C)(=O)=O)cc3)cn(C)c(=O)c2[nH]1]

-continued
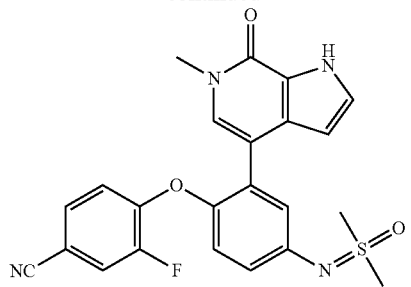
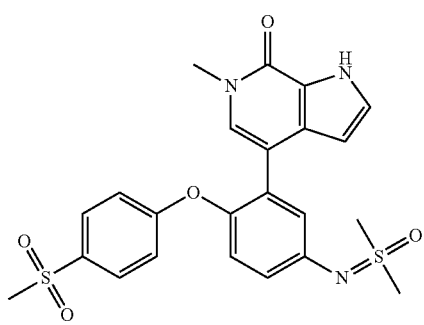
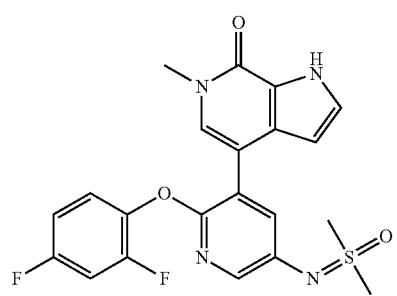
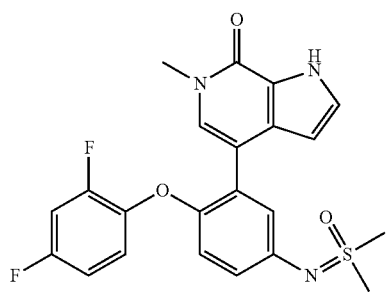
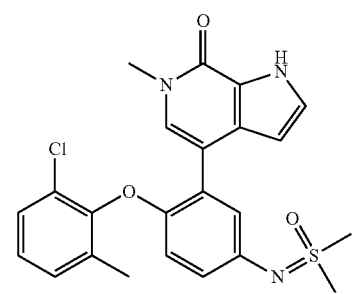
-continued
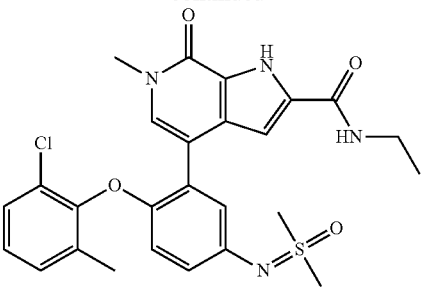
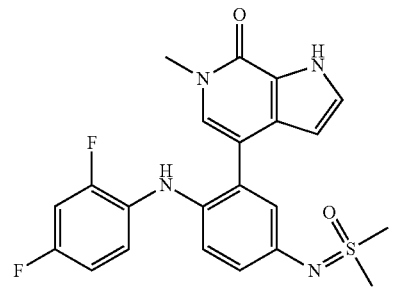
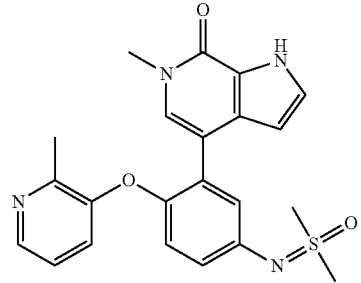
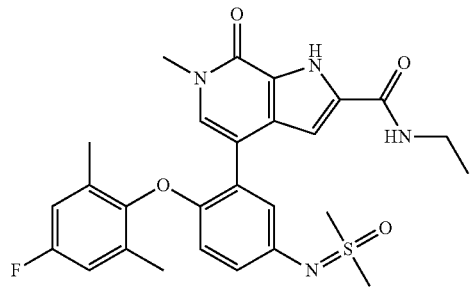
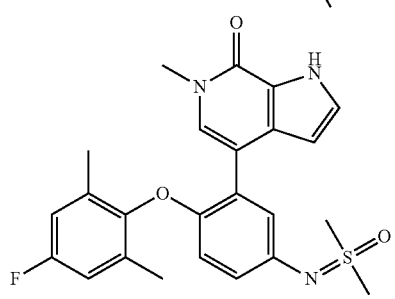
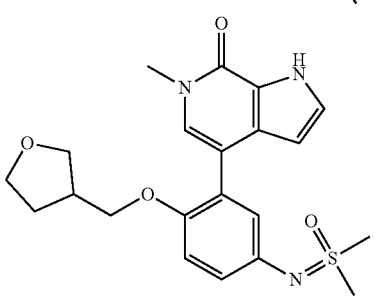

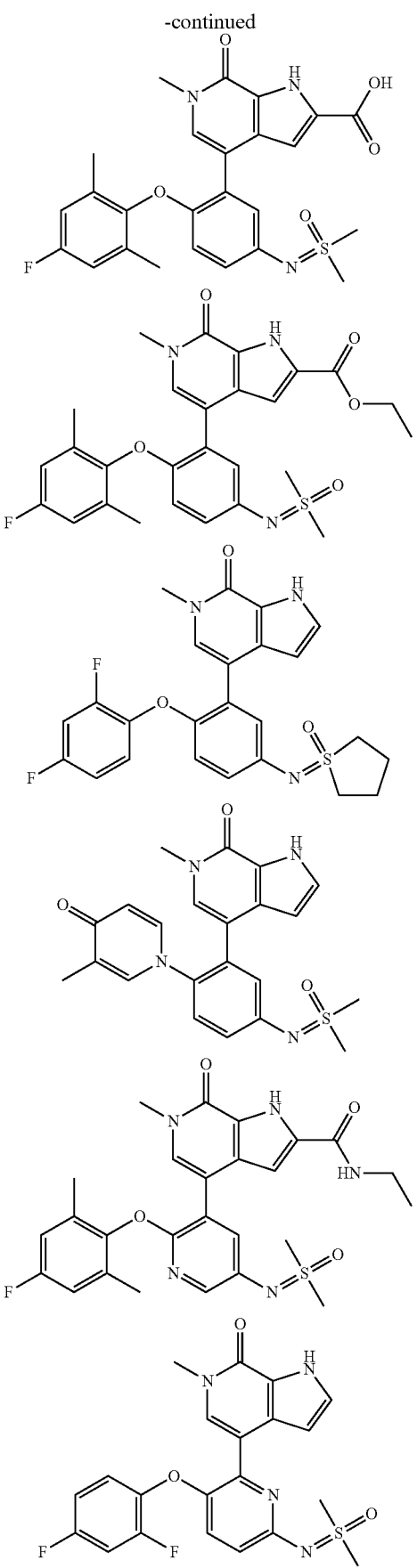
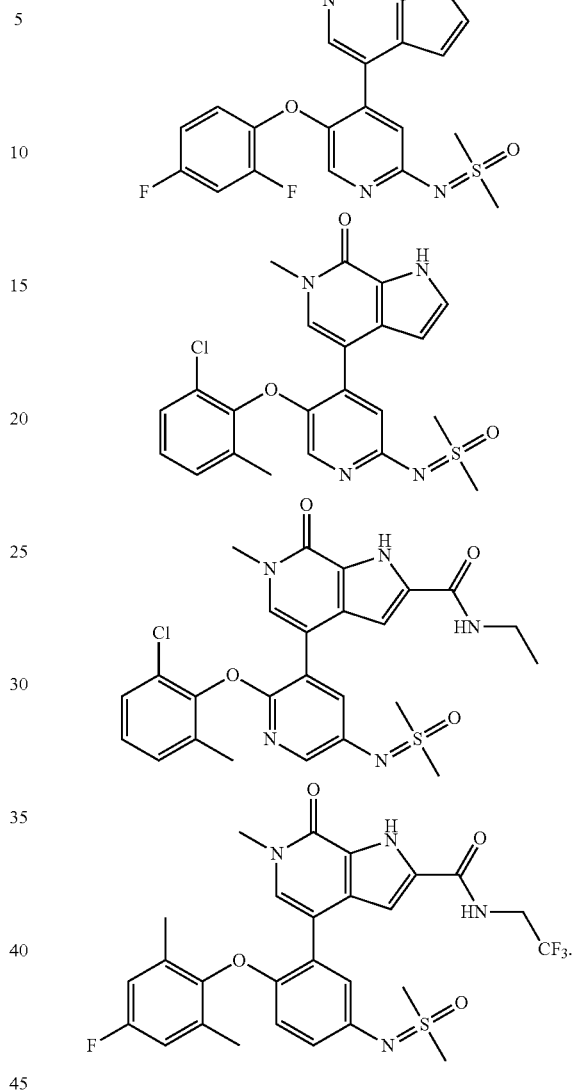

In another aspect, the present application relates to a pharmaceutical composition comprising the compound or the pharmaceutically acceptable salt thereof disclosed herein. In some embodiments, the pharmaceutical composition disclosed herein further comprises a pharmaceutically acceptable excipient.

In another aspect, the present application relates to a method for treating a disease mediated by BET protein in a mammal, comprising administering to the mammal (preferably a human) in need thereof a therapeutically effective amount of the compound or the pharmaceutically acceptable salt thereof, or the pharmaceutical composition thereof disclosed herein.

In another aspect, the present application relates to use of the compound or the pharmaceutically acceptable salt thereof, or the pharmaceutical composition thereof disclosed herein, in preparation of a medicament for treating a disease mediated by BET protein.

In some embodiments of the present application, the disease mediated by BET protein is selected from cancer. Preferably, the cancer is selected from the group consisting of solid tumor and hematological tumor. More preferably, the solid tumor is selected from the group consisting of breast cancer and prostate cancer. More preferably, the hematological tumor is selected from the group consisting of acute myelogenous leukemia, multiple myeloma, and diffuse large B-cell lymphoma.

Definitions

Unless otherwise stated, the following terms used in the present application shall have the following meanings. A specific term, unless otherwise specifically defined, should not be considered uncertain or unclear, but construed according to its common meaning in the field. When referring to a trade name, it is intended to refer to its corresponding commercial product or its active ingredient.

The term "substituted" means that any one or more hydrogen atoms on a specific atom are substituted by substituents, as long as the valence of the specific atom is normal and the resulting compound is stable. When the substituent is oxo (namely =O), it means that two hydrogen atoms are substituted, and oxo is not available on an aromatic group.

The terms "optional" or "optionally" means that the subsequently described event or circumstance may, but not necessarily, occur. The description includes instances where the event or circumstance occurs and instances where it does not. For example, an ethyl optionally substituted by halogen, means that the ethyl may be unsubstituted ($CH_2CH_3$), monosubstituted (for example, $CH_2CH_2F$), polysubstituted (for example, $CHFCH_2F$, $CH_2CHF_2$ and the like) or fully substituted ($CF_2CF_3$). It will be understood by a person skilled in the art that for any groups comprising one or more substituents, any substitutions or substituting patterns which may not exist or cannot be synthesized spatially are not introduced. It will be understood by a person skilled in the art that when a group is substituted with multiple substituents, the number of the substituents may be 2, 3, 4, 5 or more, up to all the sites where substitution can occur being substituted. For example, when ethyl is substituted with multiple F atoms, the number of the F atom may be 2, 3, 4 or 5.

"$C_{m-n}$" used herein means that the portion has an integer number of carbon atoms in the given range. For example, "$C_{1-6}$" means that the group may have 1 carbon atom, 2 carbon atoms, 3 carbon atoms, 4 carbon atoms, 5 carbon atoms or 6 carbon atoms.

When any variable (e.g., R) occurs more than once in the constitution or structure of a compound, the definition of the variable in each case is independent. Therefore, for example, if a group is substituted by 2 R, the definition of each R is independent.

When a variable is a covalent bond, it means that the two groups connected thereto are directly connected. For example, in A-L-Z, when L represents a covalent bond, it means that the structure is actually A-Z.

The term "halo-" or "halogen" refers to fluorine, chlorine, bromine and iodine.

The term "hydroxyl" refers to —OH group.
The term "cyano" refers to —CN group.
The term "amino" refers to —$NH_2$ group.
The term "nitro" refers to —$NO_2$ group.
The term "alkyl" refers to hydrocarbyl with a general formula of $C_nH_{2n+1}$. The alkyl can be linear or branched. For example, the term "$C_{1-6}$ alkyl" refers to alkyl with 1-6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). The alkyl moiety (namely alkyl) of alkoxy, alkylamino, dialkylamino, alkylsulfonyl and alkylthio is similarly defined as above.

The term "alkoxyl" refers to —O-alkyl.
The term "alkylamino" refers to—NH-alkyl.
The term "dialkylamino" refers to —N(alkyl)$_2$.

The term "alkenyl" refers to linear or branched unsaturated aliphatic hydrocarbyl consisting of carbon atoms and hydrogen atoms with at least one double bond. Non-limiting examples of alkenyl include, but are not limited to, ethenyl, 1-propenyl, 2-propenyl, 1-butenyl, isobutenyl, 1,3-butadienyl, and the like.

The term "alkynyl" refers to linear or branched unsaturated aliphatic hydrocarbyl consisting of carbon atoms and hydrogen atoms with at least one triple bond. Non-limiting examples of alkynyl include, but not limited to, ethynyl (—C≡CH), 1-propinyl (—C≡C—$CH_3$), 2-propinyl (—$CH_2$—C≡CH), 1,3-butadiynyl (—C≡C—C≡CH), and the like.

The term "cycloalkyl" refers to a carbon ring that is fully saturated and may exist as a monocyclic, bridged cyclic or spiro structure. Unless otherwise specified, the carbon ring is generally a 3-10 membered ring. Non-limiting examples of cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl, and the like.

The term "cycloalkenyl" refers to a non-aromatic carbon ring that is not fully saturated and may exist as a monocyclic, bridged cyclic or spiro structure. Unless otherwise specified, the carbon ring is generally a 5-8 membered ring. Non-limiting examples of cycloalkenyl include, but are not limited to, cyclopentenyl, cyclopentadienyl, cyclohexenyl, cyclohexadienyl, cycloheptenyl, cycloheptadienyl, and the like.

The term "heterocycloalkenyl" refers to the above cycloalkenyl containing 1-3 heteroatoms (preferably 1 or 2 heteroatoms) independently selected from the group consisting of sulfur, oxygen, and/or nitrogen.

The term "heterocycloalkyl" refers to a cyclic group that is fully saturated and may exist as a monocyclic, bridged cyclic or spiro structure. Unless otherwise specified, the heterocyclyl is usually a 3-7 membered ring containing 1-3 heteroatoms (preferably 1 or 2 heteroatoms) independently selected from the group consisting of sulfur, oxygen and/or nitrogen. Examples of 3 membered heterocycloalkyl include, but are not limited to, oxiranyl, thiiranyl, and aziranyl. Non-limiting examples of 4 membered heterocycloalkyl include, but are not limited to, azetidinyl, oxetanyl, thietanyl. Examples of 5 membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, and tetrahydropyrazolyl. Examples of 6 membered heterocycloalkyl include, but are not limited to, piperidinyl, tetrahydropyranyl, tetrahydrothiopyranyl, morpholinyl, piperazinyl, 1,4-thioxanyl, 1,4-dioxanyl, thiomorpholinyl, 1,3-dithianyl, and 1,4-dithianyl. Examples of 7 membered heterocycloalkyl include, but are not limited to, azacycloheptanyl, oxacycloheptanyl, and thiepanyl. Preferably, the heterocycloalkyl is a monocyclic heterocycloalkyl with 5 or 6 ring atoms.

The term "aryl" refers to a monocyclic or fused polycyclic aromatic cyclic group of carbon atoms with the conjugated π electronic system. For example, an aryl may have 6-20 carbon atoms, 6-14 carbon atoms or 6-12 carbon atoms. Non-limiting examples of aryl includes, but are not limited to, phenyl, naphthyl, anthryl, 1,2,3,4-tetrahydronaphthalenyl, and the like.

The term "heteroaryl" refers to a monocyclic or fused polycyclic system which comprises at least one ring atom selected from the group consisting of N, O and S, with the remaining ring atoms being C, and which has at least one aromatic ring. Preferably, the heteroaryl has a single 4-8 membered ring, in particular, a 5-8 membered ring, or a plurality of fused rings comprising 6-14 ring atoms, in particular 6-10 ring atoms. Non-limiting examples of heteroaryl include, but are not limited to, pyrrolyl, furanyl, thienyl, imidazolyl, oxazolyl, pyrazolyl, pyridinyl, pyrimidinyl, pyrazinyl, quinolyl, isoquinolyl, tetrazolyl, triazolyl, triazinyl, benzofuranyl, benzothienyl, indolyl, isoindolyl and the like.

The term "treating" means administering the compound or formulation disclosed herein to prevent, ameliorate or eliminate a disease or one or more symptoms associated with the disease, and includes:
  (i) preventing the occurrence of the disease or disease state in a mammal, particularly when such a mammal is predisposed to the disease state but has not yet been diagnosed as having it;
  (ii) inhibiting a disease or disease state, i.e., arresting its development; and
  (iii) alleviating a disease or disease state, i.e., causing its regression.

The term "therapeutically effective amount" refers to an amount of the compound disclosed herein for (i) treating or preventing a specific disease, condition or disorder; (ii) alleviating, improving or eliminating one or more symptoms of a specific disease, condition or disorder, or (iii) preventing or delaying onset of one or more symptoms of a specific disease, condition or disorder described herein. The amount of the compound disclosed herein composing the "therapeutically effective amount" varies dependently on the compound, the disease state and its severity, the administration regimen, and the age of the mammal to be treated, but can be determined routinely by a person skilled in the art in accordance with their knowledge and the present disclosure.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

A pharmaceutically acceptable salt, for example, may be a metal salt, an ammonium salt, a salt formed with an organic base, a salt formed with an inorganic acid, a salt formed with an organic acid, a salt formed with a basic or acidic amino acid, and the like.

The term "pharmaceutical composition" refers to a mixture consisting of one or more of the compounds or pharmaceutically acceptable salts thereof disclosed herein and a pharmaceutically acceptable excipient. The pharmaceutical composition is intended to facilitate the administration of the compound disclosed herein to an organic entity.

The term "pharmaceutically acceptable excipients" refers to those which do not have a significant irritating effect on an organic entity and do not impair the biological activity and properties of the active compound. Suitable excipients are well known to a person skilled in the art, such as carbohydrate, wax, water-soluble and/or water-swellable polymers, hydrophilic or hydrophobic material, gelatin, oil, solvent, water.

The word "comprise" and variations thereof such as "comprises" or "comprising" shall be understood in an open, non-exclusive sense, i.e., "including but not limited to".

The compounds and intermediates disclosed herein may also exist in different tautomeric forms, and all such forms are included within the scope of the present application. The term "tautomer" or "tautomeric form" refers to structural isomers of different energies that can interconvert via a low energy barrier. For example, a proton tautomer (also referred to as proton transfer tautomer) includes interconversion via proton transfer, such as keto-enol isomerization and imine-enamine isomerization. A specific example of a proton tautomer is an imidazole moiety where a proton can transfer between two nitrogens of the ring. A valence tautomer includes the interconversion via recombination of some bonding electrons.

The present application also comprises isotopically-labeled compounds which are identical to those recited herein but one or more atoms thereof are replaced by an atom having an atomic mass or mass number different from the atomic mass or mass number usually found in nature. Examples of isotopes that can be incorporated into the compounds disclosed herein include isotopes of hydrogen, carbon, nitrogen, oxygen, phosphorus, sulfur, fluorine, iodine, and chlorine, such as $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl.

Certain isotopically-labeled compounds disclosed herein (e.g., those labeled with $^{3}$H and $^{14}$C) can be used to analyze tissue distribution of the compounds and/or substrate. Tritiated (i.e., $^{3}$H) and carbon-14 (i.e., $^{14}$C) isotopes are particularly preferred for their ease of preparation and detectability. Positron emitting isotopes, such as $^{15}$O, $^{13}$N, $^{11}$C, and $^{18}$F can be used in positron emission tomography (PET) studies to determine substrate occupancy. Isotopically-labeled compounds disclosed herein can generally be prepared by following procedures analogous to those disclosed in the schemes and/or examples below while substituting a non-isotopically labeled reagent with an isotopically-labeled reagent.

The compound disclosed herein can be asymmetrical, for example, has one or more stereoisomers. Unless otherwise stated, all stereoisomers are included, for example, enantiomers and diastereoisomers. The compound with asymetrical carbon atoms disclosed herein can be separated in an optically pure form or in a racemic form. The optically pure form can be separated from a racemic mixture or can be synthesized using a chiral raw material or a chiral reagent.

The pharmaceutical composition disclosed herein can be prepared by combining the compound disclosed herein with a suitable pharmaceutically acceptable excipient, and can be formulated, for example, into a solid, semisolid, liquid, or gaseous formulation, such as tablet, pill, capsule, powder, granule, ointment, emulsion, suspension, suppository, injection, inhalant, gel, microsphere, aerosol, and the like.

Typical routes of administration of a compound or a pharmaceutically acceptable salt thereof or a pharmaceutical composition thereof disclosed herein include, but are not limited to, oral, rectal, local, inhalation, parenteral, sublingual, intravaginal, intranasal, intraocular, intraperitoneal, intramuscular, subcutaneous and intravenous administration.

The pharmaceutical composition disclosed herein can be manufactured by methods well known in the art, such as by conventional mixing, dissolving, granulating, dragee-making, levigating, emulsifying, lyophilizing, and the like.

In some embodiments, the pharmaceutical composition is in an oral form. For oral administration, the pharmaceutical composition can be formulated by mixing the active compounds with pharmaceutically acceptable excipients well known in the art. These excipients enable the compounds disclosed herein to be formulated into tablets, pills, pastilles, dragees, capsules, liquids, gels, slurries, suspensions and the like for oral administration to a patient.

A solid oral composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to: binders, diluents, disintegrants, lubricants, glidants, sweeteners or flavoring agents and the like.

The pharmaceutical compositions may also be suitable for parenteral administration, such as sterile solutions, suspensions or lyophilized products in suitable unit dosage forms.

The compound disclosed herein can be prepared through various synthesis processes well-known to a person skilled in the art, including the specific embodiments illustrated below, the embodiments through combination of such specific embodiments with other chemical synthesis processes as well as equivalents well-known to a person skilled in the art. The preferable embodiments comprise but not limited to the working Examples herein.

The chemical reactions of the embodiments disclosed herein are carried out in a suitable solvent that must be suitable for the chemical changes in the present application and the reagents and materials required therefor. In order to obtain the compounds disclosed herein, a person skilled in the art sometimes needs to perform modification or selection to synthesis step or reaction procedure based on the known embodiments.

Synthesis Method

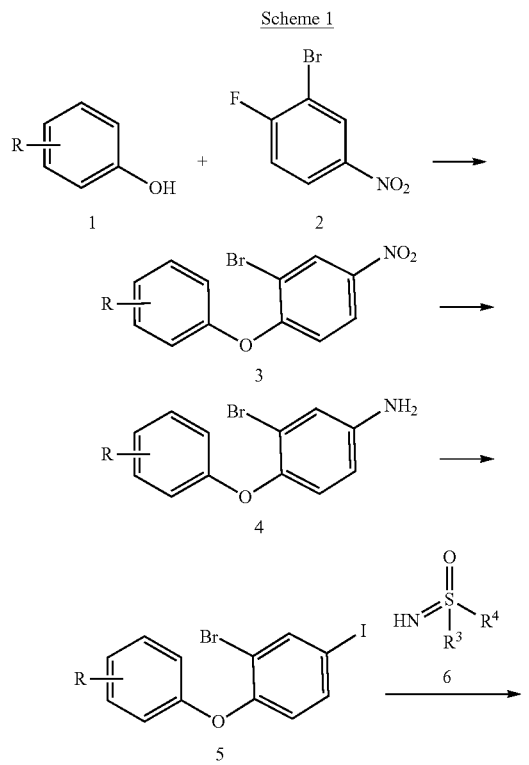

Scheme 1

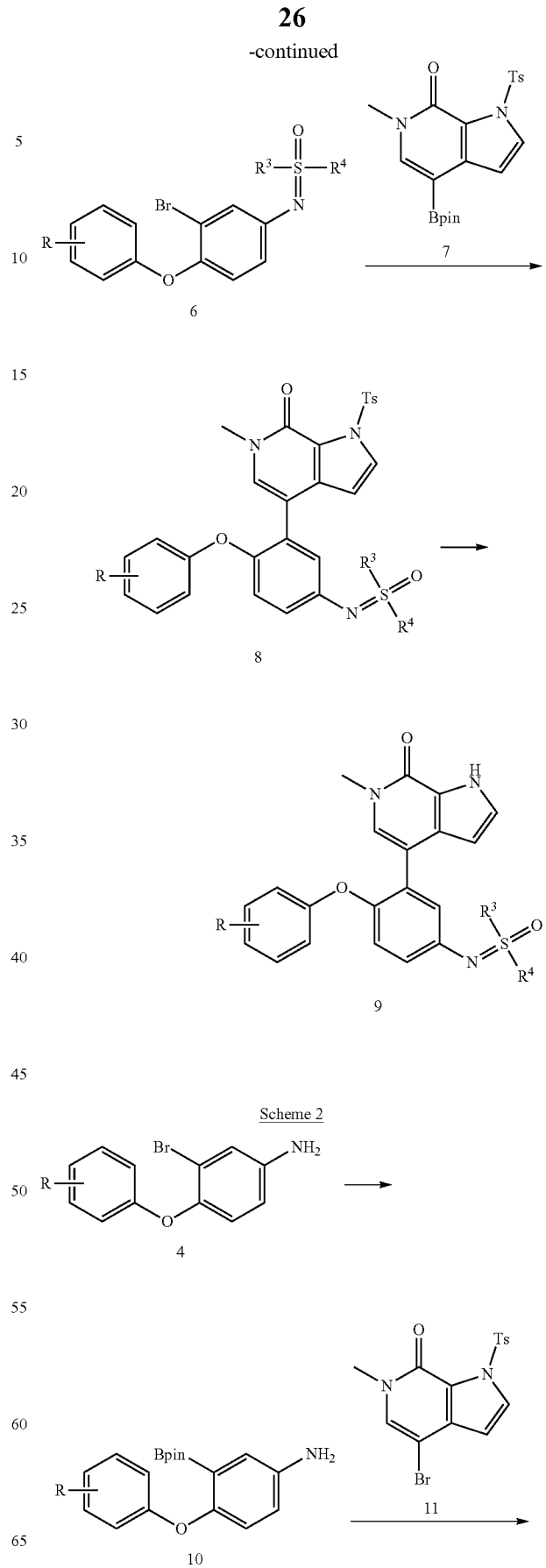

Scheme 2

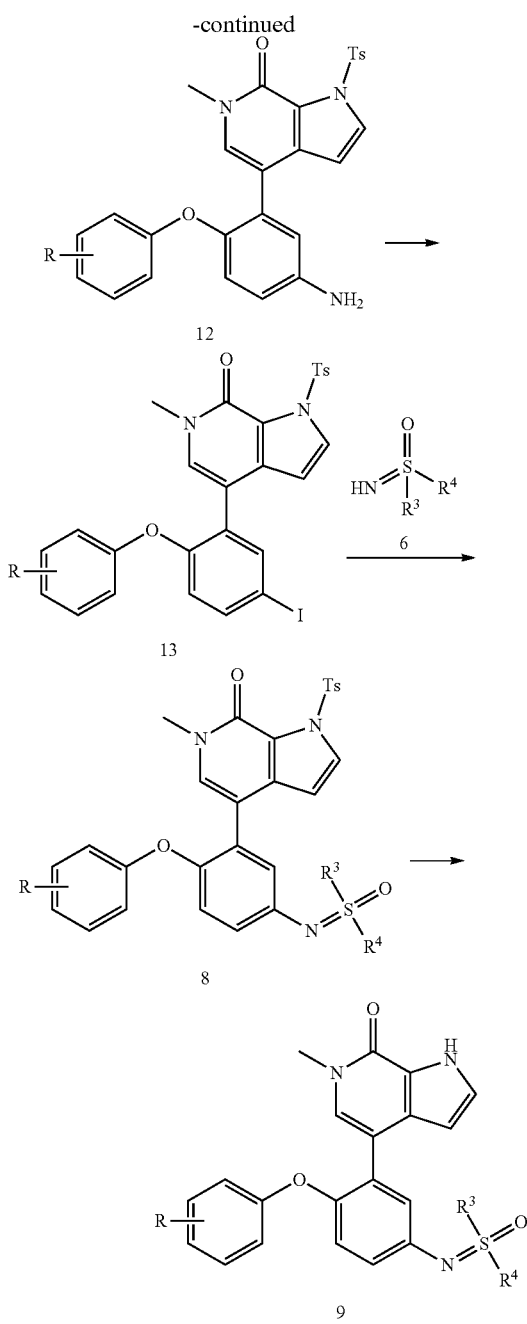

intermediate 4 is then diazotized and iodized to give corresponding iodo-intermediate 5, followed by coupling with corresponding sulfonimide to give intermediate 6. The intermediate 6 is reacted with the intermediate 7 to give intermediate 8 by Suzuki coupling reaction. Finally, the protection group is removed to give target product 9.

In scheme 2, the intermediate 4 is first subjected to Miyaura borylation to give intermediate 10, followed by Suzuki coupling reaction with bromo-intermediate 11 to give intermediate 12. The intermediate 12 is then diazotized and iodized to give corresponding iodo-intermediate 13, followed by coupling with corresponding sulfonimide to give intermediate 8. Finally, the protection group is removed according to the conditions in the scheme 1 to give the target product 9.

Specific Embodiments

The following non-limiting embodiments are merely illustrative and do not limit the present application in any way.

Unless otherwise stated, temperatures are in degrees Celsius. Reagents are purchased from commercial suppliers, such as the Sinopharm Chemical Reagent Beijing Co., Ltd., Alfa Aesar, or Beijing Bailingwei Chemical Technology Co., Ltd., and these reagents can be used directly without further purification unless otherwise stated.

Unless otherwise stated, the following reactions are preformed in anhydrous solvents under a positive pressure of nitrogen or argon, or in drying tubes; the reaction flask is equipped with a rubber diaphragm so as to add substrates and reagents through an injector; and the glassware is oven dried and/or dried by heating.

Unless otherwise stated, 200-300 mesh silica gels from Qingdao Haiyang Chemical Co., Ltd are used for column chromatography purification; thin layer chromatography silica gel prefabricated plates (HSGF254) produced by Yantai Institute of Chemical Industry are used for preparative thin-layer chromatography separation; and a Thermo LCQ Fleet (ESI) liquid chromatography-mass spectrometer is used for MS determination.

Nuclear magnetic resonance data ($^1$H NMR) are obtained using a Varian device running at 400 MHz. The nuclear magnetic resonance data are obtained using a solvent of $CDCl_3$, $CD_3OD$, $D_2O$, DMSO-$d_6$ or the like, based on tetramethylsilane (0.00 ppm) or residual solvents ($CDCl_3$: 7.26 ppm; $CD_3OD$: 3.31 ppm; $D_2O$: 4.79 ppm; DMSO-$d_6$: 2.50 ppm). When peak shape diversity is indicated, the following abbreviations represent different peak shapes: s (singlet peak), d (doublet peak), t (triplet peak), q (quartet peak), m (multiplet peak), br (broad peak), dd (double doublet peak), and dt (double triplet peak). If a coupling constant is given, then Hertz (Hz) is the unit.

Abbreviation:
AcOH Acetic acid
$CDCl_3$ Deuterated chloroform
DCM Dichloromethane
DIEA N,N-diisopropylethylamine
DMAP 4-dimethylaminopyridine
DMF N,N-dimethylformamide
DMSO Dimethyl sulfoxide
$Et_3N$ Triethylamine
EtOAc Ethyl acetate
EtOH Ethanol
$K_3PO_4$ Anhydrous potassium phosphate
LDA Lithium diisopropylamide
MeOH Methanol
MS Mass spectrometry
$N_2$ Nitrogen The compounds disclosed herein can be prepared according to the routes described in scheme 1 or scheme 2. Each of the products from the reactions of scheme 1 or scheme 2 may be obtained by conventional separation techniques including, but not limited to, filtration, distillation, crystallization, chromatographic separation, and the like. The starting materials may be self-synthesized or purchased from commercial establishments (such as, but not limited to, Adrich or Sigma). These materials can be characterized using conventional means, such as physical constants and spectral data. The compounds described herein can be synthesized as a single isomer or a mixture of isomers.

In scheme 1, material 1 and material 2 are involved in an SN2 reaction using a suitable base to give intermediate 3, and the intermediate 3 is reduced in the presence of zinc powder or iron powder to give amino intermediate 4. The NaH Sodium hydride
O₂ Oxygen
Pd₂(dba)₃ Tris(dibenzylideneacetone)dipalladium
PdCl₂(dppf) 1,1'-bis(diphenylphosphino)ferrocenepalladium dichloride
PE Petroleum ether
PTLC Preparative thin-layer chromatography
p-TSA p-toluenesulfonic acid
TBAF Tetrabutylammonium fluoride
TFA Trifluoroacetic acid
THF Tetrahydrofuran
TLC Thin-layer chromatography
XantPhos 4,5-bis(diphenylphosphino)-9,9-dimethylxanthene.

Example 1: 4-{5-{[dimethyl(oxo)-λ⁶-sulfanylidene]amino}-2-[4-(methylsulfonyl)phenoxy]phenyl}-N-ethyl-6-methyl-7-oxo-6,7-dihydro-1H-pyrrolo[2,3-c]pyridine-2-carboxamide

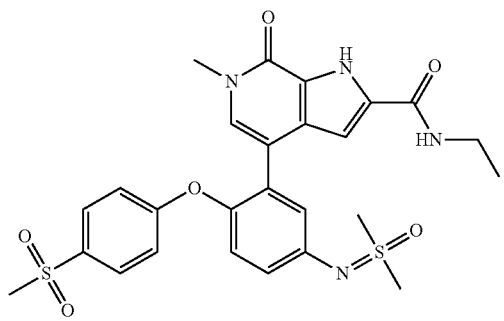

Step A: 2-bromo-1-[4-(methylsulfonyl)phenoxy]-4-nitrobenzene

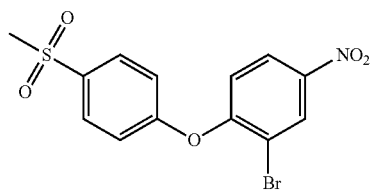 [SMILES: CS(=O)(=O)c1ccc(Oc2ccc([N+](=O)[O-])cc2Br)cc1]

At 0° C., 60% NaH (0.28 g) was added in portions to a solution of 4-(methylsulfonyl) phenol (1.00 g) in DMF (12 mL), and the mixture was stirred for 15 minutes, and added with 2-bromo-1-fluoro-4-nitrobenzene (1.28 g). After the addition, the mixture was warmed naturally to room temperature and reacted for 1 hour. The reaction mixture was poured into ice water, stirred for 15 minutes, and filtered, and the solid was collected to give the product (2.1 g).

¹H NMR (400 MHz CDCl₃) δ 8.60 (d, J=2.8 Hz, 1H), 8.22 (dd, J=8.8 Hz, 2.8 Hz, 1H), 7.98-8.02 (m, 2H), 7.15-7.18 (m, 2H), 7.09 (d, J=8.8 Hz, 1H), 3.09 (s, 3H).

Step B: 3-bromo-4-[4-(methylsulfonyl)phenoxy]aniline

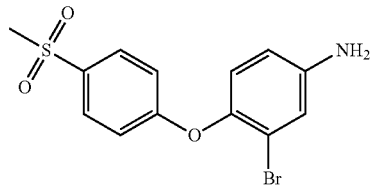

At room temperature, zinc powder (1.95 g) was added in portions to a solution of 2-bromo-1-[4-(methylsulfonyl)phenoxy]-4-nitrobenzene (1.10 g) in ethanol (20 mL) and acetic acid (5 mL) over about 30 minutes, and the mixture was stirred at room temperature overnight. The reaction mixture was diluted with dichloromethane, and filtered, and the filtrate was evaporated to dryness under reduced pressure. The residue was poured into a saturated aqueous sodium bicarbonate solution and extracted 3 times with ethyl acetate. The extracts were combined, washed sequentially with water and saturated brine, dried over anhydrous sodium sulfate, and concentrated under reduced pressure to remove the solvent to give the product (0.80 g).

¹H NMR (400 MHz, CDCl₃) δ 7.84-7.87 (m, 2H), 6.97-6.99 (m, 3H), 6.93 (d, J=8.8 Hz, 1H), 6.66 (dd, J=8.8 Hz, 2.8 Hz, 1H), 3.76 (brs, 2H), 3.04 (s, 3H).

Step C: 2-bromo-4-iodo-1-[4-(methylsulfonyl)phenoxy]benzene

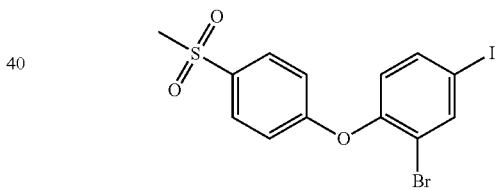

Under an ice bath, a solution of sodium nitrite (0.12 g) in water (1 mL) was slowly added dropwise to a solution of 3-bromo-4-[4-(methylsulfonyl)phenoxy]aniline (0.50 g) in 33% sulfuric acid (10 mL) and acetonitrile (10 mL) over about 2 minutes. Then, a solution of potassium iodide (2.50 g) in water (3 mL) was slowly added dropwise, and the mixture was warmed naturally to room temperature and reacted for 1 hour. The reaction mixture was poured into a saturated aqueous sodium bicarbonate solution (60 mL) containing ice. The resulting mixture was added with a saturated aqueous sodium thiosulfate solution (10 mL), and extracted 3 times with ethyl acetate. The extracts were combined, washed sequentially with water and saturated brine, dried over anhydrous sodium sulfate, and concentrated under reduced pressure to remove the solvent, and the residue was separated by silica gel column chromatography (EtOAc/PE=1/10-1/4) to give the product (0.40 g).

¹H NMR (400 MHz, CDCl₃) δ 8.01 (d, J=2.0 Hz, 1H), 7.89-7.92 (m, 2H), 7.67 (dd, J=8.4 Hz, 2.0 Hz, 1H), 7.01-7.04 (m, 2H), 6.85 (d, J=8.4 Hz, 1H), 3.06 (s, 3H).

Step D: N-{3-bromo-4-[4-(methylsulfonyl)phenoxy]phenyl}-S,S-dimethylsulfonimide

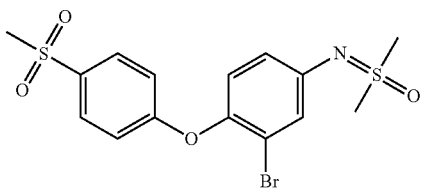 [SMILES: CS(=O)(=O)c1ccc(Oc2ccc(N=S(C)(C)=O)cc2Br)cc1]

To anhydrous dioxane (4 mL) were sequentially added 2-bromo-4-iodo-1-[4-(methylsulfonyl)phenoxy]benzene (0.10 g), dimethylsulfoximine (25 mg), cesium carbonate (0.14 g), Xantphos (10 mg), and $Pd_2(dba)_3$ (8 mg) under $N_2$ atmosphere, and the mixture was heated to 100° C. and stirred for 3 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (EtOAc/PE=1/1) to give the product (53 mg).

m/z=418[M+1]$^+$.

Step E: butyl 4-bromo-7-methoxy-1-tosyl-1H-pyrrolo[2,3-c]pyridine-2-carboxylate

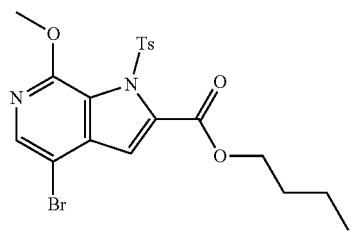 [SMILES: CCCCOC(=O)c1cc2c(Br)cnc(OC)c2n1S(=O)(=O)c1ccc(C)cc1]

A solution of 4-bromo-7-methoxy-1-tosyl-1H-pyrrolo[2,3-c]pyridine (1.2 g, obtained by referring to the method in reference J. Med. Chem. 2017, 60, 8369-8384) in anhydrous tetrahydrofuran (15 mL) was cooled to −78° C. under $N_2$ atmosphere. The solution was slowly added with a 2 mol/L solution of LDA in tetrahydrofuran (2.35 mL) dropwise with stirring, and stirred at −78° C. for 45 minutes. Then a solution of n-butyl chloroformate (0.64 g) in tetrahydrofuran (5 mL) was added dropwise to the reaction mixture. After the addition, the resulting mixture was stirred at this temperature for 1.5 hours. After the reaction was completed as monitored, a saturated aqueous ammonium chloride solution (15 mL) was added to quench the reaction, and ethyl acetate was added for extraction. The extract was washed with saturated brine, and dried over anhydrous sodium sulfate, and the solvent was removed. The residue was purified by silica gel column chromatography (EtOAc/PE=1/4) to give the product (1.0 g).

$^1$H NMR (400 MHz, CDCl$_3$) δ 8.26 (d, J=8.4 Hz, 2H), 7.99 (s, 1H), 7.38 (d, J=8.4 Hz, 2H), 7.07 (s, 1H), 4.42 (t, J=6.4 Hz, 2H), 3.91 (s, 3H), 2.47 (s, 3H), 1.80-1.82 (m, 2H), 1.51-1.55 (m, 2H), 0.97-1.01 (t, J=7.2 Hz, 3H).

Step F: butyl 4-bromo-7-oxo-1-tosyl-6,7-dihydro-1H-pyrrolo[2,3-c]pyridine-2-carboxylate

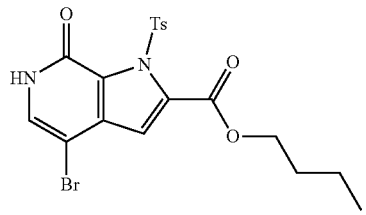 [SMILES: CCCCOC(=O)c1cc2c(Br)c[nH]c(=O)c2n1S(=O)(=O)c1ccc(C)cc1]

Butyl 4-bromo-7-methoxy-1-tosyl-1H-pyrrolo[2,3-c]pyridine-2-carboxylate (4.81 g) was dissolved in dioxane (10 mL) at room temperature, and the solution was added with concentrated hydrochloric acid (10 mL), heated to 40° C., and stirred overnight. After cooling to room temperature, the white suspension was filtered and washed with a saturated aqueous NaHCO$_3$ solution and water to give a white solid, which was air-dried to give the product (2.4 g).

$^1$H NMR (400 MHz, CDCl$_3$) δ 10.98 (brs, 1H), 8.40 (d, J=8.4 Hz, 2H), 7.36 (d, J=8.4 Hz, 2H), 7.14 (s, 1H), 6.89 (s, 1H), 4.42 (t, J=6.8 Hz, 2H), 2.45 (s, 3H), 1.78-1.82 (m, 2H), 1.48-1.50 (m, 2H), 0.99 (t, J=7.2 Hz, 3H).

Step G: butyl 4-bromo-6-methyl-7-oxo-1-tosyl-6,7-dihydro-1H-pyrrolo[2,3-c]pyridine-2-carboxylate

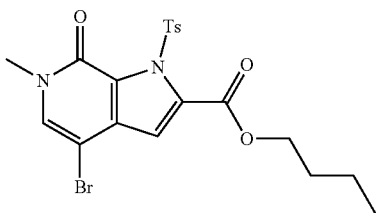 [SMILES: CCCCOC(=O)c1cc2c(Br)cn(C)c(=O)c2n1S(=O)(=O)c1ccc(C)cc1]

At room temperature, butyl 4-bromo-7-oxo-1-tosyl-6,7-dihydro-1H-pyrrolo[2,3-c]pyridine-2-carboxylate (2.4 g) was dissolved in DMF (20 mL), and the solution was added with anhydrous cesium carbonate (2.52 g) and iodomethane (0.87 g, 1.2 eq) and stirred overnight. The mixture was added ethyl acetate (100 mL), slurried and filtered, and the filtrate was washed with 1 N HCl and saturated brine, dried over anhydrous sodium sulfate, and evaporated to remove the solvent. The residue was purified by silica gel column chromatography (EtOAc/PE=1/2) to give the product (1.5 g).

$^1$H NMR (400 MHz, CDCl$_3$) δ 8.47 (d, J=8.4 Hz, 2H), 7.39 (d, J=8.4 Hz, 2H), 7.26 (s, 1H), 6.87 (s, 1H), 4.41 (t, J=6.8 Hz, 2H), 3.56 (s, 3H), 2.45 (s, 3H), 1.77-1.81 (m, 2H), 1.48-1.50 (m, 2H), 0.99 (t, J=7.2 Hz, 3H).

Step H: 4-bromo-N-ethyl-6-methyl-7-oxo-6,7-dihydro-1H-pyrrolo[2,3-c]pyridine-2-carboxamide

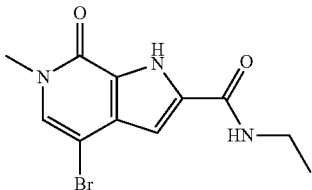 [SMILES: CCNC(=O)c1cc2c(Br)cn(C)c(=O)c2[nH]1]

In a sealed tube, butyl 4-bromo-6-methyl-7-oxo-1-tosyl-6,7-dihydro-1H-pyrrolo[2,3-c]pyridine-2-carboxylate (1.5 g) was dispersed in 60% aqueous ethylamine solution (10 mL), and the mixture was charged with nitrogen, heated to 80° C., and stirred overnight. Most of the solvent was evaporated off and the residue was purified by silica gel column chromatography (100% EtOAc) to give the product (0.46 g).

$^1$H NMR (400 MHz, CDCl$_3$) δ 12.00 (brs, 1H), 8.454 (t, J=5.2 Hz, 1H), 7.60 (s, 1H), 6.86 (s, 1H), 3.50 (s, 3H), 3.25-3.32 (m, 2H), 1-1.14 (t, J=7.2 Hz, 3H).

Step I: N-ethyl-6-methyl-7-oxo-4-(4,4,5,5-tetramethyl-1,3,2-dioxaborolan-2-yl)-6,7-dihydro-1H-pyrrolo[2,3-c]pyridine-2-carboxamide

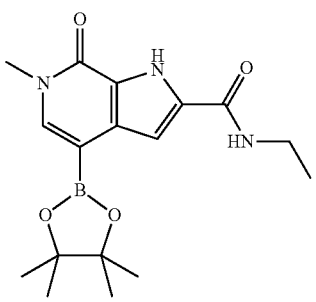 [SMILES: CCNC(=O)c1cc2c(B3OC(C)(C)C(C)(C)O3)cn(C)c(=O)c2[nH]1]

To a mixed solvent of 1,4-dioxane (20 mL) and water (2 mL) were sequentially added 4-bromo-N-ethyl-6-methyl-7-oxo-6,7-dihydro-1H-pyrrolo[2,3-c]pyridine-2-carboxamide (0.46 g), bis(pinacolato)diboron (0.66 g), Xphos (31 mg), potassium acetate (0.28 g), and Pd$_2$(dba)$_3$ (30 mg) under N$_2$ atmosphere, and the mixture was heated to 80° C., stirred overnight, and cooled to room temperature. The reaction mixture was dispersed in ethyl acetate, washed sequentially with a saturated aqueous NaHCO$_3$ solution and water, dried over anhydrous sodium sulfate, and evaporated to remove the solvent. The residue was purified by silica gel column chromatography (EtOAc/PE=1/3-1/1) to give the product (0.3 g).

$^1$H NMR (400 MHz, CDCl$_3$) δ 10.26 (brs, 1H), 7.48 (s, 1H), 7.02 (s, 1H), 6.41 (brs, 1H), 3.66 (s, 3H), 3.53 (q, J=7.2 Hz, 2H), 1.37 (s, 12H), 1.28 (t, J=7.2 Hz, 3H).

Step J: 4-{5-{[dimethyl(oxo)-λ$^6$-sulfanylidene]amino}-2-[4-(methylsulfonyl)phenoxy]phenyl}-N-ethyl-6-methyl-7-oxo-6,7-dihydro-1H-pyrrolo[2,3-c]pyridine-2-carboxamide

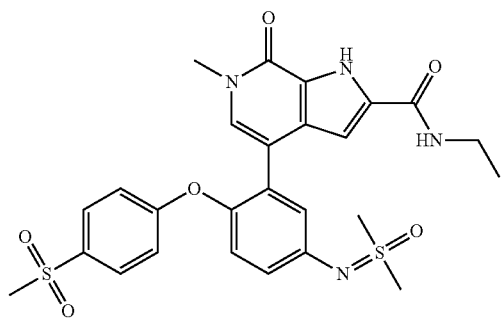 [SMILES: CCNC(=O)c1cc2c(-c3cc(N=S(C)(C)=O)ccc3Oc3ccc(S(C)(=O)=O)cc3)cn(C)c(=O)c2[nH]1]

To an 80% aqueous dioxane solution (3 mL) were sequentially added N-{3-bromo-4-[4-(methylsulfonyl)phenoxy]phenyl}-S,S-dimethylsulfonimide (20 mg), N-ethyl-6-methyl-7-oxo-4-(4,4,5,5-tetramethyl-1,3,2-dioxaborolan-2-yl)-6,7-dihydro-1H-pyrrolo[2,3-c]pyridine-2-carboxamide (20 mg), cesium fluoride (22 mg), and PdCl$_2$(dppf) (3 mg) under N$_2$ atmosphere, and the mixture was heated to 85° C. and stirred overnight. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (MeOH/DCM=1/20) to give the product (15 mg).

$^1$H NMR (400 MHz, CDCl$_3$) δ 11.32 (s, 1H), 7.69 (d, J=8.8 Hz 2H), 7.21-7.25 (m, 2H), 7.17 (dd, J=8.8 Hz, 2.4 Hz, 1H), 7.06 (d, J=8.8 Hz, 1H), 6.99 (s, 1H), 6.92 (d, J=2.0 Hz, 1H), 6.81 (d, J=8.8 Hz, 2H), 3.61 (s, 3H), 3.45-3.54 (m, 2H), 3.22 (s, 6H), 2.96 (s, 3H), 1.26 (t, J=7.2 Hz, 3H).

Example 2: 4-{4-{[dimethyl(oxo)-λ$^6$-sulfanylidene]amino}-2-(6-methyl-7-oxo-6,7-dihydro-1H-pyrrolo[2,3-c]pyridin-4-yl)phenoxy}-3-fluorobenzonitrile

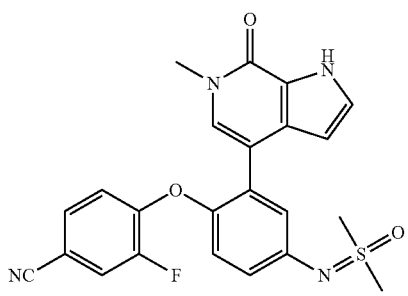 [SMILES: Cn1cc(-c2cc(N=S(C)(C)=O)ccc2Oc2ccc(C#N)cc2F)c2cc[nH]c2c1=O]

Step A: 4-{2-bromo-4-{[dimethyl(oxo)-λ⁶-sulfanylidene]amino}phenoxy}-3-fluorobenzonitrile

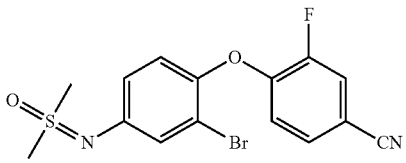 [SMILES: CS(C)(=O)=Nc1ccc(Oc2ccc(C#N)cc2F)c(Br)c1]

The product was obtained by referring to steps A-D in Example 1, starting from 2-bromo-1-fluoro-4-nitrobenzene and 3-fluoro-4-hydroxybenzonitrile.

¹H NMR (400 MHz, CDCl₃) δ 7.47 (dd, J=10.0 Hz, 2.0 Hz, 1H), 7.39 (d, J=2.4 Hz, 1H), 7.31-7.34 (m, 1H), 7.06 (dd, J=8.8 Hz, 2.4 Hz, 1H), 6.98 (d, J=8.8 Hz, 1H), 6.74 (t, J=8.4 Hz, 1H), 3.19 (s, 6H).

Step B: 4-bromo-6-methyl-1,6-dihydro-7H-pyrrolo[2,3-c]pyridin-7-one

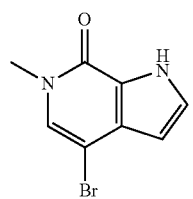

Tetrabutylammonium fluoride (0.5 g) was added to a solution of 4-bromo-6-methyl-1-tosyl-1,6-dihydro-7H-pyrrolo[2,3-c]pyridin-7-one (0.5 g, obtained by referring to the method in reference *J. Med. Chem.* 2017, 60, 8369-8384) in tetrahydrofuran (20 mL), and the mixture was heated to 70° C., and stirred for 2 hours. The reaction mixture was dispersed in ethyl acetate, washed with water, dried over anhydrous sodium sulfate, and evaporated to remove the solvent to give the product (0.35 g), m/z=227[M+1]*.

Step C: 6-methyl-4-(4,4,5,5-tetramethyl-1,3,2-dioxaborolan-2-yl)-1,6-dihydro-7H-pyrrolo[2,3-c]pyridin-7-one

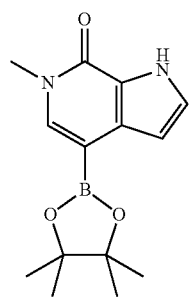 [SMILES: Cn1cc(B2OC(C)(C)C(C)(C)O2)c2cc[nH]c2c1=O]

To a mixed solvent of 1,4-dioxane (20 mL) and water (2 mL) were sequentially added 4-bromo-6-methyl-1,6-dihydro-7H-pyrrolo[2,3-c]pyridin-7-one (0.35 g), bis(pinacolato)diboron (0.66 g), Xphos (31 mg), potassium acetate (0.28 g), and Pd₂(dba)₃ (30 mg) under N₂ atmosphere, and the mixture was heated to 80° C., stirred overnight, and cooled to room temperature. The reaction mixture was dispersed in ethyl acetate, washed with a saturated aqueous NaHCO₃ solution, washed with water, and dried over anhydrous sodium sulfate, and evaporated to remove the solvent. The residue was purified by silica gel column chromatography (EtOAc/PE=1/1) to give the product (0.2 g).

¹H NMR (400 MHz, CDCl₃) δ 9.79 (brs, 1H), 7.47 (s, 1H), 7.24-7.26 (m, 1H), 6.76-6.77 (m, 1H), 3.66 (s, 3H), 1.36 (s, 12H).

Step D: 4-{4-{[dimethyl(oxo)-λ⁶-sulfanylidene]amino}-2-(6-methyl-7-oxo-6,7-dihydro-1H-pyrrolo[2,3-c]pyridin-4-yl)phenoxy}-3-fluorobenzonitrile

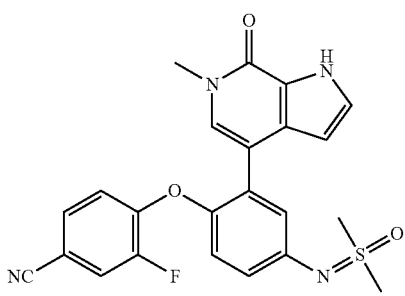 [SMILES: Cn1cc(-c2cc(N=S(C)(C)=O)ccc2Oc2ccc(C#N)cc2F)c2cc[nH]c2c1=O]

To an 80% aqueous dioxane solution (3 mL) were sequentially added 4-{2-bromo-4-{[dimethyl(oxo)-λ⁶-sulfanylidene]amino}phenoxy}-3-fluorobenzonitrile (40 mg), 6-methyl-4-(4,4,5,5-tetramethyl-1,3,2-dioxaborolan-2-yl)-1,6-dihydro-7H-pyrrolo[2,3-c]pyridin-7-one (43 mg), cesium fluoride (48 mg), and PdCl₂(dppf) (4 mg), and the mixture was heated to 85° C. and stirred overnight. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (MeOH/DCM=1/20) to give the product (30 mg).

¹H NMR (400 MHz, CDCl₃) δ 9.98 (s, 1H), 7.25-7.30 (d, 2H), 7.21 (t, J=2.8 Hz, 1H), 7.11-7.15 (m, 2H), 7.09 (s, 1H), 7.06 (d, J=8.4 Hz, 1H), 6.68 (t, J=8.4 Hz, 1H), 6.41 (t, J=2.8 Hz, 1H), 3.61 (s, 3H), 3.20 (s, 6H).

Example 3: 4-{5-{[dimethyl(oxo)-λ⁶-sulfanylidene]amino}-2-[4-(methylsulfonyl)phenoxy]phenyl}-6-methyl-1,6-dihydro-7H-pyrrolo[2,3-c]pyridin-7-one

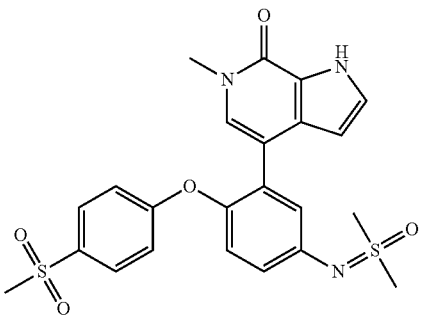 [SMILES: Cn1cc(-c2cc(N=S(C)(C)=O)ccc2Oc2ccc(S(C)(=O)=O)cc2)c2cc[nH]c2c1=O]

Step A: 4-{5-{[dimethyl(oxo)-λ⁶-sulfanylidene]amino}-2-[4-(methylsulfonyl)phenoxy]phenyl}-6-methyl-1-tosyl-1,6-dihydro-7H-pyrrolo[2,3-c]pyridin-7-one

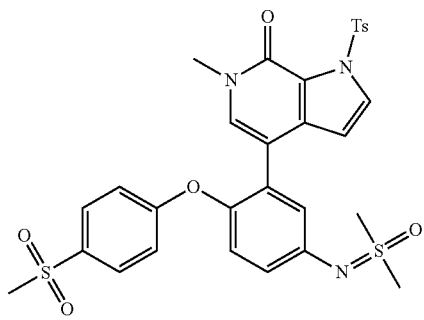 [SMILES: Cc1ccc(S(=O)(=O)n2ccc3c(-c4cc(N=S(C)(C)=O)ccc4Oc4ccc(S(C)(=O)=O)cc4)cn(C)c(=O)c32)cc1]

To an 80% aqueous dioxane solution (3 mL) were sequentially added N-{3-bromo-4-[4-(methylsulfonyl) phenoxy] phenyl}-S,S-dimethylsulfonimide (40 mg), 6-methyl-4-(4,4,5,5-tetramethyl-1,3,2-dioxaborolan-2-yl)-1-toluenesulfonyl-1,6-dihydro-7H-pyrrolo[2,3-c]pyridin-7-one (61 mg, obtained by referring to the method in reference J. Med. Chem. 2017, 60, 8369-8384), cesium fluoride (44 mg), and PdCl₂(dppf) (4 mg) under N₂ atmosphere, and the mixture was heated to 85° C. and stirred overnight. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (MeOH/DCM=1/30) to give the product (45 mg).

¹H NMR (400 MHz, CDCl₃) δ 7.98 (d, J=8.4 Hz, 2H), 7.88 (d, J=3.2 Hz, 1H), 7.68 (d, J=8.4 Hz, 2H), 7.30 (d, J=8.4 Hz, 2H), 7.12-7.15 (m, 2H), 7.01-7.05 (m, 2H), 6.77 (d, J=8.4 Hz, 2H), 6.49 (d, J=3.2 Hz, 1H), 3.45 (s, 3H), 3.20 (s, 6H), 2.96 (s, 3H), 2.41 (s, 3H).

Step B: 4-{5-{[dimethyl(oxo)-λ⁶-sulfanylidene]amino}-2-[4-(methylsulfonyl)phenoxy]phenyl}-6-methyl-1,6-dihydro-7H-pyrrolo[2,3-c]pyridin-7-one

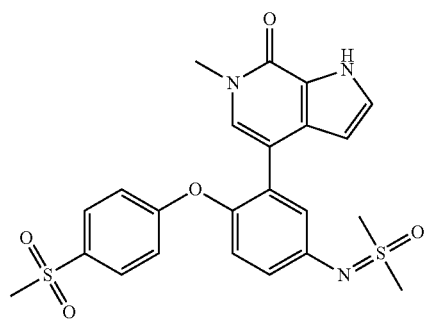 [SMILES: Cn1cc(-c2cc(N=S(C)(C)=O)ccc2Oc2ccc(S(C)(=O)=O)cc2)c2cc[nH]c2c1=O]

To a solution of 4-{5-{[dimethyl(oxo)-λ⁶-sulfanylidene]amino}-2-[4-(methylsulfonyl)phenoxy]phenyl}-6-methyl-1-tosyl-1,6-dihydro-7H-pyrrolo[2,3-c]pyridin-7-one (45 mg) in ethanol (1 mL) was added a 1 moL/L NaOH solution (1 mL), and the mixture was heated to 80° C. and stirred for 1 hour. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (MeOH/DCM=1/20) to give the product (20 mg).

¹H NMR (400 MHz, CDCl₃) δ 10.59 (s, 1H), 7.68 (d, J=8.8 Hz, 2H), 7.27 (d, J=2.8 Hz, 1H), 7.23 (t, J=2.4 Hz, 1H), 7.13 (dd, J=8.4 Hz, 2.4 Hz, 1H), 7.05 (d, J=8.8 Hz, 1H), 6.96 (s, 1H), 6.82 (d, J=8.8 Hz, 2H), 6.41 (t, J=2.4 Hz, 1H), 3.60 (s, 3H), 3.21 (s, 6H), 2.95 (s, 3H).

Example 4: 4-{2-(2,4-difluorophenoxy)-5-{[dimethyl(oxo)-λ⁶-sulfanylidene]amino}-pyridin-3-yl}-6-methyl-1,6-dihydro-7H-pyrrolo[2,3-c]pyridin-7-one

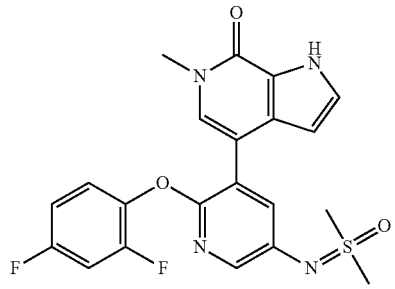

Step A: N-[5-bromo-6-(2,4-difluorophenoxy)pyridin-3-yl]-S,S-dimethylsulfonimide

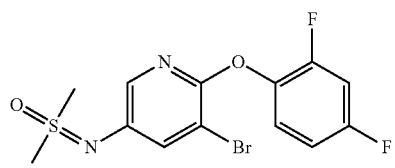 [SMILES: CS(C)(=O)=Nc1cnc(Oc2ccc(F)cc2F)c(Br)c1]

The product was obtained by referring to steps A-D in Example 1, starting from 3-bromo-2-fluoro-5-nitropyridine and 2,4-diflurophenol.

¹H NMR (400 MHz CDCl₃) δ 7.77 (d, J=2.4 Hz, 1H), 7.73 (d, J=2.4 Hz, 1H), 7.17-7.23 (m, 1H), 6.87-6.97 (m, 2H), 3.15 (s, 6H).

Step B: 4-{2-(2,4-difluorophenoxy)-5-{[dimethyl(oxo)-λ⁶-sulfanylidene]amino}-pyridin-3-yl}-6-methyl-1-tosyl-1,6-dihydro-7H-pyrrolo[2,3-c]pyridin-7-one

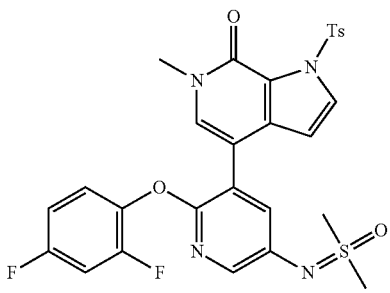 [SMILES: Cc1ccc(S(=O)(=O)n2ccc3c(-c4cc(N=S(C)(C)=O)cnc4Oc4ccc(F)cc4F)cn(C)c(=O)c32)cc1]

The product (50 mg) was obtained by referring to step A in Example 3.

¹H NMR (400 MHz, CDCl₃) δ 8.04 (d, J=8.4 Hz, 2H), 7.91 (d, J=3.6 Hz, 1H), 7.84 (d, J=1.6 Hz, 1H), 7.47 (d, J=2.8 Hz, 1H), 7.31 (d, J=8.4 Hz, 2H), 7.23 (s, 1H), 7.07-7.13 (m, 1H), 6.84-6.95 (m, 2H), 6.54 (d, J=3.2 Hz, 1H), 3.57 (s, 3H), 3.16 (s, 6H), 2.40 (s, 3H).

Step C: 4-{2-(2,4-difluorophenoxy)-5-{[dimethyl(oxo)-λ⁶-sulfanylidene]amino}-pyridin-3-yl}-6-methyl-1,6-dihydro-7H-pyrrolo[2,3-c]pyridin-7-one

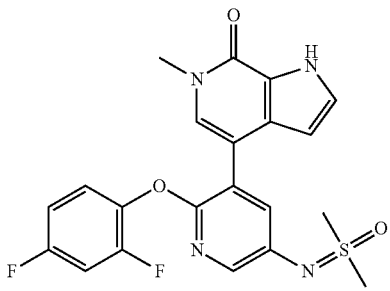

The product (24 mg) was obtained by referring to step B in Example 3.

¹H NMR (400 MHz, CDCl₃) δ 9.71 (s, 1H), 7.84 (d, J=2.8 Hz, 1H), 7.62 (d, J=2.8 Hz, 1H), 7.25 (s, 1H), 7.24 (d, 1H), 7.11-7.17 (m, 1H), 6.84-6.96 (m, 2H), 6.51 (d, J=2.8 Hz, 1H), 3.72 (s, 3H), 3.17 (s, 6H).

Example 5: 4-{2-(2,4-difluorophenoxy)-5-{[dimethyl(oxo)-λ⁶-sulfanylidene]amino}phenyl}-6-methyl-1,6-dihydro-7H-pyrrolo[2,3-c]pyridin-7-one

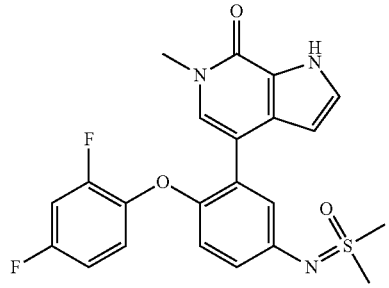 [SMILES: Cn1cc(-c2cc(N=S(C)(C)=O)ccc2Oc2ccc(F)cc2F)c2cc[nH]c2c1=O]

Step A: 2-bromo-1-(2,4-difluorophenoxy)-4-nitrobenzene

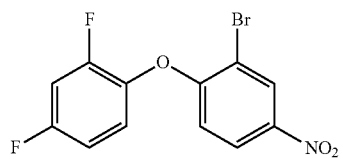

2,4-difluorophenol (1.43 g), 2-bromo-1-fluoro-4-nitrobenzene (2.2 g) and cesium carbonate (4.9 g) were added to DMSO (20 mL), and the mixture was stirred at 100° C. for 2 hours, and cooled to room temperature. The reaction mixture was poured into water, stirred for 15 minutes, filtered, and the solid was collected to give the product (3.4 g).

¹H NMR (400 MHz CDCl₃) δ 8.55 (d, J=2.8 Hz, 1H), 8.10 (dd, J=9.2 Hz, 2.8 Hz, 1H), 7.21 (td, J=8.8 Hz, 5.2 Hz, 1H), 6.94-7.06 (m, 2H), 6.73 (d, J=9.2 Hz, 1H).

Step B: 3-bromo-4-(2,4-difluorophenoxy)aniline

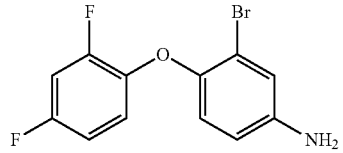 [SMILES: Nc1ccc(Oc2ccc(F)cc2F)c(Br)c1]

To a solution of 2-bromo-1-(2,4-difluorophenoxy)-4-nitrobenzene (3.4 g) in ethanol (30 mL) and acetic acid (10 mL) was added zinc powder (6.0 g) in portions at room temperature over about 10 minutes, and the mixture was stirred at room temperature for 2 hours. The reaction mixture was diluted with dichloromethane, and filtered, and the filtrate was evaporated to dryness under reduced pressure. The residue was poured into a saturated aqueous sodium bicarbonate solution and extracted 3 times with ethyl acetate. The extracts were combined, washed sequentially with water and saturated brine, dried over anhydrous sodium sulfate, and concentrated under reduced pressure to remove the solvent to give the product (2.81 g).

¹H NMR (400 MHz, CDCl₃) δ 6.90-6.95 (m, 2H), 6.72-6.81 (m, 3H), 6.58 (dd, J=8.8 Hz, 2.8 Hz, 1H), 3.70 (s, 2H).

Step C: 4-(2,4-difluorophenoxy)-3-(4,4,5,5-tetramethyl-1,3,2-dioxaboran-2-yl)aniline

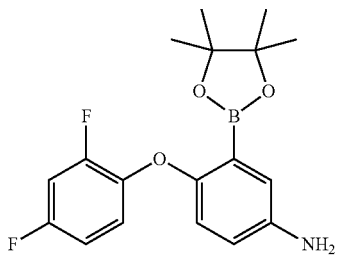 [SMILES: CC1(C)OB(c2cc(N)ccc2Oc2ccc(F)cc2F)OC1(C)C]

3-bromo-4-(2,4-difluorophenoxy)aniline (2.0 g), bis(pinacolato)diboron (3.4 g), potassium acetate (1.6 g), and Pd(dppf)Cl₂ (241 mg) were dissolved in dioxane (50 mL), and the mixture was stirred at 100° C. under nitrogen atmosphere for 12 hours, and concentrated under reduced pressure to remove the solvent. The mixture was separated by silica gel column chromatography (MeOH/DCM=1/40) to give the product (900 mg).

¹H NMR (400 MHz, CDCl₃) δ 7.12 (d, J=2.8 Hz, 1H), 6.79-6.93 (m, 3H), 6.61-6.67 (m, 1H), 6.56 (td, J 9.2 Hz, 5.2 Hz, 1H), 3.65-4.46 (brs, 2H), 1.16 (s, 12H).

Step D: 4-[5-amino-2-(2,4-difluorophenoxy)phenyl]-6-methyl-1-tosyl-1,6-dihydro-7H-pyrrolo[2,3-c]pyridin-7-one

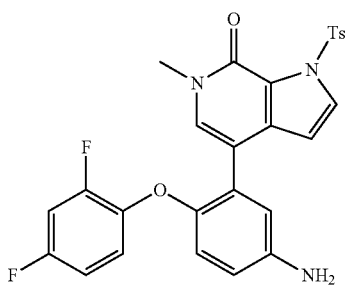

To a mixed solution of dioxane solution and water (30 mL:6 mL) were sequentially added 4-(2,4-difluorophenoxy)-3-(4,4,5,5-tetramethyl-1,3,2-dioxaboran-2-yl)aniline (900 mg), 4-bromo-6-methyl-1-tosyl-1,6-dihydro-7H-pyrrolo[2,3-c]pyridin-7-one (1.2 g), potassium phosphate (1.6 g), and PdCl₂(dppf) (190 mg) under N₂ atmosphere, and the mixture was heated to 100° C. and stirred for 12 hours. The reaction mixture was cooled to room temperature, added with water, and extracted with dichloromethane. The extract was washed with water and saturated brine, dried over anhydrous sodium sulfate, and concentrated under reduced pressure. The residue was separated by silica gel column chromatography (MeOH/DCM=1/30) to give the product (1.3 g).

¹H NMR (400 MHz, CDCl₃) δ 8.01 (d, J=8.4 Hz, 2H,), 7.86 (d, J=3.6 Hz, 1H,), 7.30 (d, J=8.4 Hz, 2H), 7.11 (s, 1H), 6.63-6.81 (m, 6H), 6.46 (d, J=3.6 Hz, 1H), 3.56-3.72 (brs, 2H), 3.51 (s, 3H), 2.41 (s, 3H).

Step E: 4-(2-(2,4-difluorophenoxy)-5-iodobenzene)-6-methyl-1-tosyl-1,6-dihydro-7H-pyrrolo[2,3-c]pyridin-7-one

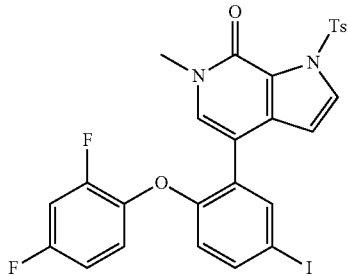 [SMILES: Cc1ccc(S(=O)(=O)n2ccc3c(-c4cc(I)ccc4Oc4ccc(F)cc4F)cn(C)c(=O)c32)cc1]

Under an ice bath, to a solution of 4-[5-amino-2-(2,4-difluorophenoxy)phenyl]-6-methyl-1-tosyl-1,6-dihydro-7H-pyrrolo[2,3-c]pyridin-7-one (200 mg) in 33% sulfuric acid (10 mL) and acetonitrile (10 mL) was slowly added a solution of sodium nitrite (29 mg) in water (1 mL) dropwise over about 5 minutes. After 15 minutes, a solution of potassium iodide (252 mg) in water (3 mL) was slowly added dropwise, and the mixture was warmed naturally to room temperature and stirred for 1 hour. The reaction mixture was poured into a saturated aqueous sodium bicarbonate solution (60 mL) containing ice. The resulting mixture was added with a saturated aqueous sodium thiosulfate solution (10 mL), and extracted 3 times with ethyl acetate. The extracts were combined, washed sequentially with water and saturated brine, dried over anhydrous sodium sulfate, and concentrated under reduced pressure to remove the solvent, and the residue was separated by silica gel column chromatography (MeOH/DCM=1/30) to give the product (120 mg).

¹H NMR (400 MHz, CDCl₃) δ 8.03 (d, J=8.4 Hz, 2H), 7.89 (d, J=3.6 Hz, 1H), 7.66 (d, J=2.4 Hz, 1H), 7.57 (dd, J=8.8 Hz, 2.0 Hz, 1H), 7.31 (d, J=8.4 Hz, 2H), 7.13 (s, 1H), 6.86-6.95 (m, 2H), 6.77-6.82 (m, 1H), 6.54 (d, J=8.4 Hz, 1H), 6.43 (d, J=3.6 Hz, 1H), 3.55 (s, 3H), 2.41 (s, 3H).

Step F: 4-{2-(2,4-difluorophenoxy)-5-{[dimethyl(oxy)-λ⁶-sulfanylidene]amino}phenyl}-6-methyl-1-tosyl-1,6-dihydro-7H-pyrrolo[2,3-c]pyridin-7-one

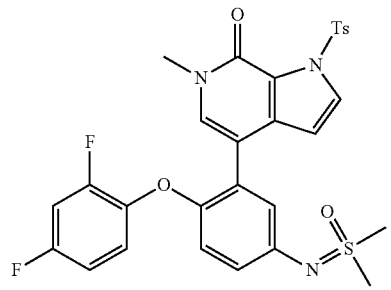 [SMILES: Cc1ccc(S(=O)(=O)n2ccc3c(-c4cc(N=S(C)(C)=O)ccc4Oc4ccc(F)cc4F)cn(C)c(=O)c32)cc1]

To anhydrous dioxane (10 mL) were sequentially added 4-[2-(2,4-difluorophenoxy)-5-iodobenzene]-6-methyl-1-tosyl-1,6-dihydro-7H-pyrrolo[2,3-c]pyridin-7-one (30 mg), dimethylsulfoximine (5 mg), cesium carbonate (23 mg), Xantphos (2 mg), and Pd₂(dba)₃ (1 mg) under N₂ atmosphere, and the mixture was heated to 100° C. and stirred for 3 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (MeOH/DCM=1/25) to give the product (10 mg).

¹H NMR (400 MHz, CDCl₃) δ 8.01 (d, J=8.4 Hz, 2H), 7.87 (d, J=3.6 Hz, 1H), 7.30 (d, J=8.4 Hz, 2H), 7.15 (s, 1H), 7.08 (d, J=2.8 Hz, 1H), 7.01 (dd, J=8.8 Hz, 2.4 Hz, 1H), 6.77-6.84 (m, 3H), 6.66-6.73 (m, 1H), 6.50 (d, J=3.6 Hz, 1H), 3.52 (s, 3H), 3.16 (s, 6H), 2.40 (s, 3H).

Step G: 4-{2-(2,4-difluorophenoxy)-5-{[dimethyl(oxo)-λ⁶-sulfanylidene]amino}phenyl}-6-methyl-1,6-dihydro-7H-pyrrolo[2,3-c]pyridin-7-one

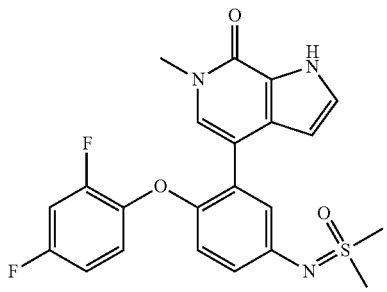 [SMILES: Cn1cc(-c2cc(N=S(C)(C)=O)ccc2Oc2ccc(F)cc2F)c2cc[nH]c2c1=O]

To a mixed solution of ethanol and 1 N NaOH (3 mL:3 mL) was added 4-{2-(2,4-difluorophenoxy)-5-{[dimethyl(oxy)-λ⁶-sulfanylidene]amino}phenyl}-6-methyl-1-tosyl-1,6-dihydro-7H-pyrrolo[2,3-c]pyridin-7-one (10 mg), and the mixture was stirred at 70° C. for 1 hour. The reaction mixture was cooled to room temperature, concentrated under reduced pressure, added with a saturated aqueous disodium hydrogen phosphate solution, and extracted with dichloromethane. The extract was washed with water and saturated brine, dried over anhydrous sodium sulfate, and concentrated under reduced pressure. The residue was separated by a preparative thin-layer plate (MeOH/DCM=1/20) to give the product (7 mg).

¹H NMR (400 MHz, CDCl₃) δ 9.58-9.68 (brs, 1H), 7.24 (d, J=2.8 Hz, 1H), 7.22 (t, J=2.4 Hz, 1H), 7.14 (s, 1H), 7.03 (dd, J=8.8 Hz, 2.8 Hz, 1H), 6.77-6.85 (m, 3H), 6.63-6.69 (m, 1H), 6.46 (t, J=2.4 Hz, 1H), 3.65 (s, 3H), 3.17 (s, 6H).

Example 6: 4-{2-(2-chloro-6-methylphenoxy)-5-[dimethyl(oxo)-λ⁶-sulfanylidene]aminophenyl}-6-methyl-1,6-dihydro-7H-pyrrolo[2,3-c]pyridin-7-one

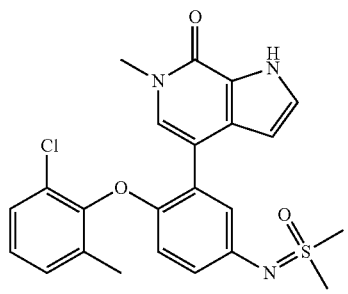 [SMILES: Cc1cccc(Cl)c1Oc1ccc(N=S(C)(C)=O)cc1-c1cn(C)c(=O)c2[nH]ccc12]

Step A: N-{3-bromo-4-[4-(2-chloro-6-methylphenoxy]phenyl}-S,S-dimethylsulfonimide

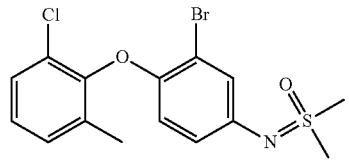 [SMILES: Cc1cccc(Cl)c1Oc1ccc(N=S(C)(C)=O)cc1Br]

The product was obtained by referring to steps A-D in Example 1, starting from 2-bromo-1-fluoro-4-nitrobenzene and 2-chloro-6-methylphenol.

¹H NMR (400 MHz, CDCl₃) δ 7.37 (d, J=2.4 Hz, 1H), 7.27-7.31 (m, 1H), 7.15-7.17 (m, 1H), 7.07-7.10 (m, 1H), 6.83 (dd, J=8.8 Hz, 2.4 Hz, 1H), 6.26 (d, J=8.8 Hz, 1H), 3.14 (s, 6H), 2.18 (s, 3H).

Step B: 4-{2-(2-chloro-6-methylphenoxy)-5-[dimethyl(oxo)-λ⁶-sulfanylidene]aminophenyl}-6-methyl-1,6-dihydro-7H-pyrrolo[2,3-c]pyridin-7-one

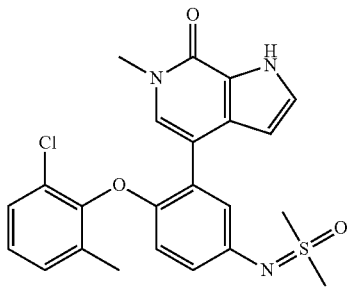 [SMILES: Cc1cccc(Cl)c1Oc1ccc(N=S(C)(C)=O)cc1-c1cn(C)c(=O)c2[nH]ccc12]

To a mixed solvent of 1,4-dioxane (10 mL) and water (1 mL) were sequentially added N-{3-bromo-4-[4-(2-chloro-6-methylphenoxy)phenyl}-S,S-dimethylsulfonimide (80 mg), 6-methyl-4-(4,4,5,5-tetramethyl-1,3,2-dioxaborolan-2-yl)-1,6-dihydro-7H-pyrrolo[2,3-c]pyridin-7-one (58 mg), potassium phosphate (90 mg), and PdCl₂(dppf) (8 mg) under N₂ atmosphere, and the mixture was heated to 85° C. and stirred overnight. The reaction mixture was cooled to room temperature, filtered through diatomite and rinsed with ethyl acetate, and the filtrate was evaporated to dryness. The residue was separated by a preparative thin-layer plate (100% EtOAc) to give the product (70 mg).

¹H NMR (400 MHz, CDCl₃) δ 10.32 (brs, 1H), 7.31 (s, 1H), 7.28 (d, J=1.2 Hz, 1H), 7.25-7.26 (m, 1H), 7.24 (d, J=2.8 Hz, 1H), 7.09-7.11 (m, 1H), 7.03-7.05 (m, 1H), 6.89 (dd, J=8.8 Hz, 2.8 Hz, 1H), 6.54-6.55 (m, 1H), 6.34 (d, J=8.8 Hz, 1H), 3.71 (s, 3H), 3.15 (s, 6H), 2.07 (s, 3H).

Example 7: 4-{2-(2-chloro-6-methylphenoxy)-5-{[dimethyl(oxo)-λ⁶-sulfanylidene]amino}phenyl}-N-ethyl-6-methyl-7-oxo-6,7-dihydro-1H-pyrrolo[2,3-c]pyridine-2-carboxamide

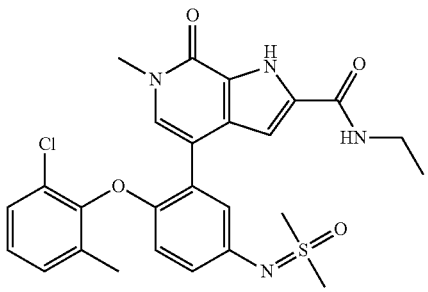 [SMILES: CCNC(=O)c1cc2c(-c3cc(N=S(C)(C)=O)ccc3Oc3c(C)cccc3Cl)cn(C)c(=O)c2[nH]1]

To a mixed solvent of 1,4-dioxane (10 mL) and water (1 mL) were sequentially added N-{3-bromo-4-[4-(2-chloro-6-methylphenoxy]phenyl}-S,S-dimethylsulfonimide (34 mg), N-ethyl-6-methyl-7-oxo-4-(4,4,5,5-tetramethyl-1,3,2-dioxaborolan-2-yl)-6,7-dihydro-1H-pyrrolo[2,3-c]pyridine-2-carboxamide (30 mg), potassium phosphate (42 mg), and PdCl₂(dppf) (3.7 mg) under N₂ atmosphere, and the mixture was heated to 85° C. and stirred overnight. The reaction mixture was cooled to room temperature, filtered through diatomite and rinsed with ethyl acetate, and the filtrate was evaporated to dryness. The residue was separated by a preparative thin-layer plate (100% EtOAc) to give the product (20 mg).

¹H NMR (400 M Hz, CDCl₃) δ 11.62 (brs, 1H), 7.45-7.50 (m, 1H), 7.37 (s, 1H), 7.27-7.29 (m, 1H), 7.23-7.26 (m, 1H), 7.11-7.12 (in, 2H), 7.03-7.07 (m, 1H), 6.93 (dd, J=8.8 Hz, 2.4 Hz, 1H), 6.34 (d, 1H), 3.74 (s, 3H), 3.51 (q, J=6.4 Hz, 2H), 3.17 (s, 6H), 2.07 (s, 3H), 1.25 (t, J=6.4 Hz, 3H).

Example 8: 4-{2-(2,4-difluorophenyl)amino-5-[dimethyl(oxo)-λ⁶-sulfanylidene]aminophenyl}-6-methyl-1,6-dihydro-7H-pyrrolo[2,3-c]pyridin-7-one

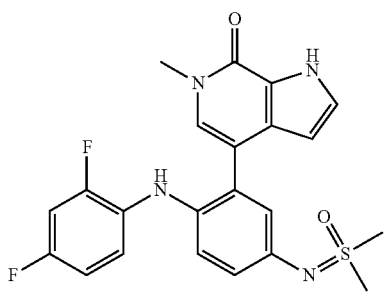 [SMILES: Cn1cc(-c2cc(N=S(C)(C)=O)ccc2Nc2ccc(F)cc2F)c2cc[nH]c2c1=O]

Step A: 2-bromo-4-nitro-N-(2,4-difluorophenyl)aniline

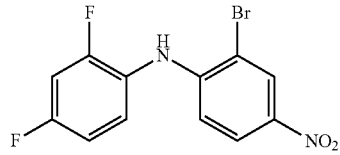 [SMILES: O=[N+]([O-])c1ccc(Nc2ccc(F)cc2F)c(Br)c1]

The product (2.5 g) was obtained by referring to step A in Example 1, starting from 2-bromo-1-fluoro-4-nitrobenzene and 2,4-difluoroaniline.

¹H NMR (400 MHz CDCl₃) δ 8.47 (d, J=2.8 Hz, 1H), 8.05 (dd, J=9.2 Hz, 2.8 Hz, 1H), 7.34-7.38 (m, 1H), 6.96-7.03 (m, 1H), 6.68-6.80 (m, 2H), 3.53 (brs, 1H).

Step B: 2-bromo-4-nitro-N-(2,4-difluorophenyl)-N-tert-butyloxycarbonylaniline

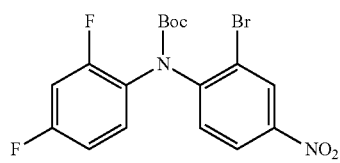 [SMILES: CC(C)(C)OC(=O)N(c1ccc(F)cc1F)c1ccc([N+](=O)[O-])cc1Br]

At 0° C., to a solution of 2-bromo-4-nitro-N-(2,4-difluorophenyl)aniline (1.60 g) in acetonitrile (50 mL) were sequentially added di-tert-butyl dicarbonate (1.56 g) and DMAP (0.92 g), and the mixture was warmed to room temperature and stirred overnight. The reaction mixture was evaporated to dryness under reduced pressure. The residue was dissolved in ethyl acetate, and washed sequentially with a 1 M aqueous HCl solution and saturated brine, and dried over anhydrous sodium sulfate. After suction filtration, the filtrate was concentrated under reduced pressure. The residue was purified by silica gel column chromatography (EtOAc/PE=1/4) to give the product (2.0 g).

¹H NMR (400 MHz, CDCl₃) δ 8.43 (s, 1H), 8.13 (dd, J=8.8 Hz, 2.4 Hz, 1H), 7.43 (d, J=8.8 Hz 1H), 7.31-7.37 (m, 1H), 6.81-6.93 (m, 2H), 1.35 (s, 9H).

Step C: 2-bromo-4-amino-N-(2,4-difluorophenyl)-N-tert-butyloxycarbonylaniline

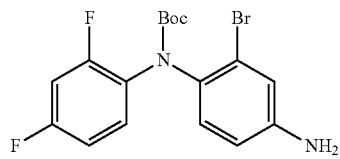 [SMILES: CC(C)(C)OC(=O)N(c1ccc(F)cc1F)c1ccc(N)cc1Br]

To a solution of 2-bromo-4-nitro-N-(2,4-difluorophenyl)-N-tert-butoxycarbonylaniline (2.0 g) in ethanol (20 mL) was added a saturated aqueous ammonium chloride solution (1 mL) at room temperature, followed by addition of zinc powder (1.56 g) in portions, and the mixture was stirred at room temperature overnight. The reaction mixture was filtered through diatomite and washed with ethyl acetate, and the filtrate was evaporated to dryness under reduced pressure. The residue was poured into a 1 N aqueous sodium hydroxide solution and extracted 3 times with ethyl acetate. The extracts were combined, washed sequentially with water and saturated brine, dried over anhydrous sodium sulfate, and concentrated under reduced pressure to remove the solvent to give the product (0.5 g).

$^1$H NMR (400 MHz, CDCl$_3$) δ 7.21-7.41 (m, 1H), 7.07 (d, J=8.4 Hz 1H), 6.92 (d, J=2.4 Hz, 1H), 6.83-6.88 (m, 1H), 6.76-6.81 (m, 1H), 6.55 (dd, J=8.4 Hz, 2.4 Hz, 1H), 3.75 (brs, 2H), 1.43 (s, 9H).

Step D: 2-bromo-4-iodo-N-(2,4-difluorophenyl)-N-tert-butoxycarbonylaniline

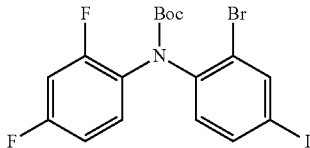

To a solution of 2-bromo-4-amino-N'-(2,4-difluorophenyl)-N'-tert-butoxycarbonylaniline (0.5 g) in acetonitrile (20 mL) were added cuprous iodide (0.48 g) and isoamyl nitrite (0.22 g) at room temperature, and the mixture was heated to 50° C. and stirred for 1 hour. The reaction mixture was filtered through diatomite, and the filtrate was evaporated to dryness under reduced pressure. The residue was purified by silica gel column chromatography (EtOAc/PE=1/4) to give the product (0.15 g).

$^1$H NMR (400 MHz, CDCl$_3$) δ 7.98 (d, J=2.0 Hz, 1H), 7.60 (dd, J=8.4 Hz, 2.0 Hz, 1H), 7.30-7.32 (m, 1H), 7.02 (d, J=8.0 Hz 1H), 6.79-6.91 (m, 2H), 1.42 (s, 9H).

Step E: N-{3-bromo-4-[N-(2,4-difluorophenyl)-N-tert-butoxycarbonylamino]phenyl}-S,S-dimethylsulfonimide

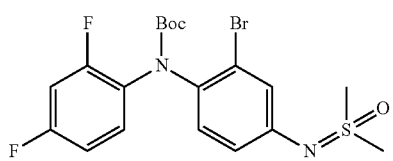 [SMILES: CC(C)(C)OC(=O)N(c1ccc(F)cc1F)c1ccc(N=S(C)(C)=O)cc1Br]

The product (120 mg) was obtained in the same manner as step D in Example 1.

$^1$H NMR (400 MHz, CDCl$_3$) δ 7.31-7.48 (m, 2H), 7.15 (d, J=8.4 Hz, 1H), 6.97 (dd, J=8.4 Hz, 2.4 Hz, 1H), 6.77-6.89 (m, 2H), 3.15 (s, 6H), 1.43 (s, 9H).

Step F: 4-{2-[N-(2,4-difluorophenyl)-N-tert-butoxycarbonylamino]-5-{[dimethyl(oxo)-λ$^6$-sulfanylidene]amino}phenyl}-6-methyl-1,6-dihydro-7H-pyrrolo[2,3-c]pyridin-7-one

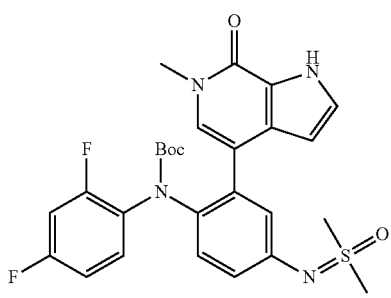 [SMILES: Cn1cc(-c2cc(N=S(C)(C)=O)ccc2N(C(=O)OC(C)(C)C)c2ccc(F)cc2F)c2cc[nH]c2c1=O]

The product (50 mg) was obtained in the same manner as step D in Example 2.

$^1$H NMR (400 MHz, CDCl$_3$) δ 10.73 (brs, 1H), 7.35-7.50 (m, 1H), 7.08-7.16 (m, 3H), 6.80-7.00 (m, 1H), 6.45-6.54 (m, 3H), 6.09 (s, 1H), 3.60 (s, 3H), 3.17 (s, 6H), 1.41 (s, 9H).

Step G: 4-{2-(2,4-difluorophenyl)amino-5-[dimethyl(oxo)-λ$^6$-sulfanylidene]aminophenyl}-6-methyl-1,6-dihydro-7H-pyrrolo[2,3-c]pyridin-7-one

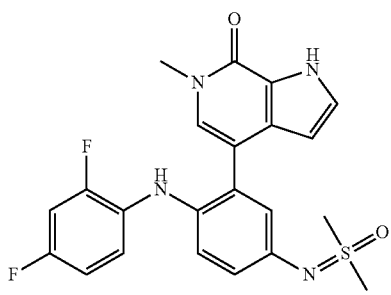 [SMILES: Cn1cc(-c2cc(N=S(C)(C)=O)ccc2Nc2ccc(F)cc2F)c2cc[nH]c2c1=O]

To a solution of 4-{2-[N-(2,4-difluorophenyl)-N-tert-butoxycarbonylamino]-5-{[dimethyl(oxo)-λ$^6$-sulfanylidene]amino}phenyl}-6-methyl-1,6-dihydro-7H-pyrrolo[2,3-c]pyridin-7-one (50 mg) in dioxane (2 mL) was slowly added concentrated hydrochloric acid (1 mL) at 0° C., and the mixture was warmed naturally to room temperature and stirred for 1 hour. The solvent was removed by rotary evaporation, and the residue was purified by a thin-layer silica gel plate (100% EtOAc) to give the product (12 mg).

$^1$H NMR (400 MHz, CDCl$_3$) δ 11.08 (brs, 1H), 7.24-7.26 (m, 1H), 7.03-7.18 (m, 4H), 6.97 (s, 1H), 6.73-6.79 (m, 2H), 6.22 (d, J=2.0 Hz, 1H), 5.39 (s, 1H), 3.67 (s, 3H), 3.21 (s, 6H).

Example 9: 4-{5-{[dimethyl(oxo)-λ⁶-sulfanylidene]amino}-2-[(2-methyl-pyridin-3-yl)oxy]phenyl}-6-methyl-1,6-dihydro-7H-pyrrolo[2,3-c]pyridin-7-one

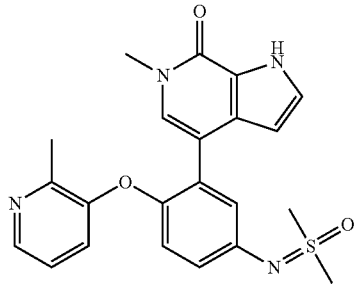 [SMILES: Cc1ncccc1Oc1ccc(N=S(C)(C)=O)cc1-c1cn(C)c(=O)c2[nH]ccc12]

Step A: N-{3-bromo-4-[(2-methylpyridin-3-yl)oxy]phenyl}-S,S-dimethylsulfonimide

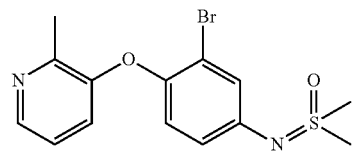 [SMILES: Cc1ncccc1Oc1ccc(N=S(C)(C)=O)cc1Br]

The product was obtained by referring to steps A-D in Example 1, starting from 2-methyl-3-hydroxypyridine and 2-bromo-1-fluoro-4-nitrobenzene.

¹H NMR (400 MHz, CDCl₃) δ 8.22 (d, J=1.6 Hz, 1H), 7.39 (d, J=2.8 Hz, 1H), 7.01-7.06 (m, 2H), 6.93 (dd, J=8.0 Hz, 1.2 Hz, 1H), 6.82 (d, J=8.4 Hz, 1H), 3.16 (s, 6H), 2.60 (s, 3H).

Step B: 4-{5-{[dimethyl(oxo)-λ⁶-sulfanylidene]amino}-2-[(2-methyl-pyridin-3-yl)oxy]phenyl}-6-methyl-1,6-dihydro-7H-pyrrolo[2,3-c]pyridin-7-one

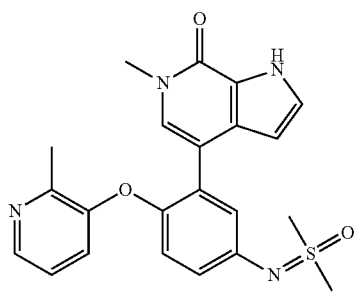 [SMILES: Cc1ncccc1Oc1ccc(N=S(C)(C)=O)cc1-c1cn(C)c(=O)c2[nH]ccc12]

The product (15 mg) was obtained in the same manner as step D in Example 2.

¹H NMR (400 MHz, CDCl₃) δ 10.78 (brs, 1H), 8.08 (d, J=3.6 Hz, 1H), 7.27 (s, 1H), 7.23-7.24 (m, 1H), 7.07-7.10 (dd, J=8.4 Hz, 2.4 Hz, 1H), 7.01 (s, 1H), 6.85-6.92 (m, 3H), 6.40-6.42 (m, 1H), 3.62 (s, 3H), 3.20 (s, 6H), 2.39 (s, 3H).

Example 10: 4-{5-{[dimethyl(oxo)-λ⁶-sulfanylidene]amino}-2-(4-fluoro-2,6-dimethylphenoxy)phenyl}-N-ethyl-6-methyl-7-oxo-6,7-dihydro-1H-pyrrolo[2,3-c]pyridine-2-carboxamide

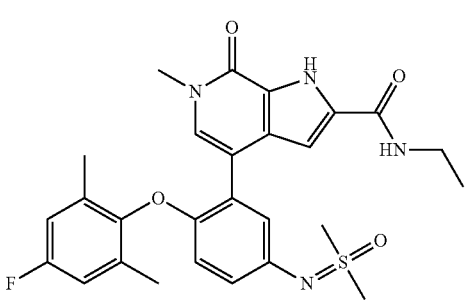

Step A: 4-fluoro-2,6-dimethylphenol

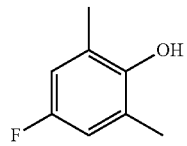

2-bromo-5-fluoro-1,3-dimethylbenzene (18.8 g) was dissolved in anhydrous tetrahydrofuran (150 mL), and a 2.5 M solution of n-butyllithium in n-hexane (45 mL) was added dropwise at −78° C. over 15 minutes under nitrogen atmosphere. The mixture was stirred at −78° C. for 20 minutes, added with trimethyl borate (11.5 g) dropwise at −78° C., slowly warmed to room temperature, and stirred for another 30 minutes. The reaction mixture was cooled to 0° C., added with a 1 N aqueous sodium hydroxide solution (148 mL), followed by a 50% aqueous hydrogen peroxide solution (70 mL). The resulting mixture was warmed to room temperature and stirred for 1 hour, added with a 1 N hydrochloric acid solution to adjust the pH to 4-5, added with a saturated aqueous sodium sulfite solution (100 mL), and extracted with ether. The extract was washed with saturated brine, dried over anhydrous sodium sulfate, and concentrated under reduced pressure to remove the solvent to give the product (12 g).

¹H NMR (400 MHz CDCl₃) δ 6.66 (d, J=9.2 Hz, 2H), 4.38-4.82 (brs, 1H), 2.21 (s, 6H).

Step B: 2-(2-bromo-4-nitrophenoxy)-5-fluoro-1,3-dimethylbenzene

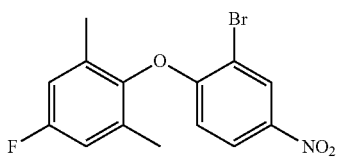 [SMILES: Cc1cc(F)cc(C)c1Oc1ccc([N+](=O)[O-])cc1Br]

to a solution of 4-fluoro-2-dimethylphenol (1.00 g) in DMSO (20 mL) were added 2-bromo-1-fluoro-4-nitrobenzene (686 mg) and cesium carbonate (2.2 g) at 0° C., and the mixture was heated to 100° C. and stirred for 2 hours. The reaction mixture was poured into water, stirred for 15 minutes, and filtered, and the solid was collected to give the product (1.4 g).

¹H NMR (400 MHz CDCl₃) δ 8.56 (d, J=2.4 Hz, 1H), 8.05 (dd, J=8.8 Hz, 2.4 Hz, 1H), 6.86 (d, J=8.8 Hz, 2H), 6.46 (d, J=8.8 Hz, 1H), 2.11 (s, 6H).

Step C: 3-bromo-4-(4-fluoro-2,6-dimethylphenoxy)aniline

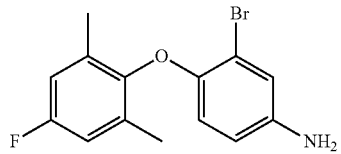

To a solution of 2-(2-bromo-4-nitrophenoxy)-5-fluoro-1,3-dimethylbenzene (1.4 g) in ethanol (20 mL) and acetic acid (5 mL) was added zinc powder (1.34 g) in portions at room temperature over about 30 minutes, and the mixture was stirred at room temperature overnight. The reaction mixture was diluted with dichloromethane, and filtered, and the filtrate was evaporated to dryness under reduced pressure. The residue was poured into a saturated aqueous sodium bicarbonate solution and extracted 3 times with ethyl acetate. The extracts were combined, washed sequentially with water and saturated brine, dried over anhydrous sodium sulfate, and concentrated under reduced pressure to remove the solvent to give the product (0.82 g).

¹H NMR (400 MHz, CDCl₃) δ 6.98 (d, J=2.4 Hz, 1H), 6.78 (d, J=8.8 Hz, 2H), 6.43 (dd, J=8.8 Hz, 2.8 Hz, 1H), 6.15 (d, J=8.8 Hz, 1H), 3.48 (s, 2H), 2.12 (s, 6H).

Step D: 2-(2-bromo-4-iodophenoxy)-5-fluoro-1,3-dimethylbenzene

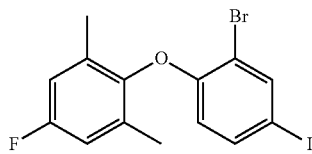 [SMILES: Cc1cc(F)cc(C)c1Oc1ccc(I)cc1Br]

Under an ice bath, to a solution of 3-bromo-4-(4-fluoro-2,6-dimethylphenoxy)aniline (0.20 g) in 33% sulfuric acid (10 mL) and acetonitrile (10 mL) was slowly added a solution of sodium nitrite (58 mg) in water (1 mL) dropwise over about 5 minutes. After 15 minutes, a solution of potassium iodide (425 mg) in water (3 mL) was slowly added dropwise, and the mixture was warmed naturally to room temperature and stirred for 1 hour. The reaction mixture was poured into a saturated aqueous sodium bicarbonate solution (60 mL) containing ice. The resulting mixture was added with a saturated aqueous sodium thiosulfate solution (10 mL), and extracted 3 times with ethyl acetate. The extracts were combined, washed sequentially with water and saturated brine, dried over anhydrous sodium sulfate, and concentrated under reduced pressure to remove the solvent to give the product (269 mg).

Step E: N-[3-bromo-4-(4-fluoro-2,6-dimethylphenoxy)phenyl]-S,S-dimethylsulfonimide

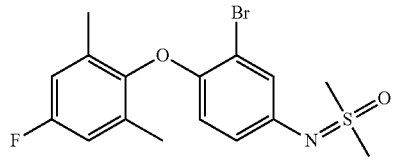 [SMILES: Cc1cc(F)cc(C)c1Oc1ccc(N=S(C)(C)=O)cc1Br]

To anhydrous dioxane (10 mL) were sequentially added 2-(2-bromo-4-iodophenoxy)-5-fluoro-1,3-dimethylbenzene (50 mg), dimethylsulfoximine (13 mg), cesium carbonate (59 mg), Xantphos (5 mg, 0.075 eq), and Pd₂(dba)₃ (3 mg) under N₂ atmosphere, and the mixture was heated to 100° C. and stirred for 3 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (PE/EtOAc=1/1) to give the product (25 mg).

¹H NMR (400 MHz, CDCl₃) δ 7.36 (d, J=2.4 Hz, 1H), 6.78-6.83 (m, 3H), 6.22 (d, J=8.8 Hz, 1H), 3.13 (s, 6H), 2.12 (s, 6H).

Step F: 4-{5-{[dimethyl(oxo)-λ⁶-sulfanylidene]amino}-2-(4-fluoro-2,6-dimethylphenoxy)phenyl}-N-ethyl-6-methyl-7-oxo-6,7-dihydro-1H-pyrrolo[2,3-c]pyridine-2-carboxamide

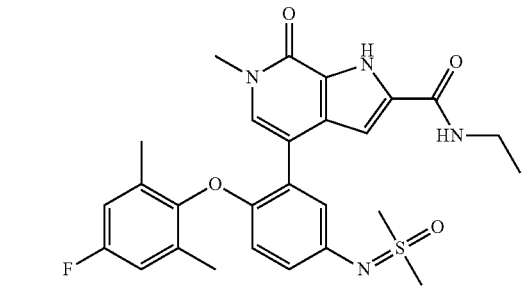 [SMILES: CCNC(=O)c1cc2c(-c3cc(N=S(C)(C)=O)ccc3Oc3c(C)cc(F)cc3C)cn(C)c(=O)c2[nH]1]

To an 80% aqueous dioxane solution (10 mL) were sequentially added N-[3-bromo-4-(4-fluoro-2,6-dimethylphenoxy) phenyl]-S,S-dimethylsulfonimide (25 mg), N-ethyl-6-methyl-7-oxo-4-(4,4,5,5-tetramethyl-1,3,2-dioxaborolan-2-yl)-6,7-dihydro-1H-pyrrolo[2,3-c]pyridine-2-carboxamide (25 mg), potassium phosphate (25 mg), and PdCl₂(dppf) (4 mg) under N₂ atmosphere, and the mixture was heated to 80° C. and stirred for 6 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (MeOH/DCM=1/25) to give the product (18 mg).

¹H NMR (400 MHz, CDCl₃) δ 10.75 (s, 1H), 7.24 (s, 2H), 6.88-6.92 (m, 2H), 6.75-6.84 (m, 3H), 6.34 (d, J=8.8 Hz, 1H), 3.72 (s, 3H), 3.48-3.56 (m, 2H), 3.16 (s, 6H), 2.07 (s, 6H), 1.26 (t, J=7.2 Hz, 3H).

Example 11: 4-{5-{[dimethyl(oxo)-λ⁶-sulfanylidene]amino}-2-(4-fluoro-2,6-dimethylphenoxy)phenyl}-6-methyl-1,6-dihydro-7H-pyrrolo[2,3-c]pyridin-7-one

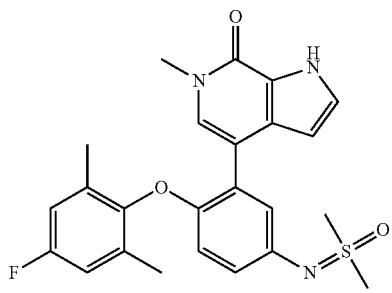 [SMILES: Cc1cc(F)cc(C)c1Oc1ccc(N=S(C)(C)=O)cc1-c1cn(C)c(=O)c2[nH]ccc12]

Step A: 4-{5-{[dimethyl(oxo)-λ⁶-sulfanylidene]amino}-2-(4-fluoro-2,6-dimethylphenoxy)phenyl}-6-methyl-1-tosyl-1,6-dihydro-7H-pyrrolo[2,3-c]pyridin-7-one

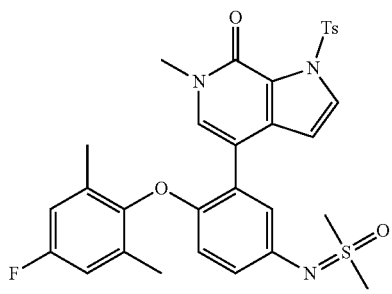 [SMILES: Cc1ccc(S(=O)(=O)n2ccc3c(-c4cc(N=S(C)(C)=O)ccc4Oc4c(C)cc(F)cc4C)cn(C)c(=O)c32)cc1]

To an 80% aqueous dioxane solution (10 mL) were sequentially added N-[3-bromo-4-(4-fluoro-2,6-dimethylphenoxy) phenyl]-S,S-dimethylsulfonimide (26 mg), 6-methyl-4-(4,4,5,5-tetramethyl-1,3,2-dioxaborolan-2-yl)-1-tosyl-1,6-dihydro-7H-pyrrolo[2,3-c]pyridin-7-one (17 mg), potassium phosphate (28 mg), and PdCl₂(dppf) (5 mg) under N₂ atmosphere, and the mixture was heated to 80° C. and stirred for 6 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (MeOH/DCM=1/25) to give the product (24 mg).

¹H NMR (400 MHz, CDCl₃) δ 8.06 (d, J=8.8 Hz, 2H), 7.89 (d, J=3.6 Hz, 1H), 7.32 (d, J=8.8 Hz, 2H), 7.17 (s, 1H), 7.06 (d, J=2.8 Hz, 1H), 6.88 (dd, J=8.8 Hz, 2.8 Hz, 1H), 6.75 (d, J=8.8 Hz, 2H), 6.50 (d, J=3.6 Hz, 1H), 6.30 (d, J=8.8 Hz, 1H), 3.57 (s, 3H), 3.14 (s, 6H), 2.41 (s, 3H), 2.03 (s, 6H).

Step B: 4-{5-{[dimethyl(oxo)-λ⁶-sulfanylidene]amino}-2-(4-fluoro-2,6-dimethylphenoxy)phenyl}-6-methyl-1,6-dihydro-7H-pyrrolo[2,3-c]pyridin-7-one

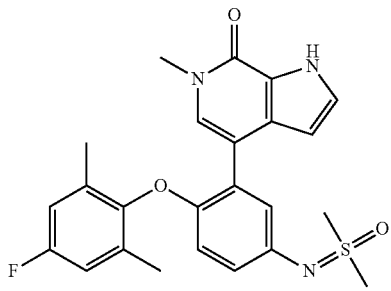

To a mixed solution of ethanol and 1 N NaOH (3 mL:3 mL) was added 4-{5-{[dimethyl(oxo)-λ⁶-sulfanylidene]amino}-2-(4-fluoro-2,6-dimethylphenoxy)phenyl}-6-methyl-1-tosyl-1,6-dihydro-7H-pyrrolo[2,3-c]pyridin-7-one (24 mg), and the mixture was heated to 70° C. and stirred for 1 hour. The reaction mixture was cooled to room temperature, concentrated under reduced pressure, added with a saturated aqueous disodium hydrogen phosphate solution, and extracted with dichloromethane. The extract was washed with water and saturated brine, dried over anhydrous sodium sulfate, and concentrated under reduced pressure. The residue was separated by a preparative thin-layer plate (MeOH/DCM=1/20) to give the product (17 mg, 99%).

¹H NMR (400 MHz, CDCl₃) δ 9.78 (s, 1H), 7.23-7.25 (m, 1H), 7.21 (d, J=2.4 Hz, 1H), 7.16 (s, 1H), 6.88 (dd, J=8.8 Hz, 2.8 Hz, 1H), 6.74 (d, J=8.8 Hz, 2H), 6.45-6.47 (m, 1H), 6.32 (d, J=8.8 Hz, 1H), 3.70 (s, 3H), 3.14 (s, 6H), 2.06 (s, 6H).

Example 12: 4-{5-{[dimethyl(oxo)-λ⁶-sulfanylidene]amino}-2-[(tetrahydrofuran-3-yl)methoxy]phenyl}-6-methyl-1,6-dihydro-7H-pyrrolo[2,3-c]pyridin-7-one

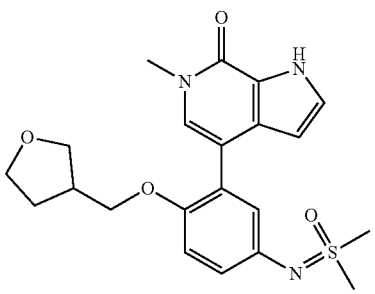 [SMILES: Cn1cc(-c2cc(N=S(C)(C)=O)ccc2OCC2CCOC2)c2cc[nH]c2c1=O]

Step A: 3-[(2-bromo-4-nitrophenoxy)methyl]tetrahydrofuran

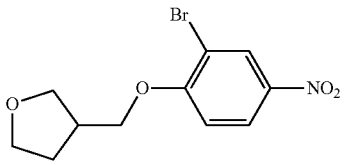 [SMILES: O=[N+]([O-])c1ccc(OCC2CCOC2)c(Br)c1]

(Tetrahydrofuran-3-yl)methanol (460 mg) and 2-bromo-1-fluoro-4-nitrobenzene (1.0 g) were dissolved in DMSO (20 mL), and cesium carbonate (2.2 g) was added. The mixture was stirred at 110° C. for 2 hours, cooled to room temperature, added with a large amount of water to quench the reaction, and extracted with ethyl acetate. The extract was washed several times with water, and the solvent was removed under reduced pressure to give the oily product (1.2 g).

$^1$H NMR (400 MHz, CDCl$_3$) δ 8.48 (d, J=2.4 Hz, 1H), 8.20 (dd, J=9.2 Hz, 2.8 Hz, 1H), 6.94 (d, J=9.2 Hz, 1H), 4.03-4.11 (m, 2H), 3.92-3.98 (m, 2H), 3.76-3.85 (m, 2H), 2.81-2.89 (m, 1H), 2.14-2.22 (m, 1H), 1.76-1.85 (m, 1H).

Step B: 3-bromo-4-[(tetrahydrofuran-3-yl)methoxy]aniline

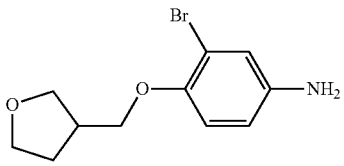

3-[(2-bromo-4-nitrophenoxy)methyl]tetrahydrofuran (100 mg) was dissolved in ethanol (20 mL), and acetic acid (96 mg) and zinc powder (108 mg) were added respectively. The mixture was stirred at room temperature for 1 hour, filtered through diatomite, added with a saturated aqueous sodium carbonate solution to adjust pH to 9, and extracted with ethyl acetate. The extract was concentrated to give an oily crude product, which was rinsed with ethyl acetate, and purified by flash column chromatography to give the pure product (90 mg).

$^1$H NMR (400 MHz, CDCl$_3$) δ 6.81 (d, J=2.8 Hz, 1H), 6.75 (d, J=8.8 Hz, 1H), 6.57 (dd, J=8.8 Hz, 2.8 Hz, 1H), 3.37-3.95 (m, 6H), 3.40-3.62 (brs, 2H), 2.70-2.78 (m, 1H), 2.07-2.12 (m, 1H), 1.74-1.79 (m, 1H).

Step C: 3-[(2-bromo-4-iodophenoxy)methyl]-tetrahydrofuran

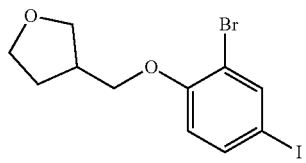 [SMILES: Brc1cc(I)ccc1OCC1CCOC1]

Under an ice bath, to a solution of 3-bromo-4-[(tetrahydrofuran-3-yl)methoxy]aniline (1.9 g) in 33% sulfuric acid (30 mL) and acetonitrile (30 mL) was slowly added a solution of sodium nitrite (626 mg) in water (1 mL) over about 5 minutes. After 15 minutes, a solution of potassium iodide (6.8 g) in water (10 mL) was slowly added dropwise. And after completion of the addition, the mixture was warmed naturally to room temperature and stirred for 1 hour. The reaction mixture was poured into a saturated aqueous sodium bicarbonate solution (60 mL) containing ice. The resulting mixture was added with a saturated sodium thiosulfate solution (30 mL), and extracted with ethyl acetate. The extracts were combined, washed sequentially with water and saturated brine, dried over anhydrous sodium sulfate, and concentrated under reduced pressure to remove the solvent, and the residue was separated by silica gel column chromatography (PE/EtOAc=5/1) to give the product (1.5 g).

$^1$H NMR (400 MHz, CDCl3) δ 7.82 (d, J=2.0 Hz, 1H), 7.52 (dd, J=8.8 Hz, 2.0 Hz, 1H), 6.64 (d, J=8.8 Hz, 1H), 3.89-3.97 (m, 4H), 3.73-3.83 (m, 2H), 2.75-2.82 (m, 1H), 2.09-2.17 (m, 1H), 1.57-2.04 (m, 1H).

Step D: N-{3-bromo-4-[(tetrahydrofuran-3-yl)methoxy]phenyl}-S,S-dimethylsulfonimide

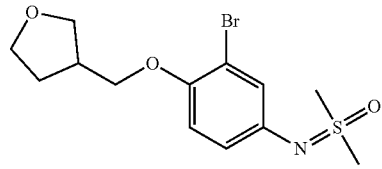 [SMILES: CS(C)(=O)=Nc1ccc(OCC2CCOC2)c(Br)c1]

To anhydrous dioxane (10 mL) were sequentially added 3-[(2-bromo-4-iodophenoxy)methyl]-tetrahydrofuran (108 mg), dimethylsulfoximine (32 mg, 1.2 eq), cesium carbonate (456 mg), Xantphos (12 mg), and Pd$_2$(dba)$_3$ (7 mg) under N$_2$ atmosphere, and the mixture was heated to 100° C. and stirred for 3 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (PE/EtOAc=3/1) to give the product (51 mg).

$^1$H NMR (400 MHz, CDCl$_3$) δ 7.29 (d, J=2.4 Hz, 1H), 6.97 (dd, J=8.8 Hz, 2.4 Hz, 1H), 6.78 (d, J=8.8 Hz, 1H), 3.86-3.96 (m, 4H), 3.74-3.82 (m, 2H), 3.12 (s, 6H), 2.74-2.8 (m, 1H), 2.08-2.16 (m, 1H), 1.74-1.83 (m, 1H).

Step E: 4-{5-{[dimethyl(oxo)-λ$^6$-sulfanylidene]amino}-2-[(tetrahydrofuran-3-yl)methoxy]phenyl}-6-methyl-1-tosyl-1,6-dihydro-7H-pyrrolo[2,3-c]pyridin-7-one

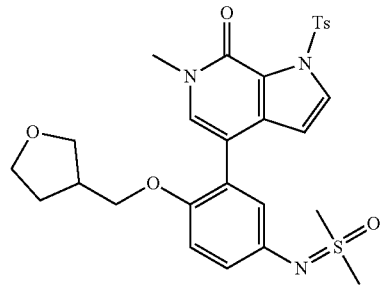 [SMILES: Cc1ccc(S(=O)(=O)n2ccc3c(-c4cc(N=S(C)(C)=O)ccc4OCC4CCOC4)cn(C)c(=O)c32)cc1]

To an 80% aqueous dioxane solution (10 mL) were sequentially added N-{3-bromo-4-[(tetrahydrofuran-3-yl)methoxy]phenyl}-S,S-dimethylsulfonimide (50 mg), 6-methyl-4-(4,4,5,5-tetramethyl-1,3,2-dioxaborolan-2-yl)-1-tosyl-1,6-dihydro-7H-pyrrolo[2,3-c]pyridin-7-one (37 mg), potassium phosphate (60 mg), and PdCl$_2$(dppf) (10 mg) under N$_2$ atmosphere, and the mixture was heated to 80° C. and stirred for 6 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (DCM/MeOH=30/1) to give the product (36 mg).

$^1$H NMR (400 MHz, CDCl$_3$) δ 8.02 (d, J=8.4 Hz, 2H), 7.87 (d, J=3.6 Hz, 1H), 7.32 (d, J=8.4 Hz, 2H), 7.07 (s, 1H), 7.04 (dd, J=8.4 Hz, 2.8 Hz, 1H), 6.99 (d, J=2.8 Hz, 1H), 6.85 (d, J=9.2 Hz, 1H), 6.37 (d, J=3.6 Hz, 1H), 3.64-3.85 (m, 5H), 3.55 (s, 3H), 3.48 (dd, J=8.8 Hz, 5.2 Hz, 1H), 3.14 (s, 6H), 2.46-2.54 (m, 1H), 2.41 (s, 3H), 1.87-1.93 (m, 1H), 1.49-1.62 (m, 1H).

Step F: 4-{5-{[dimethyl(oxo)-λ$^6$-sulfanylidene]amino}-2-[(tetrahydrofuran-3-yl)methoxy]phenyl}-6-methyl-1,6-dihydro-7H-pyrrolo[2,3-c]pyridin-7-one

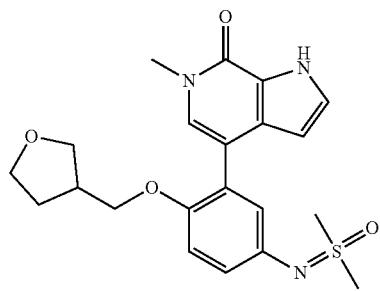 [SMILES: Cn1cc(-c2cc(N=S(C)(C)=O)ccc2OCC2CCOC2)c2cc[nH]c2c1=O]

To a mixed solution of ethanol and 1 N NaOH (3 mL:3 mL) was added 4-{5-{[dimethyl(oxo)-λ$^6$-sulfanylidene]amino}-2-[(tetrahydrofuran-3-yl)methoxy]phenyl}-6-methyl-1-tosyl-1,6-dihydro-7H-pyrrolo[2,3-c]pyridin-7-one (36 mg), and the mixture was heated to 70° C. and stirred for 1 hour. The reaction mixture was cooled to room temperature, concentrated under reduced pressure, added with a saturated aqueous disodium hydrogen phosphate solution, and extracted with dichloromethane. The extract was washed with water and saturated brine, dried over anhydrous sodium sulfate, and concentrated under reduced pressure. The residue was separated by a preparative thin-layer plate (DCM/MeOH=25/1) to give the product (20 mg).

$^1$H NMR (400 MHz, CDCl$_3$) δ 9.99 (s, 1H), 7.22 (t, J=2.4 Hz, 1H), 7.15 (d, J=2.8 Hz, 1H), 7.03-7.06 (m, 2H), 6.88 (d, J=8.4, 1H), 6.33 (t, J=2.4 Hz, 1H), 3.86 (dd, J=9.2 Hz, 6.4 Hz, 1H), 3.80 (dd, J=9.2 Hz, 7.6 Hz, 1H), 3.63-3.76 (m, 6H), 3.50 (dd, J=8.4 Hz, 5.6 Hz, 1H), 3.15 (s, 6H), 2.49-2.57 (m, 1H), 1.86-1.95 (m, 1H), 1.51-1.60 (m, 1H).

Example 13: 4-{5-{[dimethyl(oxo)-λ$^6$-sulfanylidene]amino}-2-(4-fluoro-2,6-dimethylphenoxy)phenyl}-6-methyl-7-oxo-6,7-dihydro-1H-pyrrolo[2,3-e]pyridine-2-carboxylic acid

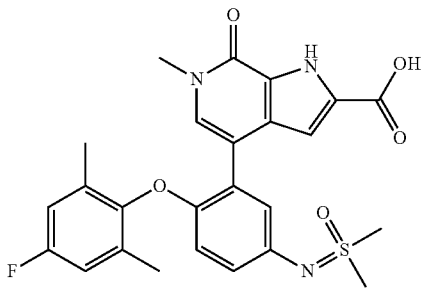

Step A: Butyl 6-methyl-7-oxo-4-(4,4,5,5-tetramethyl-1,3,2-dioxaborolan-2-yl)-1-tosyl-6,7-dihydro-1H-pyrrolo[2,3-c]pyridine-2-carboxylate

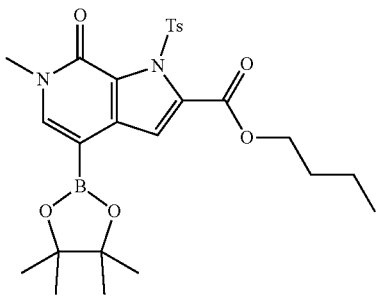 [SMILES: CCCCOC(=O)c1cc2c(B3OC(C)(C)C(C)(C)O3)cn(C)c(=O)c2n1S(=O)(=O)c1ccc(C)cc1]

To anhydrous dioxane (30 mL) were sequentially added butyl-4-bromo-6-methyl-7-oxo-1-tosyl-6,7-dihydro-1H-pyrrolo[2,3-c]pyridine-2-carboxylate (300 mg), bis(pinacolato)diboron (792 mg), anhydrous potassium acetate (304 mg), Pd$_2$(dba)$_3$ (28 mg), and x-phos (59 mg, 0.2 eq) under N$_2$ atmosphere, and the mixture was heated to 75° C. and stirred for 12 hours. The reaction mixture was cooled to room temperature, and concentrated under reduced pressure. The residue was separated by a preparative thin-layer plate (DCM/MeOH=30/1) to give the product (210 mg).

$^1$H NMR (400 MHz, CDCl$_3$) δ 8.42 (d, J=8.4 Hz, 2H), 7.59 (s, 1H), 7.37 (d, J=8.4 Hz, 2H), 7.28 (s, 1H), 4.40 (t, J=6.4 Hz, 2H), 3.57 (s, 3H), 2.43 (s, 3H), 1.75-1.83 (m, 2H), 1.43-1.53 (m, 2H), 1.27 (s, 12H), 0.98 (t, J=7.2 Hz, 3H).

Step B: Butyl 4-{5-{[dimethyl(oxo)-λ⁶-sulfanylidene]amino}-2-(4-(4-fluoro-2,6-dimethylphenoxy)phenyl}-6-methyl-7-oxo-1-tosyl-6,7-dihydro-1H-pyrrolo[2,3-c]pyridine-2-carboxylate

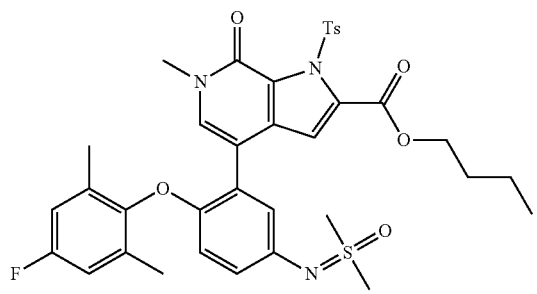 [SMILES: CCCCOC(=O)c1cc2c(-c3cc(N=S(C)(C)=O)ccc3Oc3c(C)cc(F)cc3C)cn(C)c(=O)c2n1S(=O)(=O)c1ccc(C)cc1]

To an 80% dioxane aqueous solution (10 mL) were sequentially added N-[3-bromo-4-(4-fluoro-2,6-dimethylphenoxy)phenyl]-S,S-dimethylsulfonimide (83 mg), butyl 6-methyl-7-oxo-4-(4,4,5,5-tetramethyl-1,3,2-dioxaborolan-2-yl)-1-tosyl-6,7-dihydro-1H-pyrrolo[2,3-c]pyridine-2-carboxylate (160 mg), potassium phosphate (93 mg), and PdCl₂(dppf) (16 mg) under N₂ atmosphere, and the mixture was heated to 80° C. and stirred for 6 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (DCM/MeOH=25/1) to give the product (44 mg).

¹H NMR (400 MHz, CDCl₃) δ 8.52 (d, J=8.4 Hz, 2H), 7.38 (d, J=8.4 Hz, 2H), 7.23 (s, 1H), 7.02 (d, J=2.8 Hz, 1H), 6.96 (s, 1H), 6.91 (dd, J=8.4 Hz, 2.8 Hz, 1H), 6.76 (s, 1H), 6.74 (s, 1H), 6.31 (d, J=8.8 Hz, 1H), 4.36 (t, J=6.8 Hz, 2H), 3.63 (s, 3H), 3.14 (s, 6H), 2.44 (s, 3H), 2.03 (s, 6H), 1.70-1.76 (m, 2H), 1.41-1.47 (m, 2H), 0.96 (t, J=7.6 Hz, 3H).

Step C: 4-{5-{[dimethyl(oxo)-λ⁶-sulfanylidene]amino}-2-(4-fluoro-2,6-dimethylphenoxy)phenyl}-6-methyl-7-oxo-6,7-dihydro-1H-pyrrolo[2,3-c]pyridine-2-carboxylic acid

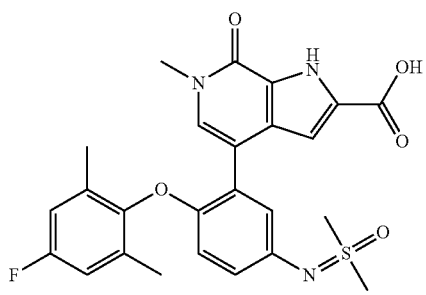 [SMILES: Cc1cc(F)cc(C)c1Oc1ccc(N=S(C)(C)=O)cc1-c1cn(C)c(=O)c2[nH]c(C(=O)O)cc12]

To a mixed solution of ethanol and 1 N NaOH (3 mL:3 mL) was added butyl 4-{5-{[dimethyl(oxo)-λ⁶-sulfanylidene]amino}-2-(4-4-fluoro-2,6-dimethylphenoxy)phenyl}-6-methyl-7-oxo-1-tosyl-6,7-dihydro-1H-pyrrolo[2,3-c]pyridine-2-carboxylate (20 mg), and the mixture was heated to 70° C. and stirred for 1 hour. The reaction mixture was cooled to room temperature, concentrated under reduced pressure, added with a saturated aqueous disodium hydrogen phosphate solution, and extracted with dichloromethane. The extract was washed with water and saturated brine, dried over anhydrous sodium sulfate, and concentrated under reduced pressure to give the product (12 mg).

¹H NMR (400 MHz, CDCl₃) δ 13.21 (s, 1H), 7.22 (s, 2H), 7.19 (d, J=2.8 Hz, 1H), 6.94 (dd, J=8.8 Hz, 2.8 Hz, 1H), 6.77 (s, 1H), 6.75 (s, 1H), 6.34 (d, J=8.8 Hz, 1H), 3.78 (s, 3H), 3.17 (s, 6H), 2.09 (s, 6H).

Example 14: Ethyl 4-{5-{[dimethyl(oxo)-λ⁶-sulfanylidene]amino}-2-(4-fluoro-2,6-dimethylphenoxy)phenyl}-6-methyl-7-oxo-6,7-dihydro-1H-pyrrolo[2,3-c]pyridine-2-carboxylate

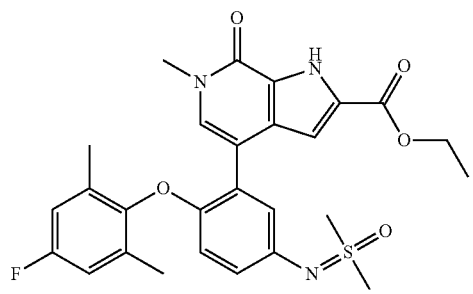 [SMILES: CCOC(=O)c1cc2c(-c3cc(N=S(C)(C)=O)ccc3Oc3c(C)cc(F)cc3C)cn(C)c(=O)c2[nH]1]

4-{5-{[dimethyl(oxo)-λ⁶-sulfanylidene]amino}-2-(4-fluoro-2,6-dimethylphenoxy)phenyl}-6-methyl-7-oxo-6,7-dihydro-1H-pyrrolo[2,3-c]pyridine-2-carboxylic acid (8 mg) was dissolved in ethanol (10 mL), and concentrated sulfuric acid (0.3 mL) was added. The mixture was heated to 80° C. and stirred for 2 hours. The reaction mixture was cooled to room temperature, concentrated under reduced pressure, added with a 1 N aqueous sodium hydroxide solution to adjust the pH to 9, and extracted with dichloromethane. The extract was washed with water and saturated brine, dried over anhydrous sodium sulfate, and concentrated under reduced pressure. The residue was separated by a preparative thin-layer plate (DCM/MeOH=30/1) to give the product (7 mg).

¹H NMR (400 MHz, CDCl₃) δ 10.15 (s, 1H), 7.12-7.15 (m, 3H), 6.92 (dd, J=8.4 Hz, 2.4 Hz, 1H), 6.76 (s, 1H), 6.74 (s, 1H), 6.33 (d, J=8.8 Hz, 1H), 4.37 (q, J=7.2 Hz, 2H), 3.69 (s, 3H), 3.17 (s, 6H), 2.06 (s, 6H), 1.38 (t, J=7.2 Hz, 3H).

Example 15: 4-{2-(2,4-difluorophenoxy)-5-[(1-oxidotetrahydro-1λ⁶-thiophen-1-ylidene)amino]phenyl}-6-methyl-1,6-dihydro-7H-pyrrolo[2,3-c]pyridin-7-one

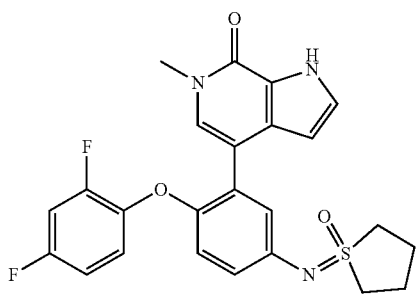 [SMILES: Cn1cc(-c2cc(N=S3(=O)CCCC3)ccc2Oc2ccc(F)cc2F)c2cc[nH]c2c1=O]

Step A: 1-iminotetrahydro-1H-1λ⁶-thiophene-1-oxide

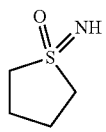

Tetramethyl sulfoxide (1.0 g) was dissolved in methanol (20 mL), and iodobenzenediacetic acid (9.3 g) and ammonium carbamate (3 g) were sequentially added. The mixture was stirred for 1 hour at 25° C., and the solvent was removed under reduced pressure. The residue was separated by silica gel column chromatography (DCM/MeOH=50/1) to give the oily product (1.1 g).

$^1$H NMR (400 MHz, CDCl$_3$) δ 3.12-3.16 (m, 4H), 2.24-2.78 (m, 4H).

Step B: 2-bromo-1-(2,4-difluorophenoxy)-4-iodobenzene

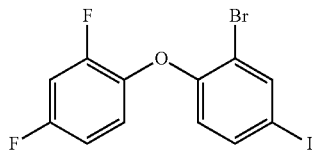 [SMILES: Fc1ccc(Oc2ccc(I)cc2Br)c(F)c1]

Under an ice bath, to a solution of 3-bromo-4-(2,4-dimethylfluorobenzene)aniline (5.0 g) in 33% sulfuric acid (70 mL) and acetonitrile (70 mL) was slowly added a solution of sodium nitrite (1.4 g) in water (20 mL) dropwise over about 30 minutes. After 30 minutes, a solution of potassium iodide (8.3 g) in water (40 mL) was slowly added dropwise over about 30 minutes, and the mixture was warmed naturally to room temperature and stirred for 1 hour. The reaction mixture was poured into a saturated aqueous sodium bicarbonate solution (300 mL) containing ice. The resulting mixture was added with a saturated sodium thiosulfate solution (100 mL), and extracted with ethyl acetate. The extracts were combined, washed sequentially with water and saturated brine, dried over anhydrous sodium sulfate, and concentrated under reduced pressure to remove the solvent, and the residue was separated by silica gel column chromatography (PE/EtOAc=20/1) to give the product (5.4 g).

$^1$H NMR (400 MHz, CDCl$_3$) δ 7.93 (d, J=2.0 Hz, 1H), 7.50 (dd, J=8.8 Hz, 2.8 Hz, 1H), 6.94-7.05 (m, 2H), 6.84-6.89 (m, 1H), 6.51 (d, J=8.8 Hz, 1H).

Step C: 1-{[3-bromo-4-(2,4-difluorophenoxy)phenyl]imino}tetrahydro-1H-1λ⁶-thiophene-1-oxide

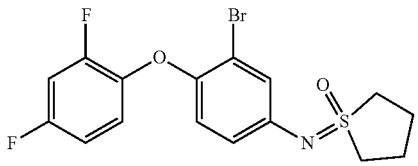 [SMILES: O=S1(=Nc2ccc(Oc3ccc(F)cc3F)c(Br)c2)CCCC1]

To anhydrous dioxane (10 mL) were sequentially added 2-bromo-1-(2,4-difluorophenoxy)-4-iodobenzene (100 mg), 1-iminotetrahydro-1H-1λ⁶-thiophene-1-oxide (35 mg), cesium carbonate (313 mg), Xantphos (11 mg), and Pd$_2$(dba)$_3$ (6 mg) under N$_2$ atmosphere, and the mixture was heated to 100° C. and stirred for 3 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (DCM/MeOH=30/1) to give the product (76 mg).

$^1$H NMR (400 MHz, CDCl$_3$) δ 7.33 (d, J=2.4 Hz, 1H), 6.91-6.96 (m, 2H), 6.86 (td, J=8.8 Hz, 5.6 Hz, 1H), 6.76-6.81 (m, 2H), 3.36-3.42 (m, 2H), 3.14-3.20 (m, 2H), 2.22-2.36 (m, 4H).

Step D: 4-{2-(2,4-difluorophenoxy)-5-[(1-oxidotetrahydro-1λ⁶-thiophen-1-ylidene)amino]phenyl}-6-methyl-1-tosyl-1,6-dihydro-7H-pyrrolo[2,3-c]pyridin-7-one

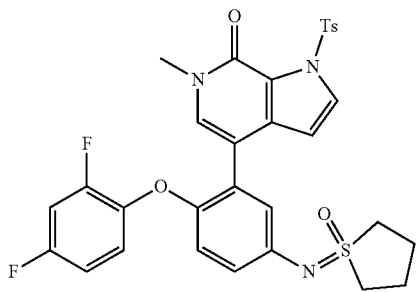 [SMILES: Cc1ccc(S(=O)(=O)n2ccc3c(-c4cc(N=S5(=O)CCCC5)ccc4Oc4ccc(F)cc4F)cn(C)c(=O)c32)cc1]

To an 80% aqueous dioxane solution (10 mL) were sequentially added 1-{[3-bromo-4-(2,4-difluorophenoxy)phenyl]imino}tetrahydro-1H-1λ⁶-thiophene-1-oxide (76 mg), 6-methyl-4-(4,4,5,5-tetramethyl-1,3,2-dioxaborolan-2-yl)-1-tosyl-1,6-dihydro-7H-pyrrolo[2,3-c]pyridin-7-one (53 mg), potassium phosphate (81 mg), and PdCl$_2$(dppf) (14 mg, 0.1 eq) under N$_2$ atmosphere, and the mixture was heated to 80° C. and stirred for 6 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (DCM/MeOH=30/1) to give the product (40 mg).

$^1$H NMR (400 MHz, CDCl$_3$) δ 8.01 (d, J=8.0 Hz, 2H), 7.86 (d, J=3.6 Hz, 1H), 7.30 (d, J=8.0 Hz, 2H), 7.15 (s, 1H), 7.07 (d, J=2.4 Hz, 1H), 6.94 (dd, J=8.8 Hz, 2.8 Hz, 1H), 6.75-6.83 (m, 3H), 6.65-6.71 (m, 1H), 6.50 (d, J=3.6 Hz, 1H), 3.51 (s, 3H), 3.38-3.44 (m, 2H), 3.13-3.20 (m, 2H), 2.40 (s, 3H), 2.24-2.37 (m, 4H).

Step E: 4-{2-(2,4-difluorophenoxy)-5-[(1-oxidotetrahydro-1λ⁶-thiophene-1-ylidene)amino]phenyl}-6-methyl-1,6-dihydro-7H-pyrrolo[2,3-c]pyridin-7-one

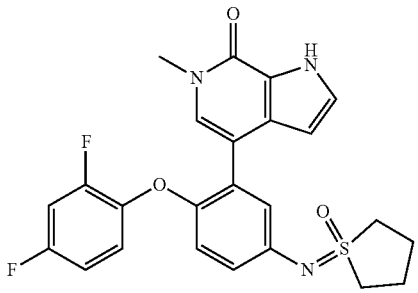 [SMILES: Cn1cc(-c2cc(N=S3(=O)CCCC3)ccc2Oc2ccc(F)cc2F)c2cc[nH]c2c1=O]

To a mixed solution of ethanol and 1 N NaOH solution (3 mL:3 mL) was added 4-{2-(2,4-difluorophenoxy)-5-[(1-oxidotetrahydro-1λ⁶-thiophen-1-ylidene)amino]phenyl}-6-methyl-1-tosyl-1,6-dihydro-7H-pyrrolo[2,3-c]pyridin-7-one (29 mg), and the mixture was heated to 70° C. and stirred for 1 hour. The reaction mixture was cooled to room temperature, concentrated under reduced pressure, added with a saturated aqueous disodium hydrogen phosphate solution, and extracted with dichloromethane. The extract was washed with water and saturated brine, dried over anhydrous sodium sulfate, and concentrated under reduced pressure. The residue was separated by a preparative thin-layer plate (DCM/MeOH=25/1) to give the product (28 mg).

¹H NMR (400 MHz, CDCl₃) δ 9.84 (s, 1H), 7.20-7.24 (m, 2H), 7.14 (s, 1H), 7.01 (dd, J=8.4 Hz, 2.4 Hz, 1H), 6.75-6.86 (m, 3H), 6.62-6.68 (m, 1H), 6.46 (d, J=3.6 Hz, 1H), 3.64 (s, 3H), 3.38-3.47 (m, 2H), 3.13-3.21 (m, 2H), 2.24-2.37 (m, 4H).

Example 16: 4-{5-{[dimethyl(oxo)-λ⁶-sulfanylidene]amino}-2-(4-fluoro-2,6-dimethylphenoxy)pyridin-3-yl}-N-ethyl-6-methyl-7-oxo-6,7-dihydro-1H-pyrrolo[2,3-c]pyridine-2-carboxamide

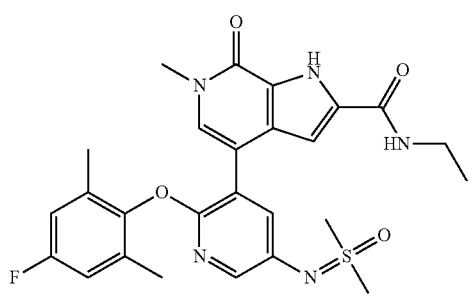

Step A: N-[5-bromo-6-(4-fluoro-2,6-dimethylphenoxy)pyridin-3-yl]-S,S-dimethylsulfonimide

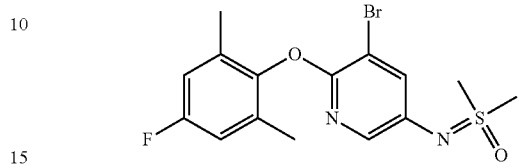

The product was obtained by referring to steps A-D in Example 1, starting from 3-bromo-2-fluoro-5-nitropyridine and 4-fluoro-2,6-dimethylphenol.

¹H NMR (400 MHz, CDCl3) δ 7.74 (s, 2H), 6.79 (d, J=8.8 Hz, 2H), 3.15 (s, 6H), 2.11 (s, 6H).

Step B: 4-{5-{[dimethyl(oxo)-λ⁶-sulfanylidene]amino}-2-(4-fluoro-2,6-dimethylphenoxy)pyridin-3-yl}-N-ethyl-6-methyl-7-oxo-6,7-dihydro-1H-pyrrolo[2,3-c]pyridine-2-carboxamide

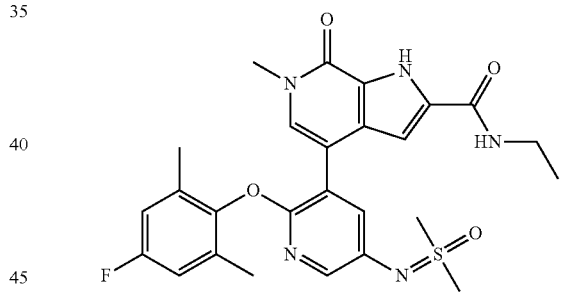

To an 80% aqueous dioxane solution (10 mL) were sequentially added N-[5-bromo-6-(4-fluoro-2,6-dimethylphenoxy) pyridin-3-yl]-S,S-dimethylsulfonimide (50 mg), N-ethyl-6-methyl-7-oxo-4-(4,4,5,5-tetramethyl-1,3,2-dioxaborolan-2-yl)-6,7-dihydro-1H-pyrrolo[2,3-c]pyridine-2-carboxamide (54 mg), potassium phosphate (55 mg), and PdCl₂(dppf) (10 mg) under N₂ atmosphere, and the mixture was heated to 80° C. and stirred for 6 hours. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (DCM/MeOH=30/1) to give the product (46 mg).

¹H NMR (400 MHz, CDCl₃) δ 10.67 (s, 1H), 7.84 (d, J=2.8 Hz, 1H), 7.66 (d, J=2.8 Hz, 1H), 7.34 (s, 1H), 6.88 (d, J=2.4 Hz, 1H), 6.78 (d, J=8.8 Hz, 2H), 6.59 (s, 1H), 3.72 (s, 3H), 3.46-3.56 (m, 2H), 3.14 (s, 6H), 2.07 (s, 6H), 1.26 (t, J=7.2 Hz, 3H).

Example 17: 4-{5-{[dimethyl(oxo)-λ⁶-sulfa-nylidene]amino}-2-[3-methyl-4-oxopyridin-1(4H)-yl]phenyl}-6-methyl-1,6-dihydro-7H-pyrrolo[2,3-c]pyridin-7-one

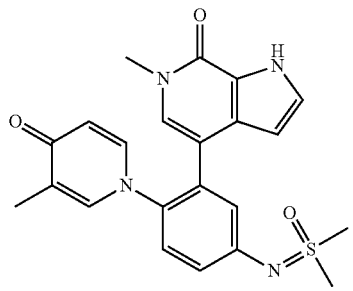 [SMILES: Cc1cn(-c2ccc(N=S(C)(C)=O)cc2-c2cn(C)c(=O)c3[nH]ccc23)ccc1=O]

Step A: 1-(2-bromo-4-nitrophenyl)-3-methylpyridin-4(1H)-one

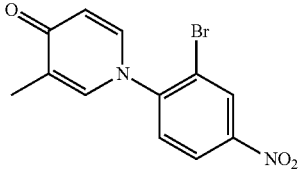

The product (3.1 g) was obtained by referring to step A in Example 1, starting from 2-bromo-1-fluoro-4-nitrobenzene and 3-methyl-4-hydroxypyridine.
¹H NMR (400 MHz CDCl₃) δ 8.64 (d, J=2.8 Hz, 1H), 8.36 (dd, J=8.8 Hz, 2.8 Hz, 1H), 7.61 (d, J=8.8 Hz, 1H), 7.30-7.34 (m, 2H), 6.47 (d, J=7.6 Hz, 1H), 2.09 (s, 3H).

Step B: 1-(2-bromo-4-aminophenyl)-3-methylpyridin-4(1H)-one

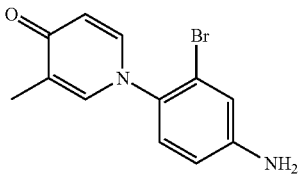 [SMILES: Cc1cn(-c2ccc(N)cc2Br)ccc1=O]

The product (0.3 g) was obtained by referring to step B in Example 1.
¹H NMR (400 MHz, CDCl₃) δ 7.25-7.27 (m, 2H), 7.11 (d, J=8.8 Hz, 1H), 6.97 (d, J=2.8 Hz, 1H), 6.66 (dd, J=8.8 Hz, 2.8 Hz, 1H), 6.44-6.46 (m, 1H), 4.01 (brs, 2H), 2.10 (s, 3H).

Step C: 1-(2-bromo-4-iodophenyl)-3-methylpyridin-4(1H)-one

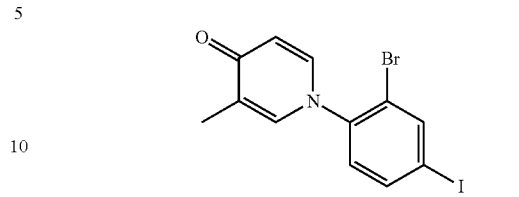

The product (80 mg) was obtained by referring to step C in Example 1.
¹H NMR (400 MHz, CDCl₃) δ 8.11 (d, J=2.0 Hz, 1H), 7.80 (dd, J=8.4 Hz, 2.0 Hz, 1H), 7.24-7.27 (m, 2H), 7.10 (d, J=8.4 Hz, 1H), 6.44 (d, J=7.6 Hz, 1H), 2.08 (s, 3H).

Step D: N-{3-bromo-4-[3-methyl-4-oxopyridin-1(4H)-yl]phenyl}-S,S-dimethylsulfonimide

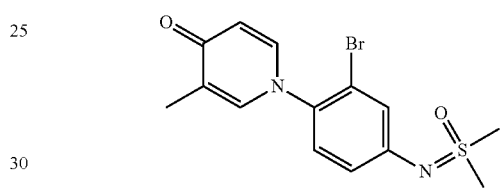

The product (55 mg) was obtained by referring to step D in Example 1.
¹H NMR (400 MHz, CDCl₃) δ 7.42 (d, J=2.4 Hz, 1H), 7.26-7.28 (m, 2H), 7.18-7.20 (m, 1H), 7.11 (dd, J=8.4 Hz, 2.4 Hz, 1H), 6.42 (d, J=2.4 Hz, 1H), 3.22 (s, 6H), 2.08 (s, 3H).

Step E: 4-{5-{[dimethyl(oxo)-λ⁶-sulfanylidene]amino}-2-[3-methyl-4-oxopyridin-1(4H)-yl]phenyl}-6-methyl-1,6-dihydro-7H-pyrrolo[2,3-c]pyridin-7-one

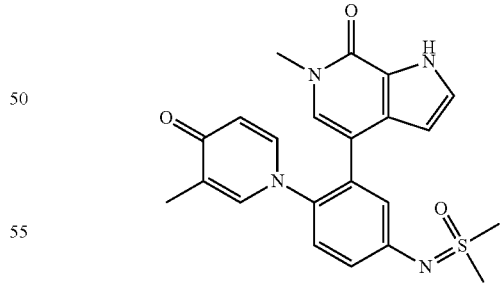

The product (10 mg) was obtained by referring to step D in Example 2, starting from N-{3-bromo-4-[3-methyl-4-oxopyridin-1(4H)-yl]phenyl}-S,S-dimethylsulfonimide and 6-methyl-4-(4,4,5,5-tetramethyl-1,3,2-dioxaborolan-2-yl)-1,6-dihydro-7H-pyrrolo[2,3-c]pyridin-7-one.
¹H NMR (400 MHz, CDCl₃) δ 11.03 (brs, 1H), 7.23-7.29 (m, 2H), 7.18-7.22 (m, 4H), 6.65 (s, 1H), 6.21 (d, J=7.6 Hz, 1H), 6.14 (d, J=2.4 Hz, 1H), 3.57 (s, 3H), 3.23 (s, 6H), 1.99 (s, 3H).

Example 18: 4-{3-(2,4-difluorophenoxy)-6-{[dimethyl(oxo)-λ⁶-sulfanylidene]amino}-pyridin-2-yl}-6-methyl-1,6-dihydro-7H-pyrrolo[2,3-c]pyridin-7-one

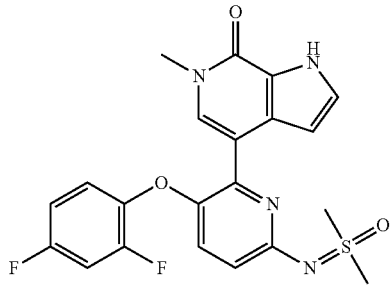 [SMILES: Cn1cc(-c2nc(N=S(C)(C)=O)ccc2Oc2ccc(F)cc2F)c2cc[nH]c2c1=O]

Step A: Ethyl 5-fluoropicolinate

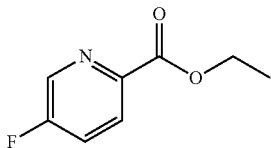

To a solution of 5-fluoropicolinic acid (5.00 g) in ethanol (42 mL) were sequentially added DMF (0.1 mL) and thionyl chloride (5.6 mL) slowly and dropwise at 0° C., and after completion of the addition, the mixture was stirred for 15 minutes, slowly heated to reflux, and reacted for 4 hours. The reaction mixture was cooled, and concentrated under reduced pressure, and the residue was poured into ice water, added with a saturated sodium bicarbonate solution to adjust pH to 8-9, and extracted 3 times with ethyl acetate. The extracts were combined, washed sequentially with water and saturated brine, dried over anhydrous sodium sulfate, and concentrated under reduced pressure to remove the solvent to give the product (5.50 g).

Step B: Ethyl 5-(2,4-difluorophenoxy)picolinate

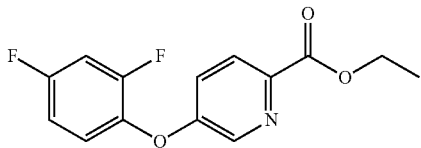 [SMILES: CCOC(=O)c1ccc(Oc2ccc(F)cc2F)cn1]

To a solution of ethyl 5-fluoropicolinate (5.40 g) in DMF (60 mL) were sequentially added 2,4-difluorophenol (4.15 g) and potassium carbonate (8.82 g) at room temperature, and the mixture was heated to 100° C. and reacted overnight. The reaction mixture was cooled, diluted with water (400 mL) and extracted with 3 times with ethyl acetate. The extracts were combined, washed sequentially with water and saturated brine, dried over anhydrous sodium sulfate, and concentrated under reduced pressure to remove the solvent to give the product (8.40 g).

¹H NMR (400 MHz, CDCl₃) δ 8.48 (d, J=2.8 Hz, 1H), 8.10 (d, J=8.8 Hz, 1H), 7.15-7.24 (m, 2H), 6.92-7.04 m, 2H), 4.46 (q, J=7.2 Hz, 2H), 1.44 (t, J=7.2 Hz, 3H).

Step C: 5-(2,4-difluorophenoxy)-2-(ethoxycarbonyl)pyridine 1-oxide

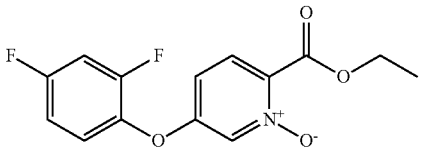 [SMILES: CCOC(=O)c1ccc(Oc2ccc(F)cc2F)c[n+]1[O-]]

To a solution of ethyl 5-(2,4-difluorophenoxy)picolinate (1.00 g) in dichloromethane (30 mL) was added 85% m-chloroperoxybenzoic acid (1.45 g) at room temperature, and the mixture reacted overnight at room temperature. After the reaction was completed, the reaction mixture was added with a saturated sodium bicarbonate solution (40 mL), stirred for 15 minutes, and extracted 3 times with dichloromethane. The extracts were combined, washed sequentially with a saturated sodium thiosulfate solution, water and saturated brine, dried over anhydrous sodium sulfate, and concentrated under reduced pressure to remove the solvent to give the product (1.00 g).

¹H NMR (400 MHz, CDCl₃) δ 7.95 (d, J=2.4 Hz, 1H), 7.63 (d, J=8.8 Hz, 1H), 7.19 (td, J=8.8 Hz, 5.6 Hz, 1H), 6.93-7.04 (m, 2H), 6.86 (dd, J=8.8 Hz, 2.4 Hz, 1H), 4.44 (q, J=7.2 Hz, 2H), 1.40 (t, J=7.2 Hz, 3H).

Step D: Ethyl 6-bromo-5-(2,4-difluorophenoxy)picolinate

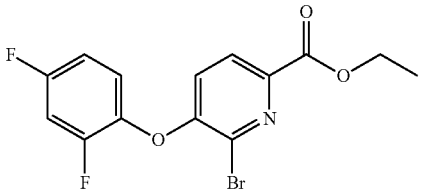 [SMILES: CCOC(=O)c1ccc(Oc2ccc(F)cc2F)c(Br)n1]

To a solution of 5-(2,4-difluorophenoxy)-2-(ethoxycarbonyl)pyridine 1-oxide (1.00 g) in DMF (15 mL) were sequentially added tetramethylammonium bromide (1.37 g) and methanesulfonic anhydride (1.24 g) at 0° C. After the addition, the mixture was slowly warmed to room temperature and reacted for 3 hours. After the reaction was completed, the reaction mixture was poured into a sodium bicarbonate solution containing ice water (40 mL), stirred for 5 minutes, and extracted 3 times with ethyl acetate. The extracts were combined, washed sequentially with water and saturated brine, dried over anhydrous sodium sulfate, and concentrated under reduced pressure. The residue was purified by silica gel column chromatography (EtOAc/PE=1/5-1/1) to give the product (0.80 g).

¹H NMR (400 MHz, CDCl₃) δ 7.99 (d, J=8.0 Hz, 1H), 7.20 (td, J=8.8 Hz, 5.6 Hz, 1H), 6.94-7.05 (m, 3H), 4.46 (q, J=7.2 Hz, 2H), 1.42 (t, J=7.2 Hz, 3H).

Step E: 6-bromo-5-(2,4-difluorophenoxy)picolinic acid

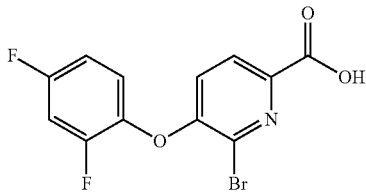 [SMILES: O=C(O)c1ccc(Oc2ccc(F)cc2F)c(Br)n1]

To a solution of ethyl 6-bromo-5-(2,4-difluorophenoxy)picolinate (0.60 g) in tetrahydrofuran (10 mL) was added a 30% potassium hydroxide solution (1.50 mL) at 0° C. After the addition, the reaction mixture was warmed to room temperature and reacted for 2 hours. After the reaction was completed, the reaction mixture was concentrated under reduced pressure, added with water, added with diluted hydrochloric acid to adjust the pH to 4-5, stirred for 5 minutes, and filtered, and the solid was collected to give the product (0.50 g).

Step F: tert-Butyl [6-bromo-5-(2,4-difluorophenoxy)pyridin-2-yl]carbamate

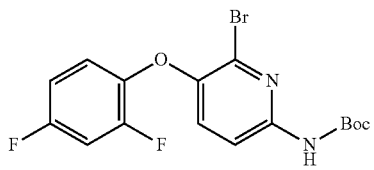 [SMILES: CC(C)(C)OC(=O)Nc1ccc(Oc2ccc(F)cc2F)c(Br)n1]

To a solution of 6-bromo-5-(2,4-difluorophenoxy)picolinic acid (0.45 g) in anhydrous tert-butanol (10 mL) were sequentially added diphenylphosphoryl azide (0.75 g), triethylamine (0.80 mL) and di-tert-butyl dicarbonate (1.19 g) at room temperature. After the addition, the reaction mixture was warmed to 90° C. and reacted for 4 hours. After the reaction was completed, the reaction mixture was concentrated under reduced pressure, poured into a saturated sodium bicarbonate solution containing ice water (20 mL), and extracted 3 times with ethyl acetate. The extracts were combined, washed sequentially with water and saturated brine, dried over anhydrous sodium sulfate, and concentrated under reduced pressure. The residue was purified by silica gel column chromatography (EtOAc/PE=1/10-1/3) to give the product (0.31 g).

$^1$H NMR (400 MHz, CDCl$_3$) δ 7.84 (d, J=8.8 Hz, 1H), 7.21 (s, 1H), 7.15 (d, J=8.8 Hz, 1H), 6.92-6.99 (m, 2H), 6.81-6.87 (m, 1H), 1.51 (s, 9H).

Step G:
6-bromo-5-(2,4-difluorophenoxy)pyridin-2-amine

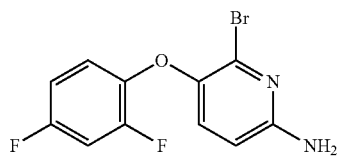

To a solution of tert-butyl [6-bromo-5-(2,4-difluorophenoxy)pyridin-2-yl]carbamate (0.31 g) in dioxane (10 mL) was added concentrated hydrochloric acid (5 mL) dropwise at 0° C., and the mixture was warmed to room temperature and reacted for 24 hours. After the reaction was completed, the reaction mixture was concentrated under reduced pressure, poured into a saturated sodium bicarbonate solution containing ice water (20 mL), and extracted 3 times with ethyl acetate. The extracts were combined, washed sequentially with water and saturated brine, dried over anhydrous sodium sulfate, and concentrated under reduced pressure to give the product (0.22 g).

$^1$H NMR (400 MHz, CDCl$_3$) δ 7.09 (d, J=8.4 Hz, 1H), 6.91-6.97 (m, 1H), 6.75-6.86 (m, 2H), 6.42 (d, J=8.4 Hz, 1H), 4.52 (brs, 2H).

Step H:
2-bromo-3-(2,4-difluorophenoxy)-6-iodopyridine

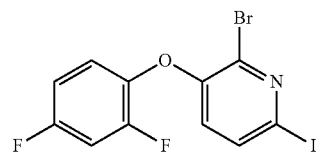 [SMILES: Fc1ccc(Oc2ccc(I)nc2Br)c(F)c1]

To a solution of 6-bromo-5-(2,4-difluorophenoxy)pyridin-2-amine (0.32 g) in diiodomethane (4 mL) at room temperature were sequentially added iodine (0.27 g) and cuprous iodide (0.20 g), the mixture was heated to 80° C., added with isoamyl nitrite (0.34 g) dropwise, and reacted for 2 hours. After the reaction was completed, the reaction mixture was cooled, poured into a sodium bicarbonate solution containing ice water (20 mL), and extracted 3 times with dichloromethane. The extracts were combined, washed sequentially with water and saturated brine, dried over anhydrous sodium sulfate, and concentrated under reduced pressure, and the residue was purified by silica gel column chromatography (DCM/PE=1/10-1/3) to give the product (0.20 g).

$^1$H NMR (400 MHz, CDCl$_3$) δ 7.55 (d, J=8.4 Hz, 1H), 7.11 (td, J=8.8 Hz, 5.6 Hz, 1H), 6.97-7.02 (m, 1H), 6.89-6.94 (m, 1H), 6.67 (dd, J=8.4 Hz, 0.8 Hz, 1H).

Step I: ((6-bromo-5-(2,4-difluorophenoxy)pyridin-2-yl)imino)dimethyl-λ$^6$-sulfonimide

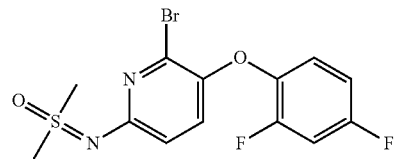 [SMILES: CS(C)(=O)=Nc1ccc(Oc2ccc(F)cc2F)c(Br)n1]

The product was obtained by referring to step D in Example 1, starting from 2-bromo-3-(2,4-difluorophenoxy)-6-iodopyridine.

¹H NMR (400 MHz, CDCl₃) δ 7.10 (d, J=8.4 Hz, 1H), 6.92-6.97 (m, 1H), 6.87 (td, J=8.8 Hz, 5.6 Hz, 1H), 6.77-6.82 (m, 1H), 6.69 (d, J=8.4 Hz, 1H), 3.37 (s, 6H).

Step J: tert-Butyl 4-bromo-6-methyl-7-oxo-6,7-dihydro-1H-pyrrolo[2,3-c]pyridine-1-carboxylate

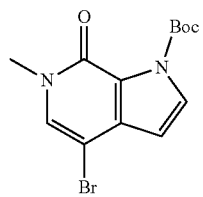 [SMILES: Cn1cc(Br)c2ccn(C(=O)OC(C)(C)C)c2c1=O]

To a solution of 4-bromo-6-methyl-1,6-dihydro-7H-pyrrolo[2,3-c]pyridin-7-one (1.73 g) in acetonitrile (20 mL) were sequentially added (Boc)₂O (2.47 g) and DMAP (1.44 g), and the mixture was stirred at room temperature overnight. The reaction solution was concentrated, and the residue was purified by silica gel column chromatography (ethyl acetate/petroleum ether=1/20) to give the product (2.10 g).

¹H NMR (400 MHz, CDCl₃) δ 7.55 (d, J=3.6 Hz, 1H), 7.21 (s, 1H), 6.35 (d, J=3.6 Hz, 1H), 3.55 (s, 3H), 1.62 (s, 9H).

Step K: tert-Butyl 6-methyl-7-oxo-4-(4,4,5,5-tetramethyl-1,3,2-dioxaborolan-2-yl)-6,7-dihydro-1H-pyrrolo[2,3-c]pyridine-1-carboxylate

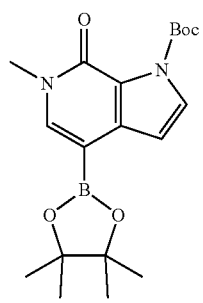 [SMILES: Cn1cc(B2OC(C)(C)C(C)(C)O2)c2ccn(C(=O)OC(C)(C)C)c2c1=O]

The product was obtained by referring to step I in Example 1, starting from tert-butyl 4-bromo-6-methyl-7-oxo-6,7-dihydro-1H-pyrrolo[2,3-c]pyridine-1-carboxylate.

¹H NMR (400 MHz, CDCl₃) δ 7.60 (s, 1H), 7.55 (d, J=3.6 Hz, 1H), 6.79 (d, J=3.6 Hz, 1H), 3.62 (s, 3H), 1.65 (s, 9H), 1.34-1.65 (s, 12H).

Step L: tert-Butyl 4-{3-(2,4-difluorophenoxy)-6-{[dimethyl(oxo)-λ⁶-sulfanylidene]amino}-pyridin-2-yl}-6-methyl-7-oxo-6,7-dihydro-1H-pyrrolo[2,3-c]pyridine-1-carboxylate

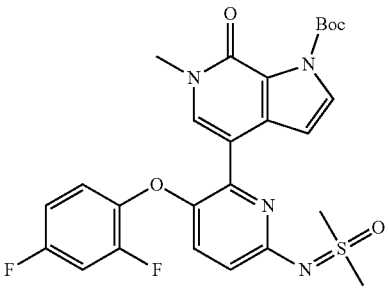 [SMILES: Cn1cc(-c2nc(N=S(C)(C)=O)ccc2Oc2ccc(F)cc2F)c2ccn(C(=O)OC(C)(C)C)c2c1=O]

To an 80% aqueous dioxane solution (3 mL) were sequentially added ((6-bromo-5-(2,4-difluorophenoxy)pyridine-2-yl)imino)dimethyl-λ⁶-sulfonimide (59 mg), tert-butyl 6-methyl-7-oxo-4-(4,4,5,5-tetramethyl-1,3,2-dioxaborolan-2-yl)-6,7-dihydro-1H-pyrrolo[2,3-c]pyridine-1-carboxylate (65 mg), cesium fluoride (83 mg), and PdCl₂(AtaPhos) (9 mg) under nitrogen atmosphere, and the mixture was heated to 85° C. and stirred overnight. The reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (MeOH/DCM=1/20) to give the product (58 mg).

¹H NMR (400 MHz, CDCl₃) δ 7.82 (s, 1H), 7.58-7.59 (m, 1H), 7.23 (d, J=8.4 Hz, 1H), 7.15-7.17 (m, 1H), 6.85-6.92 (m, 1H), 6.65-6.75 (m, 3H), 3.63 (s, 3H), 3.33 (s, 6H), 1.65 (s, 9H).

Step M: 4-{3-(2,4-difluorophenoxy)-6-{[dimethyl(oxo)-λ⁶-sulfanylidene]amino}-pyridin-2-yl}-6-methyl-1,6-dihydro-7H-pyrrolo[2,3-c]pyridin-7-one

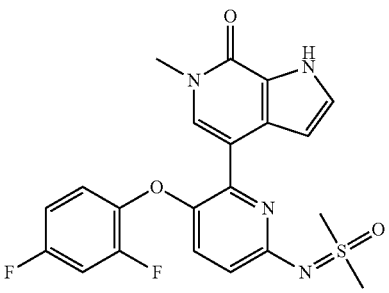

To tert-butyl 4-{3-(2,4-difluorophenoxy)-6-{[dimethyl(oxo)-λ⁶-sulfanylidene]amino}-pyridin-2-yl}-6-methyl-7-oxo-6,7-dihydro-1H-pyrrolo[2,3-c]pyridine-1-carboxylate (50 mg) was added a 4 moL/L hydrogen chloride dioxane solution (1 mL) at room temperature, and the reaction was warmed to room temperature and reacted for 2 hours. After the reaction was completed, the reaction mixture was concentrated under reduced pressure, poured into a sodium bicarbonate solution containing ice water (5 mL), and extracted 3 times with ethyl acetate. The extracts were combined, washed sequentially with water and saturated brine, dried over anhydrous sodium sulfate, and concentrated under reduced pressure to give the product (35 mg).

¹H NMR (400 MHz, CDCl₃) δ 12.01 (brs, 1H), 9.56 (brs, 1H), 7.72 (s, 1H), 7.24 (d, J=8.8 Hz, 1H), 7.14 (t, J=2.4 Hz, 1H), 6.85-6.91 (m, 1H), 6.64-6.76 (m, 3H), 3.66 (s, 3H), 3.35 (s, 6H).

Example 19: 4-{5-(2,4-difluorophenoxy)-2-{[dimethyl(oxo)-λ⁶-sulfanylidene]amino}-pyridin-4-yl}-6-methyl-1,6-dihydro-7H-pyrrolo[2,3-c]pyridin-7-one

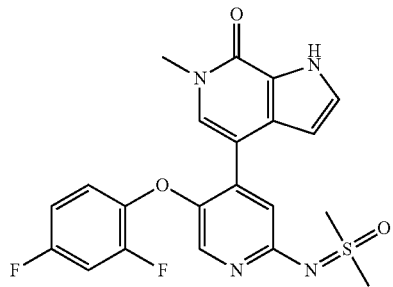 [SMILES: Cn1cc(-c2cc(N=S(C)(C)=O)ncc2Oc2ccc(F)cc2F)c2cc[nH]c2c1=O]

Step A: 4-bromo-5-fluoropicolinic acid

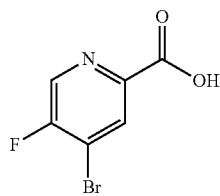 [SMILES: O=C(O)c1cc(Br)c(F)cn1]

To a solution of 5-fluoropicolinic acid (0.50 g) in anhydrous tetrahydrofuran (10 mL) was slowly added dropwise a 2 mol/L solution of LDA in tetrahydrofuran (3.5 mL) under nitrogen atmosphere at −78° C., and the mixture was reacted for 15 minutes, and slowly warmed to −20° C. and reacted for another 30 minutes. The reaction mixture was cooled to −78° C., added with a solution of dichlorotetrabromoethane (1.15 g) in anhydrous tetrahydrofuran (3 mL) dropwise, reacted for 30 minutes, and slowly warmed to −10° C. and reacted for another 2 hours. The reaction was quenched with saturated aqueous citric acid (15 mL), and the resulting mixture was added with sodium chloride solid until saturated, and extracted 3 times with ethyl acetate. The extracts were combined, dried over anhydrous sodium sulfate, and concentrated under reduced pressure to remove the solvent to give a crude product (0.50 g), which was used directly in the next step.

Step B: Methyl 4-bromo-5-fluoropicolinate

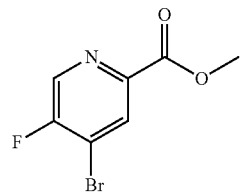

To a solution of 4-bromo-5-fluoropicolinic acid (0.50 g) in methanol (60 mL) was added concentrated sulfuric acid (0.1 mL) at room temperature, and the mixture was heated to 70° C. to reacted for 1 hour. The reaction mixture was cooled, and concentrated, and the residue was poured into a saturated aqueous sodium bicarbonate solution, and extracted 3 times with ethyl acetate. The extracts were combined, washed sequentially with water and saturated brine, dried over anhydrous sodium sulfate, and concentrated under reduced pressure. The residue was purified by silica gel column chromatography (EtOAc/PE=1/20-1/10) to give the product (0.32 g).

¹H NMR (400 MHz, CDCl₃) δ 8.54 (s, 1H), 8.40 (d, J=5.2 Hz, 1H), 4.00 (s, 3H).

Step C: Methyl 4-bromo-5-(2,4-difluorophenoxy)picolinate

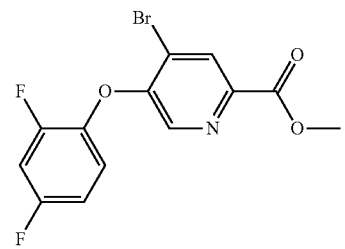 [SMILES: COC(=O)c1cc(Br)c(Oc2ccc(F)cc2F)cn1]

To a solution of methyl 4-bromo-5-fluoropicolinate (0.32 g) in DMF (4 mL) were sequentially added 2,4-difluorophenol (0.20 g) and potassium carbonate (0.38 g) at room temperature, and the mixture was heated to 80° C. and reacted for 2 hours. The reaction mixture was cooled, diluted with water (40 mL) and filtered, and the solid was collected to give the product (0.45 g).

¹H NMR (400 MHz, CDCl₃) δ 8.42 (s, 1H), 8.07 (s, 1H), 7.16 (td, J=8.8 Hz, 5.2 Hz, 1H), 6.99-7.04 (m, 1H), 6.92-9.97 (m, 1H), 3.99 (s, 3H).

Step D; 4-bromo-5-(2,4-difluorophenoxy)picolinic acid

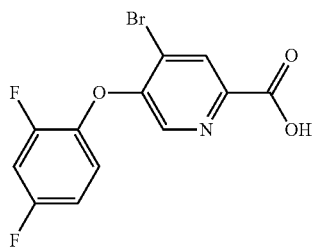 [SMILES: O=C(O)c1cc(Br)c(Oc2ccc(F)cc2F)cn1]

To a solution of methyl 4-bromo-5-(2,4-difluorophenoxy) picolinate (0.45 g) in tetrahydrofuran (5 mL) was added a 2.5 mol/L sodium hydroxide solution (5 mL) at 0° C. After the addition, the reaction mixture was warmed to room temperature and reacted for 2 hours. After the reaction was completed, the reaction mixture was concentrated under reduced pressure, added with water, added with diluted hydrochloric acid to adjust the pH to 4-5, stirred for 5 minutes, and filtered, and the solid was collected to give the product (0.42 g).

$^1$H NMR (400 MHz, CDCl$_3$) δ 8.49 (s, 1H), 7.94 (s, 1H), 7.21 (td, J=8.8 Hz, 5.6 Hz, 1H), 7.01-7.07 (m, 1H), 6.95-7.01 (m, 1H).

Step E: tert-Butyl [4-bromo-5-(2,4-difluorophenoxy)pyridin-2-yl]carbamate

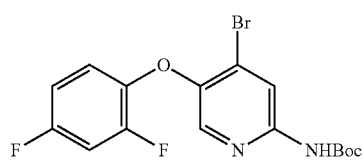 [SMILES: CC(C)(C)OC(=O)Nc1cc(Br)c(Oc2ccc(F)cc2F)cn1]

The product was obtained by referring to step F in Example 18, starting from 4-bromo-5-(2,4-difluorophenoxy) picolinic acid.

$^1$H NMR (400 MHz, CDCl$_3$) δ 8.33 (s, 1H), 7.82 (s, 1H), 7.35 (s, 1H), 6.93-6.99 (m, 1H), 6.89-6.91 (m, 1H), 6.78-6.84 (m, 1H), 1.52 (s, 9H).

Step F: 4-bromo-5-(2,4-difluorophenoxy)pyridin-2-amine

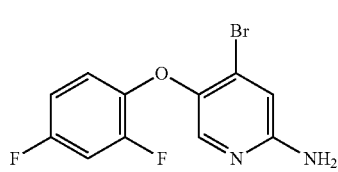 [SMILES: Nc1cc(Br)c(Oc2ccc(F)cc2F)cn1]

The product was obtained by referring to step G in Example 18, starting from tert-butyl [4-bromo-5-(2,4-difluorophenoxy)pyridin-2-yl]carbamate.

Step G: 4-bromo-5-(2,4-difluorophenoxy)-2-iodopyridine

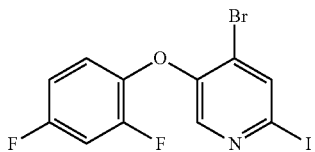 [SMILES: Fc1ccc(Oc2cnc(I)cc2Br)c(F)c1]

The product was obtained by referring to step H in Example 18, starting from 4-bromo-5-(2,4-difluorophenoxy)pyridin-2-amine.

$^1$H NMR (400 MHz, CDCl$_3$) δ 7.97 (s, 1H), 7.82 (s, 1H), 7.07 (td, J=8.8 Hz, 5.6 Hz, 1H), 6.96-7.02 (m, 2H), 6.87-6.93 (m, 1H).

Step H: ((4-bromo-5-(2,4-difluorophenoxy)pyridin-2-yl)imino)dimethyl-λ$^6$-sulfonimide

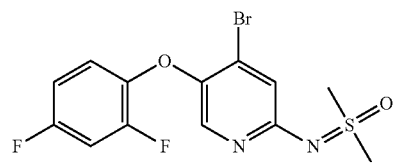 [SMILES: CS(C)(=O)=Nc1cc(Br)c(Oc2ccc(F)cc2F)cn1]

The product was obtained by referring to step D in Example 1, starting from 4-bromo-5-(2,4-difluorophenoxy)-2-iodopyridine.

$^1$H NMR (400 MHz, CDCl$_3$) δ 7.83 (s, 1H), 7.08 (s, 1H), 6.92-6.97 (m, 1H), 6.87 (td, J=8.8 Hz, 5.2 Hz, 1H), 6.76-6.81 (m, 1H), 3.34 (s, 6H).

Step I: tert-Butyl 4-{5-(2,4-difluorophenoxy)-2-{[dimethyl(oxo)-λ$^6$-sulfanylidene]amino}-pyridin-4-yl}-6-methyl-7-oxo-6,7-dihydro-1H-pyrrolo[2,3-c]pyridine-1-carboxylate

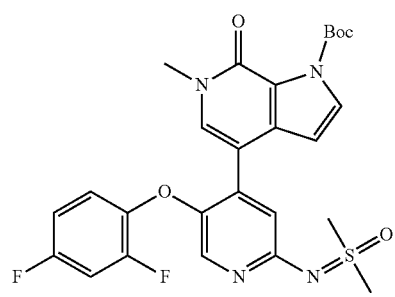 [SMILES: Cn1cc(-c2cc(N=S(C)(C)=O)ncc2Oc2ccc(F)cc2F)c2ccn(C(=O)OC(C)(C)C)c2c1=O]

The product was obtained by referring to step L in Example 18, starting from ((4-bromo-5-(2,4-difluorophenoxy)pyridin-2-yl)imino)dimethyl-λ$^6$-sulfonimide $^1$H NMR (400 MHz, CDCl$_3$) δ 7.93 (s, 1H), 7.55 (d, J=3.6 Hz, 1H), 7.34 (s, 1H), 6.87 (s, 1H), 6.81-6.86 (m, 1H), 6.76 (td, J=8.8 Hz, 5.6 Hz, 1H), 6.63-6.69 (m, 1H), 6.44 (d, J=3.6 Hz, 1H), 3.61 (s, 3H), 3.39 (s, 6H), 1.65 (s, 9H).

Step J: 4-{5-(2,4-difluorophenoxy)-2-{[dimethyl(oxo)-λ⁶-sulfanylidene]amino}-pyridin-4-yl}-6-methyl-1,6-dihydro-7H-pyrrolo[2,3-c]pyridin-7-one

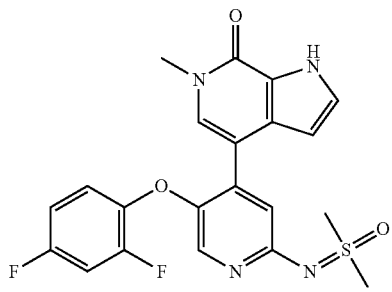

The product was obtained by referring to step M in Example 18, starting from tert-butyl 4-{5-(2,4-difluorophenoxy)-2-{[dimethyl(oxo)-λ⁶-sulfanylidene]amino}-pyridin-4-yl}-6-methyl-7-oxo-6,7-dihydro-1H-pyrrolo[2,3-c]pyridine-1-carboxylate.

¹H NMR (400 MHz, CDCl₃) δ 9.87 (s, 1H), 7.95 (s, 1H), 7.27 (s, 1H), 7.01 (s, 1H), 6.79-6.85 (m, 2H), 6.77 (td, J=8.8 Hz, 5.6 Hz, 1H), 6.61-6.68 (m, 1H), 6.50 (t, J=2.8 Hz, 1H), 3.63 (s, 3H), 3.39 (s, 6H).

Example 20: 4-{2-(2-chloro-6-methylphenoxy)-5-{[dimethyl(oxo)-λ⁶-sulfanylidene]amino}-pyridin-3-yl}-6-methyl-1,6-dihydro-7H-pyrrolo[2,3-c]pyridin-7-one

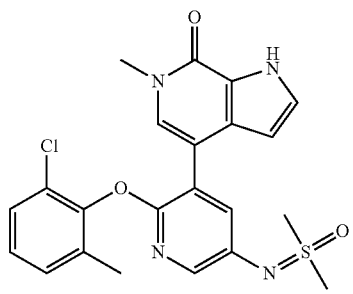 [SMILES: Cc1cccc(Cl)c1Oc1ncc(N=S(C)(C)=O)cc1-c1cn(C)c(=O)c2[nH]ccc12]

Step A: 3-bromo-2-(2-chloro-6-methylphenoxy)-5-nitropyridine

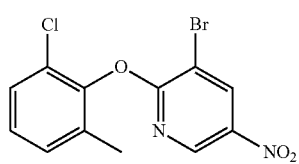 [SMILES: Cc1cccc(Cl)c1Oc1ncc([N+](=O)[O-])cc1Br]

To a solution of 2-chloro-6-methylphenol (1.0 g) in anhydrous DMF (10 mL) was added 2-chloro-3-bromo-5-nitropyridine (1.66 g) and cesium carbonate (4.56 g) at room temperature, and the reaction mixture was heated to 120° C. and stirred overnight. After the reaction was completed, the reaction was quenched with water and the resulting mixture was extracted with ethyl acetate. The organic phase was dried over anhydrous sodium sulfate, evaporated to dryness to remove the solvent, and purified by silica gel column chromatography (EtOAc/PE=2/1) to give the product (2.40 g, 98%).

¹H NMR (400 MHz, CDCl₃) δ 8.88 (d, J=2.4 Hz, 1H), 8.77 (d, J=2.4 Hz, 1H), 7.34-7.35 (m, 1H), 7.16-7.23 (m, 2H), 2.20 (s, 3H).

Step B: ((5-bromo-6-(2-chloro-6-methylphenoxy)pyridin-3-yl)imino)dimethyl-λ⁶-sulfonimide

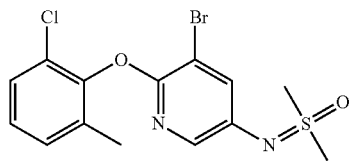 [SMILES: Cc1cccc(Cl)c1Oc1ncc(N=S(C)(C)=O)cc1Br]

The product was obtained by referring to steps B-D in Example 1, starting from 3-bromo-2-(2-chloro-6-methylphenoxy)-5-nitropyridine.

¹H NMR (400 MHz, CDCl₃) δ 7.73-7.75 (m, 2H), 7.26-7.30 (m, 1H), 7.17-7.23 (m, 1H), 7.11-7.16 (m, 1H), 3.12-3.15 (m, 6H), 2.19 (s, 3H).

Step C: 4-{2-(2-chloro-6-methylphenoxy)-5-{[dimethyl(oxo)-λ⁶-sulfanylidene]amino}-pyridin-3-yl}-6-methyl-1,6-dihydro-7H-pyrrolo[2,3-c]pyridin-7-one

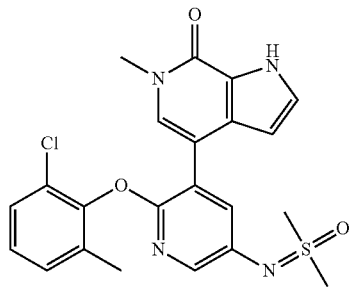 [SMILES: Cc1cccc(Cl)c1Oc1ncc(N=S(C)(C)=O)cc1-c1cn(C)c(=O)c2[nH]ccc12]

The product was obtained by referring to step D in Example 2, starting from ((5-bromo-6-(2-chloro-6-methylphenoxy)pyridin-3-yl)imino)dimethyl-λ⁶-sulfonimide and 6-methyl-4-(4,4,5,5-tetramethyl-1,3,2-dioxaborolan-2-yl)-1,6-dihydro-7H-pyrrolo[2,3-c]pyridin-7-one.

¹H NMR (400 MHz, CDCl₃) δ 10.37 (brs, 1H), 7.81 (d, J=2.8 Hz, 1H), 7.68 (d, J=2.8 Hz, 1H), 7.44 (s, 1H), 7.26-7.29 (m, 2H), 7.13-7.15 (m, 1H), 7.04-7.08 (m, 1H), 6.58 (dd, J=2.8 Hz, 2.4 Hz, 1H), 3.72 (s, 3H), 3.15-3.18 (m, 6H), 2.13 (s, 3H).

Example 21: 4-{2-(2-chloro-6-methylphenoxy)-5-{[dimethyl(oxo)-λ⁶-sulfanylidene]amino}-pyridin-3-yl}-N-ethyl-6-methyl-7-oxo-6,7-dihydro-1H-pyrrolo[2,3-c]pyridine-2-carboxamide

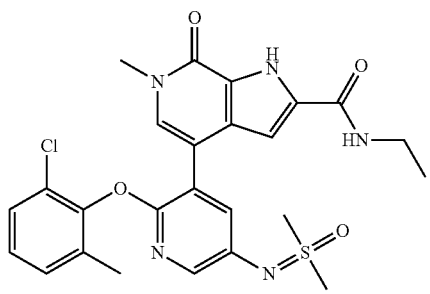 [SMILES: CCNC(=O)c1cc2c(-c3cc(N=S(C)(C)=O)cnc3Oc3c(C)cccc3Cl)cn(C)c(=O)c2[nH]1]

The product was obtained by referring to step J in Example 1, starting from ((5-bromo-6-(2-chloro-6-methylphenoxy)pyridin-3-yl)imino)dimethyl-λ⁶-sulfonimide and N-ethyl-6-methyl-7-oxo-4-(4,4,5,5-tetramethyl-1,3,2-dioxaborolan-2-yl)-6,7-dihydro-1H-pyrrolo[2,3-c]pyridine-2-carboxamide.

¹H NMR (400 MHz, CDCl₃) δ 11.25 (brs, 1H), 7.84 (d, J=2.8 Hz, 1H), 7.66 (d, J=2.8 Hz, 1H), 7.47 (s, 1H), 7.26-7.31 (m, 1H), 7.06-7.16 (m, 4H), 3.74 (s, 3H), 3.52 (q, J=7.2 Hz, 2H), 3.18 (s, 6H), 2.11 (s, 3H), 1.26 (t, J=7.2 Hz, 3H).

Example 22: 4-{5-{[dimethyl(oxo)-λ⁶-sulfanylidene]amino}-2-(4-fluoro-2,6-dimethylphenoxy)phenyl}-6-methyl-7-oxo-N-(2,2,2-trifluoroethyl)-6,7-dihydro-1H-pyrrolo[2,3-c]pyridine-2-carboxamide

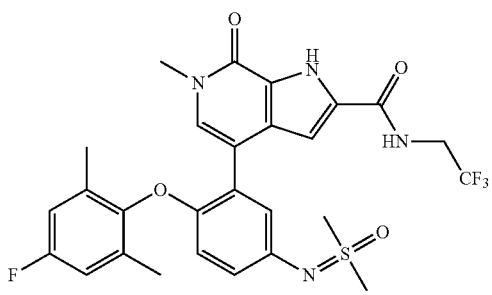 [SMILES: Cc1cc(F)cc(C)c1Oc1ccc(N=S(C)(C)=O)cc1-c1cn(C)c(=O)c2[nH]c(C(=O)NCC(F)(F)F)cc12]

Step A: 4-bromo-6-methyl-7-oxo-6,7-dihydro-1H-pyrrolo[2,3-c]pyridine-2-carboxylic acid

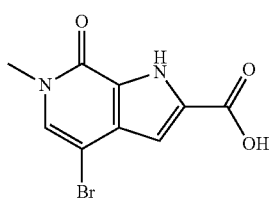

Butyl 4-bromo-6-methyl-7-oxo-1-tosyl-6,7-dihydro-1H-pyrrolo[2,3-c]pyridine-2-carboxylate (300 mg) was reacted in a mixed solvent of ethanol (10 mL) and water (10 mL) at 80° C. for 1 hour. After cooling to room temperature, the reaction mixture was concentrated under reduced pressure, added with 1 N hydrochloric acid to adjust the pH to 5. A solid was precipitated, obtained by suction filtration, washed with water for multiple times, and dried to give the product (160 mg) in the form of a white solid.

Step B: 4-bromo-6-methyl-7-oxo-N-(2,2,2-trifluoroethyl)-6,7-dihydro-1H-pyrrolo[2,3-c]pyridine-2-carboxamide

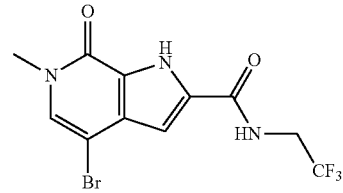 [SMILES: Cn1cc(Br)c2cc(C(=O)NCC(F)(F)F)[nH]c2c1=O]

4-bromo-6-methyl-7-oxo-6,7-dihydro-1H-pyrrolo[2,3-c]pyridine-2-carboxylic acid (150 mg) was dissolved in dichloromethane (10 mL) under nitrogen atmosphere, and the solution was added with 2 drops of DMF, and added with oxalyl chloride (60 mg) dropwise at 0° C. The mixture was reacted at room temperature for 1 hour, added with trifluoroethylamine (220 mg) and triethylamine (111 mg), and reacted at room temperature for another 1 hour. After the reaction was completed, water was added to quench the reaction, the resulting mixture was extracted with ethyl acetate, and the organic phase was concentrated under reduced pressure. The residue was separated by column chromatography (DCM/MeOH=20/1) to give the product (190 mg).

¹H NMR (400 MHz, d6-DMSO) δ 12.79 (s, 1H), 9.06 (t, J=6.0 Hz, 1H), 7.60 (s, 1H), 7.01 (s, 1H), 4.06-4.12 (m, 2H), 3.49 (s, 3H).

Step C: ((4-(4-fluoro-2,6-dimethylphenoxy)-3-(4,4,5,5-tetramethyl-1,3,2-dioxaborolan-2-yl)phenyl)imino)dimethyl-λ⁶-sulfonimide

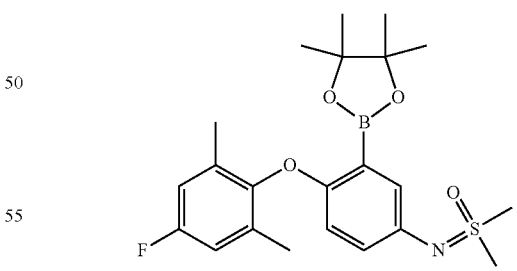

To dioxane (20 mL) were added N-[3-bromo-4-(4-fluoro-2,6-dimethylphenoxy)phenyl]-S,S-dimethylsulfonimide (100 mg), bis(pinacolato)diboron (76 mg), anhydrous potassium carbonate (72 mg), and PdCl₂(dppf) (19 mg) under nitrogen atmosphere, and the mixture was heated to 100° C. and reacted for 12 hours. After the reaction was completed, the reaction mixture was cooled to room temperature, added with water, and extracted with ethyl acetate. The extract was washed with water and saturated brine, dried over anhydrous sodium sulfate, and concentrated under reduced pressure. The residue was separated by a preparative thin-layer plate (DCM/EA=3/1) to give the product (30 mg).

¹H NMR (400 MHz, CDCl₃) δ 7.39 (s, 1H), 6.95 (d, J=8.8 Hz, 1H), 6.76 (d, J=9.2 Hz, 2H), 6.17 (d, J=8.8 Hz, 1H), 3.13 (s, 6H), 2.12 (s, 6H), 1.34 (s, 12H).

Step D: 4-{5-{[dimethyl(oxo)-λ⁶-sulfanylidene]amino}-2-(4-fluoro-2,6-dimethylphenoxy)phenyl}-6-methyl-7-oxo-N-(2,2,2-trifluoroethyl)-6,7-dihydro-1H-pyrrolo[2,3-c]pyridine-2-carboxamide

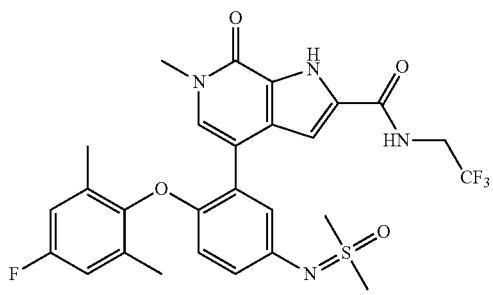 [SMILES: Cc1cc(F)cc(C)c1Oc1ccc(N=S(C)(C)=O)cc1-c1cn(C)c(=O)c2[nH]c(C(=O)NCC(F)(F)F)cc12]

((4-(4-fluoro-2,6-dimethylphenoxy)-3-(4,4,5,5-tetramethyl-1,3,2-dioxaborolan-2-yl)phenyl)imino)dimethyl-λ⁶-sulfonimide (30 mg), 4-bromo-6-methyl-7-oxo-N-(2,2,2-trifluoroethyl)-6,7-dihydro-1H-pyrrolo[2,3-c]pyridine-2-carboxamide (24 mg), anhydrous potassium phosphate (30 mg) and PdCl₂(dppf) (5 mg) were reacted in dioxane and water (10 mL/2 mL) at 80° C. for 4 hours under nitrogen atmosphere. The reaction mixture was cooled, concentrated under reduced pressure, added with water, and extracted with dichloromethane. The organic phase was washed with water and saturated brine, dried over anhydrous sodium sulfate, and concentrated under reduced pressure, and the residue was separated by a preparative thin-layer plate (DCM/MeOH=20/1) to give the product (12 mg).

¹H NMR (400 MHz, CDCl₃) δ 11.19 (s, 1H), 7.43 (s, 1H), 7.28 (s, 1H), 7.11 (s, 1H), 6.84 (dd, J=8.8 Hz, 2.4 Hz, 1H), 6.77 (d, J=8.8 Hz, 2H), 6.35 (d, J=8.8 Hz, 1H), 5.35-5.60 (brs, 1H), 4.08-4.17 (m, 2H), 3.72 (s, 3H), 3.16 (s, 6H), 2.07 (s, 6H).

Bioactivity Assay

1. In Vitro BRD4 (BD2) Enzymatic Activity Assay on Compounds

In the present application, IC$_{50}$ values of the compounds in inhibiting BRD4 (BD2) enzyme binding reaction were determined by homogeneous time resolved fluorescence (HTRF). A compound was serially diluted 5-fold with 100% DMSO starting from 1 mM (7 concentrations in total), and then 2 μL of the compound at each concentration was added to 18 μL of a reaction buffer (20 mM HEPES pH 7.5, 150 mM NaCl, 5 mM DTT, 0.005% Tween 20, and 100 μg/mL BSA) for dilution. After being mixed well, 2 μL of the compound at each concentration was added to 48 μL of the above reaction buffer for dilution, and mixed well (final concentration of the compound in DMSO: 0.1%). 2.5 μL of the resulting mixture was added to a 384-well plate (OptiPlate-384, purchased from PerkinElmer), then 5 μL of GST-BRD4 (BD2, 349-460 aa) (final concentration: 2 nM) was added, and the resulting mixture was centrifuged, and fully mixed. 2.5 μL of a peptide Biotin-AHA-SGRGK(Ac)GGK(Ac)GLGK(Ac)GGAK(Ac) RHRKV (final concentration: 200 nM) was then added to initiate the reaction (total reaction volume: 10 μL). The 384-well plate was placed in an incubator at 23° C. to react for 1 hour, and then 5 μL of Eu3+ cryptate-labled anti-GST antibody (purchased from Cisbio) and 5 μL of Streptavidin-XL-665 (purchased from Cisbio) were added to terminate the reaction. After being incubated in the incubator for another 1 hour, the fluorescence values (excited at 320 nm, emitted light at 665 nm and 620 nm being detected, and the ratio of the two being the enzyme binding signal) were read on Envision (purchased from PerkinElmer). The binding strength of each compound to BRD4 (BD2) protein was determined respectively at 7 concentrations, and the data were calculated using GraphPad Prism software to obtain the IC$_{50}$ value of the compound.

2. In Vitro BRD4 (BD1) Enzymatic Activity Assay on Compounds

In the present application, IC$_{50}$ values of the compounds in inhibiting BRD4 (BD1) enzyme binding reaction were determined by homogeneous time resolved fluorescence (HTRF). A compounds was serially diluted 5-fold with 100% DMSO starting from 0.2 mM (7 concentrations in total), and then 2 μL of the compound at each concentration was added to 48 μL of a reaction buffer (20 mM HEPES pH 7.5, 150 mM NaCl, 5 mM DTT, 0.005% Tween 20, and 100 μg/mL BSA) for dilution, and mixed well. 2.5 μL of the resulting mixture was added to a 384-well plate (OptiPlate-384, purchased from PerkinElmer), then 5 μL of GST-BRD4 (BD1, 44-168 aa) (final concentration: 1 nM) was added, and the resulting mixture was centrifuged, and fully mixed. 2.5 μL of a short peptide Biotin-AHA-SGRGK(Ac)GGK (Ac)GLGK(Ac)GGAK(Ac) RHRKV (final concentration: 100 nM) was then added to initiate the reaction (total reaction volume: 10 μL). The 384-well plate was placed in an incubator at 23° C. to react for 1 hour, and then 5 μL of Eu3+ cryptate-labled anti-GST antibody (purchased from Cisbio) and 5 μL of Streptavidin-XL-665 (purchased from Cisbio) were added to terminate the reaction. After being incubated in the incubator for another 1 hour, the fluorescence values (excited at 320 nm, emitted light at 665 nm and 620 nm being detected, and the ratio of the two being the enzyme binding signal) were read on Envision (purchased from PerkinElmer). The binding strength of each compound to BRD4 (BD1) protein was determined respectively at 7 concentrations, and the data were calculated using GraphPad Prism software to obtain the IC$_{50}$ value of the compound.

The assay results of the part of the above compounds are shown in Table 1.

TABLE 1

Results of in vitro enzymatic activity assay on compounds

| Example compound No. | BRD4-BD1 IC$_{50}$ (nM) | BRD4-BD2 IC$_{50}$ (nM) |
|---|---|---|
| 1 | 14.7 | 0.51 |
| 2 | 1.4 | 0.98 |
| 3 | 7.7 | 0.45 |
| 4 | 0.93 | 0.35 |
| 5 | 4.8 | 0.66 |
| 6 | 26.4 | 0.93 |
| 7 | 24.3 | 0.34 |
| 8 | 2.4 | 1.3 |
| 9 | 3.0 | 0.75 |
| 10 | 96.3 | 0.53 |
| 11 | 29.4 | 1.3 |
| 12 | 4.1 | 1.1 |
| 14 | 27.9 | 4.0 |
| 15 | 4.5 | 1.2 |
| 16 | 86.4 | 0.40 |
| 17 | 330 | 4.0 |

TABLE 1-continued

Results of in vitro enzymatic activity assay on compounds

| Example compound No. | BRD4-BD1 IC$_{50}$ (nM) | BRD4-BD2 IC$_{50}$ (nM) |
|---|---|---|
| 18 | 0.64 | 0.25 |
| 19 | 7.30 | 0.61 |
| 20 | 12.9 | 0.27 |
| 21 | 10.7 | 0.13 |
| 22 | 188 | 0.88 |

3. Cell Proliferation Activity Assay on Compounds in MV4-11

Human acute lymphoblastic leukemia cell line MV4-11 cells were cultured in PRIM1640 medium plus 10% fetal bovine serum (FBS, purchased from Biological Industries, BI) and 1% penicillin/streptomycin double antibody (P/S, purchased from Life Technology) at 37° C. with 5% $CO_2$. On the day before the compound test, MV4-11 cells were spread in a 96-well plate (purchased from Corning) at a concentration of 8000 cells/195 μL/well. After 24 hours, the compound was serially diluted 4-fold with 100% DMSO starting from 10 mM (9 concentrations in total), and then 2 μL of the compound at each concentration was added to 48 μL of PRIM1640 medium for dilution. 5 μL of the diluted compound at each concentration was added to the wells spread with the cell suspension, and the compound and cells were co-incubated in a cell incubator for 72 hours (3 days). Then the mixture was added with 35 μL of Cell-Titer Blue reagent (purchased from Promega) and incubated for another 4 hours. The fluorescence values (excited at 560 nm, detected at 590 nm) were then read on Flexstation III, and the data were calculated using GraphPad Prism software to give IC$_{50}$ value of the compound in inhibiting cell proliferation.

4. Cell Proliferation Activity Assay on Compounds in Kasumi-1

Human acute myeloblastic leukemia cell line Kasumi-1 cells were cultured in PRIM1640 medium plus 20% fetal bovine serum (FBS, purchased from Biological Industries, BI) and 1% penicillin/streptomycin double antibody (P/S, purchased from Life Technology) at 37° C. with 5% $CO_2$. On the day before the compound test, Kasumi-1 cells were spread in a 96-well plate (purchased from Corning) at a concentration of 5000 cells/195 μL/well. After 24 hours, the compound was serially diluted 4-fold with 100% DMSO starting from 10 mM (9 concentrations in total), and then 2 μL of the compound at each concentration was added to 48 μL of PRIM1640 medium for dilution. 5 μL of the diluted compound at each concentration was added to the wells spread with the cell suspension, and the compound and cells were co-incubated in a cell incubator for 72 hours (3 days). Then the mixture was added with 35 μL of Cell-Titer Blue reagent (purchased from Promega) and incubated for another 4 hours. The fluorescence values (excited at 560 nm, detected at 590 nm) were then read on Flexstation III, and the data were calculated using GraphPad Prism software to give IC$_{50}$ value of the compound in inhibiting cell proliferation.

The assay results of the part of the above compounds are shown in Table 2.

TABLE 2

Results of in vitro cytological activity assay on compounds

| Example compound No. | MV4-11 IC$_{50}$ (nM) | Kasumi-1 IC$_{50}$ (nM) |
|---|---|---|
| 1 | 124 | 322 |
| 2 | 15.1 | 6.6 |
| 3 | 30.9 | 155 |
| 4 | 8.3 | 4.4 |
| 5 | 9.8 | 15.4 |
| 6 | 90.4 | 13.6 |
| 7 | 152 | 2.3 |
| 8 | 16.1 | 9.3 |
| 10 | 240 | 66.3 |
| 11 | 124 | 53.2 |
| 12 | 27.8 | 20.7 |
| 14 | 139 | 72 |
| 15 | 9.1 | 13.7 |
| 16 | 120 | 20.7 |
| 18 | 3.14 | 1.56 |
| 19 | 54 | 7.37 |
| 20 | 75 | 9.25 |
| 21 | 138 | 18 |

5. Animal Pharmacokinetic Study on Compounds

Three healthy adult male rats that obtained from Beijing Vital River Laboratory Animal Technology Co., Ltd were used for the animal pharmacokinetic experiment. A compound was suspended in 2% absolute ethanol, 5% tween 80, 20% polyethylene glycol 400, and 73% (5% hydroxypropylmethyl cellulose in water) (V/V/V/V) at a concentration of 1 mg/mL. The administration volume was 5 mL/kg, and animals were treated with a single intragastric administration at a dose of 5 mg/kg. Animals were fasted overnight prior to the experiment, and the fasting time was from 10 hours before administration to 4 hours after administration. Blood was sampled at 0.25, 0.5, 1, 2, 4, 6, 8 and 24 hours after administration. Animals were lightly anesthetized with isoflurane, and approximately 0.4 mL of whole blood was collected from the orbital venous plexus using a glass blood collection tube, and placed in a heparin anticoagulation tube. The sample was centrifuged at 4200 rpm for 5 minutes at 4° C., and then the plasma was transferred to a centrifuge tube and stored at −80° C. until analyzed. In the plasma sample analysis, test compounds and internal standards (warfarin or propranolol) were extracted from rat plasma by acetonitrile protein precipitation, and the extracts were analyzed by LC/MS/MS. The measured plasma concentration-time data of the individual animals were analyzed using a non-compartmental model of WinNonlin (version no. 5.2.1; Pharsight) software to give pharmacokinetic parameters as shown in Table 3 below: the maximum (peak) plasma drug concentration $C_{max}$; the time to peak $T_{max}$; the half-life $T_{1/2}$ and the area under the plasma concentration-time curve extrapolated to infinity $AUC_{0-inf}$.

TABLE 3

Results of study of pharmacokinetic parameters of compounds

| | | Numerical value | | |
|---|---|---|---|---|
| Parameters | Unit | Example compound 5 | Example compound 4 | Example compound 18 |
| $t_{1/2}$ | hr | 2.90 | 2.94 | 5.25 |
| $T_{max}$ | hr | 1.00 | 0.83 | 2.67 |
| $C_{max}$ | ng/ml | 610 | 459 | 372 |
| $AUC_{0-inf}$ | hr ng/ml | 2689 | 2298 | 3466 |

It can be seen that the compounds of the present application have good activity and good pharmacokinetic properties.

What is claimed is:

1. A compound of formula I or a pharmaceutically acceptable salt thereof,

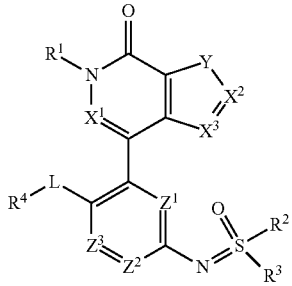

I wherein,

R$^1$ is selected from the group consisting of H, C$_1$-C$_3$ alkyl, and C$_1$-C$_3$ acyl, the C$_1$-C$_3$ alkyl or C$_1$-C$_3$ acyl is optionally substituted with one or more halogens;

Y is selected from the group consisting of O, S, and NR$^Y$, the R$^Y$ is selected from the group consisting of H, C$_1$-C$_3$ alkyl, and C$_1$-C$_3$ acyl, the C$_1$-C$_3$ alkyl or C$_1$-C$_3$ acyl is optionally substituted with one or more halogens;

X$^1$ is selected from the group consisting of N and CR$^{X1}$, the R$^{X1}$ is selected from the group consisting of H, C$_1$-C$_6$ alkyl, halogen, and C$_1$-C$_6$ haloalkyl;

X$^2$ is selected from the group consisting of N and CR$^{X2}$, and X$^3$ is selected from the group consisting of N and CR$^{X3}$, the R$^{X2}$ and R$^{X3}$ are each independently selected from the group consisting of H, halogen, C$_1$-C$_6$ alkyl, C$_2$-C$_6$ alkenyl, C$_2$-C$_6$ alkynyl, —C(O)OR$^a$, —C(O)NR$^b$R$^c$, —C(O)R$^d$, —S(O)$_2$R$^e$, and —S(O)$_2$NR$^b$R$^c$, the C$_1$-C$_6$ alkyl, C$_2$-C$_6$ alkenyl, or C$_2$-C$_6$ alkynyl is optionally substituted with one or more halogen, hydroxyl, amino, nitro, or cyano;

Z$^1$ is N, Z$^2$ is selected from the group consisting of N and CR$^{Z2}$, and Z$^3$ is selected from the group consisting of N and CR$^{Z3}$, the R$^{Z2}$, and R$^{Z3}$ are each independently selected from the group consisting of H, C$_1$-C$_6$ alkyl, C$_2$-C$_6$ alkenyl, C$_2$-C$_6$ alkynyl, halogen, cyano, and nitro, the C$_1$-C$_6$ alkyl, C$_2$-C$_6$ alkenyl, or C$_2$-C$_6$ alkynyl is optionally substituted with one or more halogens, hydroxyl, amino, nitro, or cyano; or Z$^1$ is selected from the group consisting of N and CR$^{Z1}$, Z$^2$ is N, and Z$^3$ is selected from the group consisting of N and CR$^{Z3}$, the R$^{Z1}$ and R$^{Z3}$ are each independently selected from the group consisting of H, C$_1$-C$_6$ alkyl, C$_2$-C$_6$ alkenyl, C$_2$-C$_6$ alkynyl, halogen, cyano, and nitro, the C$_1$-C$_6$ alkyl, C$_2$-C$_6$ alkenyl, or C$_2$-C$_6$ alkynyl is optionally substituted with one or more halogens, hydroxyl, amino, nitro, or cyano; or Z$^1$ is selected from the group consisting of N and CR$^{Z1}$, Z$^2$ is selected from the group consisting of N and CR$^{Z2}$, and Z$^3$ is N, the R$^{Z1}$ and R$^{Z2}$ are each independently selected from the group consisting of H, C$_1$-C$_6$ alkyl, C$_2$-C$_6$ alkenyl, C$_2$-C$_6$ alkynyl, halogen, cyano, and nitro, the C$_1$-C$_6$ alkyl, C$_2$-C$_6$ alkenyl, or C$_2$-C$_6$ alkynyl is optionally substituted with one or more halogens, hydroxyl, amino, nitro, or cyano;

R$^2$ and R$^3$ are each independently selected from the group consisting of halogen, hydroxyl, C$_1$-C$_6$ alkyl, C$_2$-C$_6$ alkenyl, C$_2$-C$_6$ alkynyl, C$_1$-C$_6$ alkoxy, C$_1$-C$_6$ alkylamino, and (C$_1$-C$_6$ alkyl)$_2$ amino, the C$_1$-C$_6$ alkyl, C$_2$-C$_6$ alkenyl, C$_2$-C$_6$ alkynyl, C$_1$-C$_6$ alkoxy, C$_1$-C$_6$ alkylamino, or (C$_1$-C$_6$ alkyl)$_2$ amino is optionally substituted with one or more halogens, hydroxyl, amino, nitro, or cyano; or R$^2$ and R$^3$ are connected and form a 3-8 membered heterocycloalkyl together with an adjacent S atom, the 3-8 membered heterocycloalkyl optionally contains 1-3 heteroatoms selected from the group consisting of N, O, and S, in addition to the S atom to which R$^2$ and R$^3$ are both connected; and the ring carbon atoms of the 3-8 membered heterocycloalkyl are optionally substituted with one or more halogens, hydroxyl, amino, nitro, cyano, C$_1$-C$_6$ alkyl, C$_1$-C$_6$ haloalkyl, C$_1$-C$_6$ alkoxy, C$_1$-C$_6$ alkylamino, or (C$_1$-C$_6$ alkyl)$_2$ amino, or substituted with one or more oxo;

L is selected from the group consisting of a single bond, —O—, —NH—, —(C$_1$-C$_3$ alkyl)-O—, —(C$_1$-C$_3$ alkyl)-NH—, and —C$_1$-C$_3$ alkyl-; and R$^4$ is selected from the group consisting of C$_6$-C$_{10}$ aryl, C$_3$-C$_{10}$ cycloalkenyl, C$_3$-C$_{10}$ cycloalkyl, 3-10 membered heteroaryl, 3-10 membered heterocycloalkenyl, and 3-10 membered heterocycloalkyl, the 3-10 membered heteroaryl, 3-10 membered heterocycloalkenyl, or 3-10 membered heterocycloalkyl each independently contains 1-3 heteroatoms selected from the group consisting of N, O, and S; and R$^4$ is optionally substituted with one or more halogens, hydroxyl, amino, nitro, cyano, C$_1$-C$_6$ alkyl, C$_1$-C$_6$ haloalkyl, C$_1$-C$_6$ alkoxy, C$_1$-C$_6$ alkylamino, (C$_1$-C$_6$ alkyl)$_2$ amino, —C(O)OR$^a$, —C(O)NR$^b$R$^c$, —C(O)R$^d$, —S(O)$_2$R$^e$, —NHS(O)$_2$R$^e$, or —S(O)$_2$NR$^b$R$^c$, or substituted with one or more oxo;

the R$^a$, R$^b$, R$^c$, R$^d$, and R$^e$ are each independently selected from the group consisting of H, C$_1$-C$_6$ alkyl, and C$_1$-C$_6$ haloalkyl.

2. The compound of formula I or the pharmaceutically acceptable salt thereof according to claim 1, wherein R$^1$ is selected from the group consisting of H and C$_1$-C$_3$ alkyl, the C$_1$-C$_3$ alkyl is optionally substituted with one or more F, Cl, or Br.

3. The compound of formula I or the pharmaceutically acceptable salt thereof according to claim 1, wherein Y is NR$^Y$, the R$^Y$ is selected from the group consisting of H and C$_1$-C$_3$ alkyl, the C$_1$-C$_3$ alkyl is optionally substituted with one or more F, Cl, or Br.

4. The compound of formula I or the pharmaceutically acceptable salt thereof according to claim 1, wherein X$^1$ is CR$^{X1}$, the R$^{X1}$ is selected from the group consisting of H, C$_1$-C$_4$ alkyl, F, Cl, Br, and C$_1$-C$_4$ alkyl substituted with F, Cl, or Br.

5. The compound of formula I or the pharmaceutically acceptable salt thereof according to claim 1, wherein X$^2$ is CR$^{X2}$, the R$^{X2}$ is selected from the group consisting of H, —C(O)OR$^a$, and —C(O)NR$^b$R$^c$.

6. The compound of formula I or the pharmaceutically acceptable salt thereof according to claim 1, wherein X$^3$ is CR$^{X3}$, the R$^{13}$ is selected from the group consisting of H and C$_1$-C$_4$ alkyl, the C$_1$-C$_4$ alkyl is optionally substituted with one or more F, Cl, Br, hydroxyl, amino, nitro, or cyano.

7. The compound of formula I or the pharmaceutically acceptable salt thereof according to claim 1, wherein the $R^{Z1}$ is selected from the group consisting of H, $C_1$-$C_4$ alkyl, $C_2$-$C_4$ alkenyl, $C_2$-$C_4$ alkynyl, halogen, cyano, and nitro, the $C_1$-$C_4$ alkyl, $C_2$-$C_4$ alkenyl, or $C_2$-$C_4$ alkynyl is optionally substituted with one or more halogen, hydroxyl, amino, nitro, or cyano.

8. The compound of formula I or the pharmaceutically acceptable salt thereof according to claim 1, wherein the $R_{Z2}$ is selected from the group consisting of H, $C_1$-$C_4$ alkyl, $C_2$-$C_4$ alkenyl, $C_2$-$C_4$ alkynyl, halogen, cyano, and nitro, the $C_1$-$C_4$ alkyl, $C_2$-$C_4$ alkenyl, or $C_2$-$C_4$ alkynyl is optionally substituted with one or more F, Cl, Br, hydroxyl, amino, nitro, or cyano.

9. The compound of formula I or the pharmaceutically acceptable salt thereof according to claim 1, wherein the $R^{Z3}$ is selected from H, $C_1$-$C_4$ alkyl, $C_2$-$C_4$ alkenyl, $C_2$-$C_4$ alkynyl, halogen, cyano, and nitro, the $C_1$-$C_4$ alkyl, $C_2$-$C_4$ alkenyl, or $C_2$-$C_4$ alkynyl is optionally substituted with one or more F, Cl, Br, hydroxyl, amino, nitro, or cyano.

10. The compound of formula I or the pharmaceutically acceptable salt thereof according to claim 1, wherein $R^2$ and $R^3$ are each independently selected from the group consisting of $C_1$-$C_4$ alkyl, $C_2$-$C_4$ alkenyl, $C_2$-$C_4$ alkynyl, $C_1$-$C_4$ alkoxy, $C_1$-$C_4$ alkylamino, and $(C_1$-$C_4$ alkyl$)_2$ amino, the $C_1$-$C_4$ alkyl, $C_2$-$C_4$ alkenyl, $C_2$-$C_4$ alkynyl, $C_1$-$C_4$ alkoxy, $C_1$-$C_4$ alkylamino, or $(C_1$-$C_4$ alkyl$)_2$ amino is optionally substituted with one or more F, Cl, Br, hydroxyl, amino, nitro, or cyano; or $R^2$ and $R^3$ are connected and form a 4-6 membered heterocycloalkyl together with an adjacent S atom, the 4-6 membered heterocycloalkyl optionally contains 1-3 heteroatoms selected from the group consisting of N, O and S in addition to the S atom to which the $R^2$ and $R^3$ are both connected; and the ring carbon atoms of the 4-6 membered heterocycloalkyl are optionally substituted with one or more F, Cl, Br, hydroxyl, amino, nitro, cyano, $C_1$-$C_4$ alkyl, $C_1$-$C_4$ haloalkyl, $C_1$-$C_4$ alkoxy, $C_1$-$C_4$ alkylamino, or $(C_1$-$C_4$ alkyl$)_2$ amino, or substituted with one or more oxo.

11. The compound of formula I or the pharmaceutically acceptable salt thereof according to claim 1, wherein L is selected from the group consisting of a single bond, —O—, —NH—, and —($C_1$-$C_3$ alkyl)-O—.

12. The compound of formula I or the pharmaceutically acceptable salt thereof according to claim 1, wherein $R^4$ is selected from the group consisting of phenyl, naphthyl, piperidinyl, pyridinyl, imidazolyl, pyrazolyl, pyrazinyl, piperazinyl, thienyl, furanyl, thiazolyl, isothiazolyl, oxazolyl, isoxazolyl, 1,4-dihydropyridinyl, and tetrahydrofuranyl; and $R^4$ is optionally substituted with one or more F, Cl, Br, cyano, methyl, ethyl, propyl, butyl, trifluoromethyl, methoxy, ethoxy, propoxy, methylamino, ethylamino, propylamino, (methyl)$_2$ amino, (ethyl)$_2$ amino, (propyl)$_2$ amino, —C(O)OH, —C(O)OCH$_3$, —C(O)OC$_2$H$_5$, —C(O)NH$_2$, —C(O)NHCH$_3$, —C(O)NHC$_2$H$_5$, —C(O)N(CH$_3$)$_2$, —C(O)N(C$_2$H$_5$)$_2$, acetyl, —S(O)$_2$CH$_3$, —S(O)$_2$C$_2$H$_5$, —NHS(O)$_2$CH$_3$, —NHS(O)$_2$C$_2$H$_5$, —S(O)$_2$NH$_2$, —S(O)$_2$NHCH$_3$, —S(O)$_2$NHC$_2$H$_5$, —S(O)$_2$N(CH$_3$)$_2$, —S(O)$_2$N(C$_2$H$_5$)$_2$, or substituted with one or more oxo.

13. The compound of formula I or the pharmaceutically acceptable salt thereof according to claim 1, wherein the compound is selected from a compound of formula II or a pharmaceutically acceptable salt thereof,

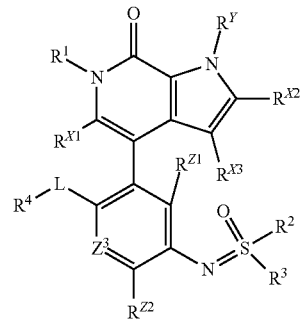

wherein $R^1$, $R^Y$, $R^{X1}$, $R^{X2}$, $R^{X3}$, $R^{Z1}$, $R^{Z2}$, $Z^3$, $R^2$, $R^3$, L and $R^4$ are defined above.

14. The compound of formula I or the pharmaceutically acceptable salt thereof according to claim 1, wherein the compound is selected from a compound of formula III or a pharmaceutically acceptable salt thereof,

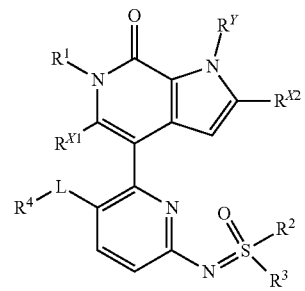

wherein $R^1$, $R^Y$, $R^{X1}$, $R^{X2}$, $R^2$, $R^3$, L and $R^4$ are defined above.

15. The compound of formula I or the pharmaceutically acceptable salt thereof according to claim 1, wherein the compound is selected from a compound of formula IV or a pharmaceutically acceptable salt thereof,

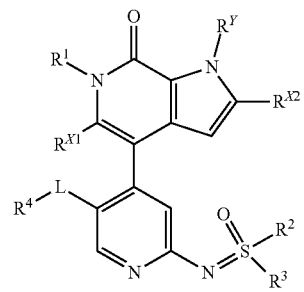

wherein $R^1$, $R^Y$, $R^{X1}$, $R^{X2}$, $R^2$, $R^3$, L and $R^4$ are defined above.

16. The compound of formula I or the pharmaceutically acceptable salt thereof according to claim 1, wherein the compound is selected from a compound of formula V or a pharmaceutically acceptable salt thereof,

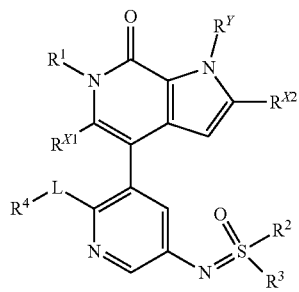
wherein $R^1$, $R^Y$, $R^{X1}$, $R^{X2}$, $R^2$, $R^3$, L and $R^4$ are defined above.
17. A compound or a pharmaceutically acceptable salt thereof, wherein the compound is selected from the group consisting of the following compounds:
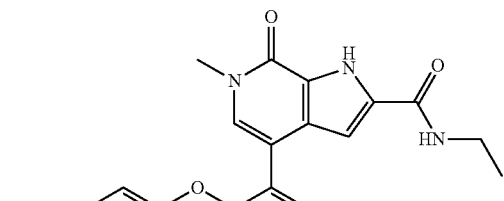
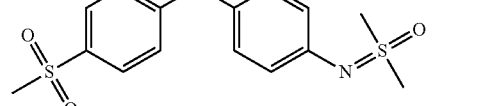
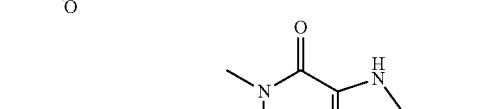
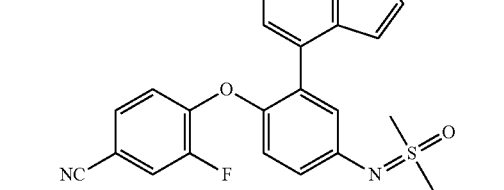
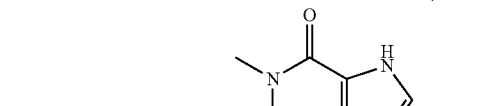
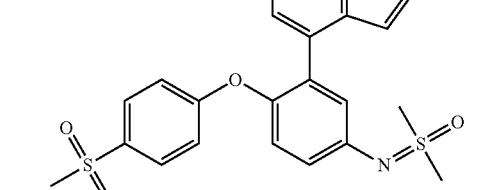
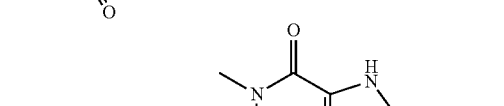
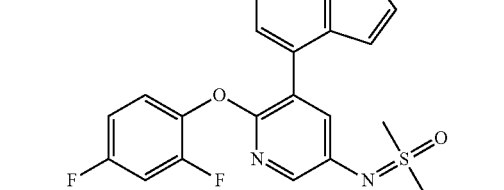
-continued
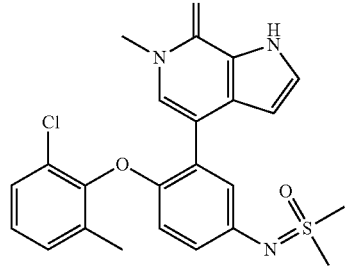
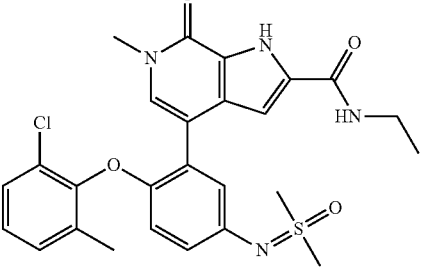
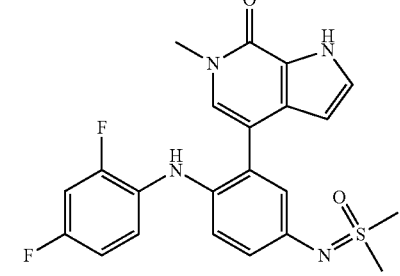
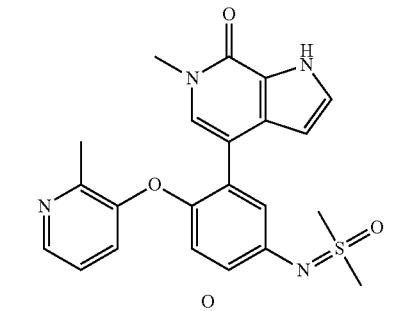
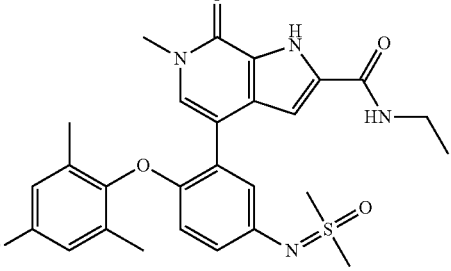
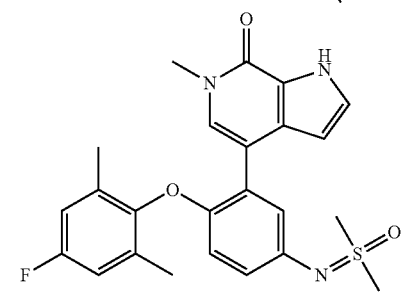

91
-continued
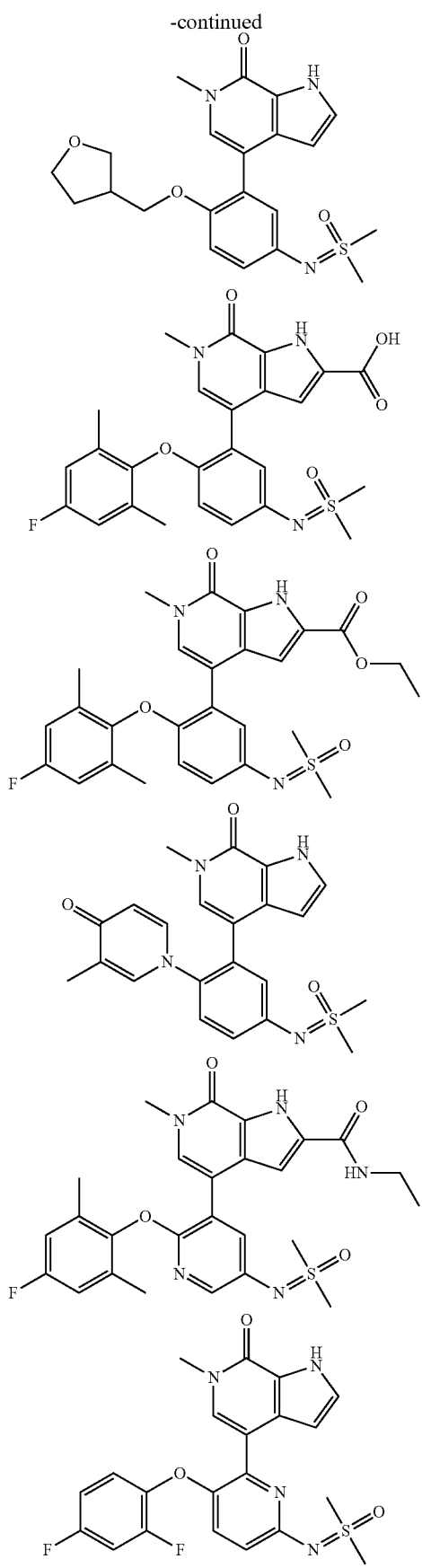
92
-continued
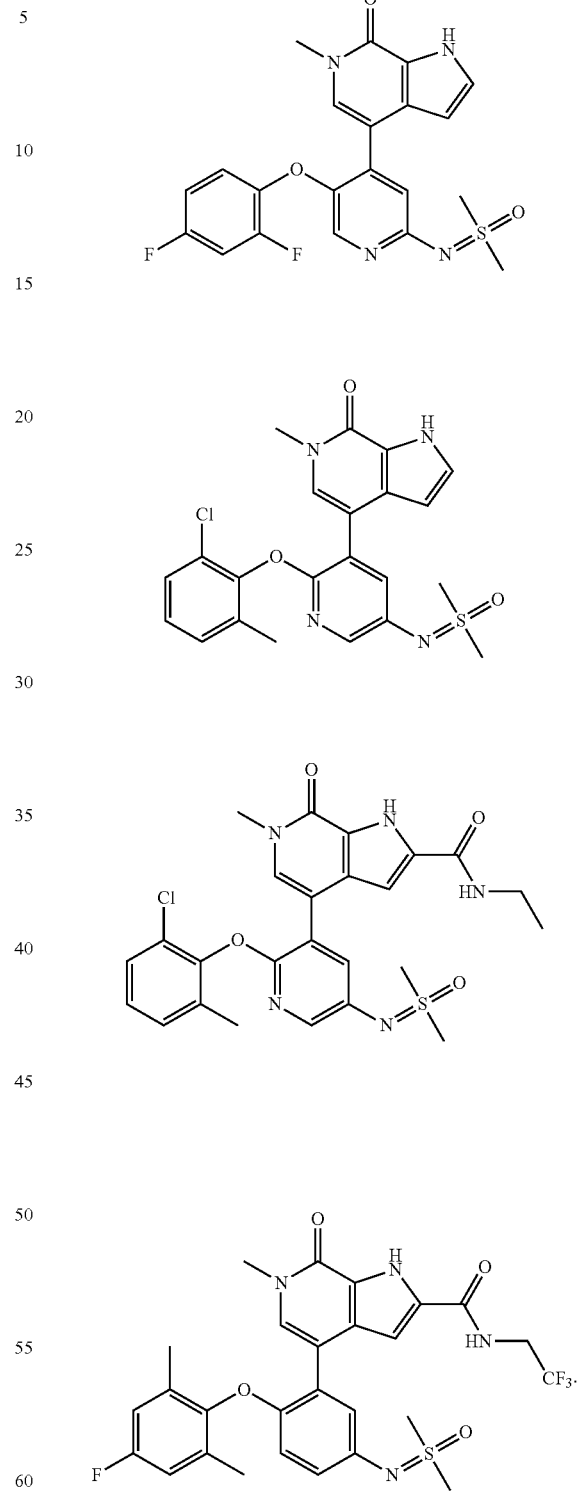
18. A pharmaceutical composition, comprising the compound of formula I or the pharmaceutically acceptable salt thereof according to claim 1.
* * * * *

UNITED STATES PATENT AND TRADEMARK OFFICE
CERTIFICATE OF CORRECTION

PATENT NO. : 12,030,880 B2
APPLICATION NO. : 17/262053
DATED : July 9, 2024
INVENTOR(S) : Li et al.

Page 1 of 1

It is certified that error appears in the above-identified patent and that said Letters Patent is hereby corrected as shown below:

In the Claims

At Column 86, Line 65 (Claim 6, Line 3), please delete "$R^{13}$" and insert --$R^{X3}$-- therefor.

At Column 87, Line 9 (Claim 8, Line 2), please delete "$R_{Z2}$" and insert --$R^{Z2}$-- therefor.

Signed and Sealed this
Third Day of September, 2024

Katherine Kelly Vidal
*Director of the United States Patent and Trademark Office*